(12) United States Patent
Chong et al.

(10) Patent No.: US 8,927,593 B2
(45) Date of Patent: Jan. 6, 2015

(54) BENZOFURAN COMPOUNDS FOR THE TREATMENT OF HEPATITIS C VIRUS INFECTIONS

(75) Inventors: Pek Yoke Chong, Durham, NC (US); John Brad Shotwell, Durham, NC (US)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 13/885,500

(22) PCT Filed: Aug. 10, 2012

(86) PCT No.: PCT/US2012/050268
§ 371 (c)(1),
(2), (4) Date: May 15, 2013

(87) PCT Pub. No.: WO2013/028371
PCT Pub. Date: Feb. 28, 2013

(65) Prior Publication Data
US 2013/0237501 A1    Sep. 12, 2013

Related U.S. Application Data

(60) Provisional application No. 61/525,440, filed on Aug. 19, 2011, provisional application No. 61/650,681, filed on May 23, 2012.

(51) Int. Cl.
| | | |
|---|---|---|
| *A01N 43/02* | (2006.01) | |
| *A61K 31/335* | (2006.01) | |
| *A01N 43/08* | (2006.01) | |
| *A61K 31/34* | (2006.01) | |
| *C07F 5/02* | (2006.01) | |
| *A61K 31/343* | (2006.01) | |
| *A61K 31/69* | (2006.01) | |

(52) U.S. Cl.
CPC ............... *C07F 5/027* (2013.01); *A61K 31/343* (2013.01); *A61K 31/69* (2013.01)
USPC ............................ 514/449; 514/461; 514/468

(58) Field of Classification Search
USPC .................................. 514/183, 449, 461, 468
See application file for complete search history.

(56) References Cited

U.S. PATENT DOCUMENTS

| | | |
|---|---|---|
| 6,297,217 B1 | 10/2001 | Adams et al. |
| 7,265,152 B2 | 9/2007 | Saha et al. |
| 7,666,863 B2 | 2/2010 | Saha et al. |
| 2007/0231318 A1 | 10/2007 | Saha et al. |
| 2007/0286822 A1 | 12/2007 | Sanders et al. |

FOREIGN PATENT DOCUMENTS

| | | |
|---|---|---|
| WO | WO 01/02424 | 1/2001 |
| WO | WO 2004/041201 | 4/2004 |
| WO | 2007/095638 | 8/2007 |
| WO | WO 2009/101022 | 8/2009 |
| WO | 2009/111676 | 9/2009 |
| WO | WO 2009/137493 | 11/2009 |
| WO | WO 2009/137500 | 11/2009 |
| WO | 2010/027975 | 3/2010 |
| WO | WO 2010/025138 | 3/2010 |
| WO | 2011/103063 | 8/2011 |
| WO | WO 2011/103063 | 8/2011 |
| WO | WO 2011/106929 | 9/2011 |
| WO | WO 2011/106986 | 9/2011 |
| WO | WO 2011/106992 | 9/2011 |
| WO | WO 2012/067663 | 5/2012 |
| WO | WO 2012/067664 | 5/2012 |
| WO | WO2013025975 | * 2/2013 |
| WO | WO2013025992 | * 2/2013 |

* cited by examiner

*Primary Examiner* — Yong Chong
(74) *Attorney, Agent, or Firm* — Robert Steve Thomas

(57) ABSTRACT

The present invention features compounds of formula (I):

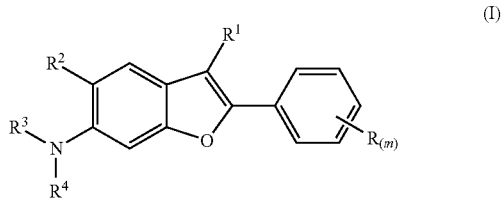

and salts thereof, pharmaceutical compositions comprising said compounds, and uses of such compounds in treating or preventing viral infections, such as HCV infections, and diseases associated with such infections.

3 Claims, No Drawings

BENZOFURAN COMPOUNDS FOR THE TREATMENT OF HEPATITIS C VIRUS INFECTIONS

CROSS-REFERENCE TO RELATED APPLICATIONS

This application is filed pursuant to 35 USC §371 as a United States National Phase Application of International Patent Application Serial No. PCT/US2012/050268 filed on Aug. 10, 2012, which claims priority from U.S. Provisional Application No. 61/525,440 filed on Aug. 19, 2011 and U.S. Provisional Application No. 61/650,681 filed on May 23, 2012 in the United States,

FIELD OF THE INVENTION

The present invention relates to compounds useful as antiviral agents, specifically Hepatitis C Virus (HCV) inhibitors, pharmaceutical compositions comprising said compounds, and uses of such compounds in treating or preventing viral infections, such as HCV infections, and diseases associated with such infections.

BACKGROUND OF THE INVENTION

Infection with HCV is a major cause of human liver disease throughout the world. Chronic infection with HCV is associated with chronic liver disease, cirrhosis, hepatocellular carcinoma, and liver failure. HCV is a hepacivirus member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. While the pathology of HCV infection affects mainly the liver, the virus is found in other cell types in the body including peripheral blood lymphocytes.

HCV is major causative agent for post-transfusion and for sporadic hepatitis. Infection by HCV is insidious in a high proportion of chronically infected, and infectious, carriers who may not experience clinical symptoms for many years. An estimated 170 million chronic carriers worldwide are at risk of developing liver disease.

Due to the high degree of variability in the viral surface antigens, existence of multiple viral genotypes, and demonstrated specificity of immunity, the development of a successful vaccine in the near future is unlikely. Alpha-interferon, alone or in combination with ribavirin, has been widely used for treatment of chronic HCV infection. However, treatment of HCV with interferon has frequently been associated with adverse side effects such as fatigue, fever, chills, headache, leukopenia, thrombocytopenia, psychiatric effects and associated disorders, autoimmune phenomena and associated disorder and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin.

Recently, with the introduction of pegylated interferon, both initial and sustained response rates have improved, and combination treatment of Peg-IFN with ribavirin constitutes the gold standard for therapy. However, the side effects associated with combination therapy persist. Ribavirin causes significant hemolysis in 10-20% of patients treated at currently recommended doses, and the drug is both teratogenic and embryotoxic. Furthermore, a substantial number of patients do not respond with a sustained reduction in viral load, and there is a clear need for more effective antiviral therapy for HCV infection.

A number of approaches are being pursued to combat the virus. These include, for example, application of antisense oligonucleotides or ribozymes for inhibiting HCV replication. Furthermore, low-molecular weight compounds that directly inhibit HCV proteins and interfere with viral replication are considered attractive strategies to control HCV infection. Among the viral targets, the NS3/4a protease/helicase and the NS5b RNA-dependent RNA polymerase are considered the most promising viral targets for new drugs.

Based on the foregoing, there exists a significant need for new effective drugs for treating infections caused by HCV.

SUMMARY OF THE INVENTION

The present invention provides benzofuran compounds substituted at the 6-position with a boron-containing moiety, pharmaceutical compositions comprising said compounds, methods of synthesis and uses of such compounds in treating and/or preventing viral infections, such as flavivirus infections, for example, HCV infections.

DETAILED DESCRIPTION OF THE INVENTION

The present invention provides a compound of formula (I):

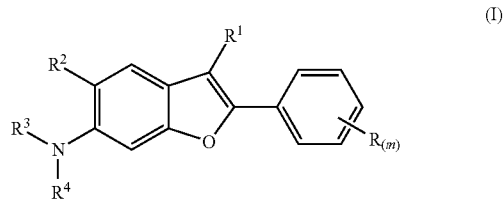

(I)

wherein:

R is independently selected from the group consisting of halogen, $C_{1-6}$alkyl, alkoxy, —CN, —$CF_3$, —O—$C_{6-10}$aryl optionally substituted by halogen, and —O-heteroaryl optionally substituted by halogen;

$R^1$ is —C(O)OH, —C(O)NH$R^5$ or heterocyclyl;

$R^2$ is $C_{1-6}$alkyl, $C_{3-6}$cycloalkyl, —C(H)$F_2$, —$CF_3$, or —O$R^6$;

$R^3$ is —S(O)$_2R^7$ or —C(O)$R^7$;

$R^4$ is (a) heteroaryl substituted with B($R^8$)($R^9$), XB($R^8$)($R^9$), OXB($R^9$)($R^9$), B$^-$($R^8$)($R^9$)($R^{12}$), XB($R^8$)$R^9$)($R^{12}$) or Het optionally substituted with hydroxy or hydroxyalkyl; and optionally substituted with one or more substituents independently selected from the group consisting of halogen, $C_{1-6}$alkoxy, —C(H)$F_2$, —$CF_3$, $C_{1-6}$alkyl, hydroxy, hydroxyalkyl, aminoalkyl, —C(O)NH$_2$, —C(O)OH, —C(O)NH$R^5$, —S(O)$_2R^6$, —S(O)$_2$NH$_2$, —CN, —OCF$_3$, —O$R^6$, —N$R^{10}R^{11}$, —NHC(O)$R^{10}$, $C_{3-6}$cycloalkyl, and heterocyclyl;

(b) $C_{6-10}$ aryl substituted with B($R^8$)($R^9$), XB($R^8$)($R^9$), OXB($R^8$($R^9$), B$^-$($R^8$)($R^9$)($R^{12}$), XB($R^8$)$R^9$)($R^{12}$) or Het optionally substituted with hydroxy or hydroxyalkyl; and optionally substituted with one or more substituents independently selected from the group consisting of halogen, $C_{1-6}$alkoxy, —C(H)F$_2$, —CF$_3$, $C_{1-6}$alkyl, hydroxy, hydroxyalkyl, aminoalkyl, —C(O)NH$_2$, —C(O)OH, —C(O)NHR$^5$, —S(O)$_2$R$^6$, —S(O)$_2$NH$_2$, —CN, —OCF$_3$, —OR$^6$, —NR$^{10}$R$^{11}$, —NHC(O)R$^{10}$, $C_{3-6}$cycloalkyl, and heterocyclyl; or (c) Het optionally substituted with one or more substituents independently selected from the group consisting of halogen, $C_{1-6}$alkoxy, —C(H)F$_2$, —CF$_3$, $C_{1-6}$alkyl, hydroxy, hydroxyalkyl, aminoalkyl, —C(O)NH$_2$, —C(O)OH, —C(O)NHR$^5$, —S(O)$_2$R$^6$, —S(O)$_2$NH$_2$, —CN, —OCF$_3$, —OR$^6$, —NR$^{10}$R$^{11}$, —NHC(O)R$^{10}$, $C_{3-6}$cycloalkyl, and heterocyclyl;

Het is a 5 or 6-membered monocyclic heterocyclic ring or 8- to 11-membered bicyclic heterocyclic ring system any ring of which is either saturated, partially saturated or unsaturated, which may be optionally benzofused if monocyclic or which may be optionally spiro-fused, and wherein each Het consists of one or more carbon atoms and one boron atom and one or more oxygen atoms; one boron atom, one oxygen atom, and one nitrogen atom; or one boron atom and one or more nitrogen atoms;

R$^5$ is hydrogen, $C_{1-6}$alkyl, hydroxy, or —OR$^6$;

R$^6$ is $C_{1-6}$alkyl or $C_{3-6}$cycloalkyl;

R$^7$ is $C_{1-6}$alkyl, hydroxyalkyl, or aminoalkyl;

R$^8$, R$^9$, and R$^{12}$ are each independently hydroxy, alkoxy, or aminoalkyl; or R$^8$ and R$^9$ or R$^8$, R$^9$, and R$^{12}$ together with the boron atom to which they are attached form a 5 to 14-membered ring, said ring comprising carbon atoms and optionally one or more heteroatoms which can be N or O; said ring may be optionally substituted with one or more substituents independently selected from the group consisting of $C_{1-6}$alkyl, hydroxyalkyl, aminoalkyl, amino, oxo, C(O)OH, C(O)OXOR$^{13}$, C(O)N(R$^{10}$)(R$^{11}$), N(R$^{10}$)(R$^{11}$), and $C_{3-6}$cycloalkyl each of which may be optionally substituted with one or more substituents independently selected from the group consisting of hydroxy, amino, halogen, C(O)OH, C(O)N(R$^{10}$)(R$^{11}$), and N(R$^{10}$)(R$^{11}$);

R$^{10}$ and R$^{11}$ are each independently hydrogen or $C_{1-6}$alkyl;

R$^{13}$ is alkoxy;

X is alkylene or —O-alkylene, wherein alkylene is optionally substituted with one or more substituents independently selected from the group consisting of halogen, $C_{1-6}$alkoxy, —C(H)F$_2$, —CF$_3$, $C_{1-6}$alkyl, hydroxy, hydroxyalkyl, aminoalkyl, —C(O)NH$_2$, —C(O)OH, —C(O)NHR$^5$, —S(O)$_2$R$^6$, —S(O)$_2$NH$_2$, —CN, —OCF$_3$, —OR$^6$, —NR$^{10}$R$^{11}$, —NHC(O)R$^{10}$ and $C_{3-6}$cycloalkyl;

m is 1, 2, or 3;

or a pharmaceutically acceptable salt thereof.

The term "alkyl" refers to a straight or branched hydrocarbon chain 1 to 6 carbon atoms unless otherwise specified. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

The term "alkylene" refers to a straight or branched chain divalent hydrocarbon radical, preferably having from one to ten carbon atoms, unless specified otherwise. Examples of "alkylene" as used herein include, but are not limited to, methylene, ethylene, n-propylene, n-butylene, and the like.

The term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, prop-1-oxy, prop-2-oxy, but-1-oxy, but-2-oxy, 2-methylprop-1-oxy, 2-methylprop-2-oxy, pentoxy and hexyloxy.

The term "halogen" or "halo" refers to a fluorine (fluoro, F), chlorine (chloro, Cl), bromine (bromo, Br) or iodine (iodo, I) atom.

The term "hydroxy" refers to a radical or substituent of the formula OH.

The term "cycloalkyl" refers to a saturated cyclic group containing 3 to 6 carbon ring-atoms (unless otherwise specified). Examples include cyclopropyl, cyclobutyl, cyclopentyl and cyclohexyl.

The term "aryl" refers to a carbocyclic aromatic moiety (such as phenyl or naphthyl) containing the specified number of carbon atoms, particularly from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "heteroaryl" refers to a 5-, 6-, 8-, 9- or 10-membered carbocyclic or bicyclic aromatic monocyclic or polycyclic ring radical containing five to twenty carbon atoms, preferably five to ten carbon atoms, in which one or more ring carbons, preferably one to four, are each replaced by a heteroatom such as N, O, and S. Preferred heteroaryl groups include 5-6 membered monocyclic heteroaryls and 8-10 membered bicyclic heteroaryls. Also included within the scope of the term is a group in which a non-aromatic heteroatom-containing ring is fused to one or more aromatic rings, such as in an indolinyl, chromanyl, phenanthridinyl or tetrahydro-quinolinyl, where the radical or point of attachment is on the non-aromatic heteroatom-containing ring. Heteroaryl moieties include, but are not limited to, pyridine, pyrazine, thiazole, thiophene, oxadiazole, oxazole, pyrimidine, pyridazine, triazole, tetrazole, benzodioxole, benzofuran, benzodioxin, indole, benzimidazole, benzofuran, indole, indazole, isoindole, benzothiophene, benzothiazole, benzoxazole, benzisoxazole, benzisothiazole, benzotriazole, furopyridine, furopyrimidine, furopyridazine, furopyrazine, furotriazine, pyrrolopyridine, pyrrolopyrimidine, pyrrolopyridazine, pyrrolopyrazine, pyrrolotriazine, thienopyridine, thienopyrimidine, thienopyridazine, thienopyrazine, thienotriazine, thiazolopyridine, thiazolopyrimidine, thiazolopyridazine, thiazolopyrazine, thiazolotriazine, oxazolopyridine, oxazolopyrimidine, oxazolopyridazine, oxazolopyrazine, oxazolotriazine, imidazopyridine, imidazopyrimidine, imidazopyridazine, imidazopyrazine, imidazotriazine, pyrazolopyridine, pyrazolopyrimidine, pyrazolopyridazine, pyrazolopyrazine, pyrazolotriazine, triazolopyridine, triazolopyrimidine, triazolopyridazine, triazolopyrazine, quinoline, naphthyridine, quinoxaline, quinazoline, isoquinoline, cinnoline, pyridopyridazine, pyridopyrimidine, pyridopyrazine, pyrazinopyrazine, pteridine, pyrazinopyridazine, pyrimidopyridazine, pyrimidopyrimidine, imidazothiazole and thiazolooxazole. All isomers of the above heteroaryl groups are within the scope of this invention. Each heteroaryl group may be attached at any ring carbon or may be attached through nitrogen when the nitrogen is part of a 5-membered ring.

The term "heteroatom" means nitrogen, oxygen, or sulfur and includes any oxidized form of nitrogen, such as N(O) {N$^+$—O$^-$} and sulfur such as S(O) and S(O)$_2$, and the quaternized form of any basic nitrogen.

The term "Het" refers to 5 or 6-membered monocyclic heterocyclic ring or 8- to 11-membered bicyclic heterocyclic ring system any ring of which is either saturated, partially saturated or unsaturated, which may be optionally benzo-fused if monocyclic or which may be optionally spiro-fused, and each Het consists of one or more carbon atoms and one boron atom and one or more oxygen atoms; one boron atom, one oxygen atom, and one nitrogen atom; or one boron atom and one or more nitrogen atoms. The Het may be attached at any carbon or N atom, provided that the attachment results in the creation of a stable structure. When the Het has substituents, it is understood that the substituents may be attached to any atom in the ring, provided that a stable chemical structure results. Preferred Het are oxaborolanyl, benzoxaborolyl, and dihyrobenzoxaborolyl.

The term "heterocyclyl" refers to a 3- to 7-membered monocyclic heterocyclic ring which is either saturated, partially saturated or unsaturated. Each heterocyclyl consists of one or more carbon atoms and one or more oxygen, nitrogen, or sulfur atoms. The heterocyclyl may be attached at any carbon or N atom, provided that the attachment results in the creation of a stable structure. When the heterocyclyl has substituents, it is understood that the substituents may be attached to any atom in the ring, provided that a stable chemical structure results. Preferred heterocyclyl is imidazolyl.

The present invention features a compound of formula (I) as described above wherein R is one or two halogen.

The present invention features a compound of formula (I) as described above wherein $R^1$ is —C(O)NHR$^5$.

The present invention features a compound of formula (I) as described above wherein $R^2$ is C$_{3-6}$cycloalkyl.

The present invention features a compound of formula (I) as described above wherein $R^3$ is —S(O)$_2$R$^7$ wherein R$^7$ is C$_{1-6}$alkyl.

The present invention features a compound of formula (I) as described above wherein $R^4$ is C$_{6-10}$aryl substituted with B(R$^8$)(R$^9$), wherein R$^8$ and R$^9$ are both hydroxy, and optionally substituted with one or more substituents independently selected from the group consisting of halogen, —CN, —C(H)F$_2$ and —CF$_3$ The present invention features a compound of formula (I) as described above wherein $R^4$ is heteroaryl substituted with B(R$^8$)(R$^9$), wherein R$^8$ and R$^9$ are both hydroxy, and optionally substituted with one or more substituents independently selected from the group consisting of halogen, —CN, —C(H)F$_2$ and —CF$_3$.

The present invention features a compound of formula (I) as described above wherein $R^5$ is C$_{1-6}$alkyl.

The present invention features a compound of formula (I) as described above wherein $R^6$ is C$_{1-6}$alkyl.

The present invention features a compound of formula (I) as described above wherein $R^7$ is C$_{1-6}$alkyl.

The present invention features a compound of formula (I) as described above wherein m is 1.

The present invention features a compound of formula (I) as described above wherein X is alkylene.

The present invention features a compound of formula (I) wherein R is halogen; m is 1; $R^1$ is —C(O)NHR$^5$ wherein R$^5$ is C$_{1-6}$alkyl; $R^2$ is C$_{3-6}$cycloalkyl; $R^3$ is —S(O)$_2$R$^7$ wherein R$^7$ is C$_{1-6}$alkyl and $R^4$ is C$_{6-10}$aryl substituted with B(R$^8$)(R$^9$) or X(R$^8$)(R$^9$), wherein R$^8$ and R$^9$ are both hydroxy; and wherein C$_{6-10}$aryl is optionally substituted with one or more substituents independently selected from the group consisting of halogen, —CN, —C(H)F$_2$ and —CF$_3$.

The present invention features a compound of formula (I) wherein R is halogen; m is 1; $R^1$ is —C(O)NHR$^5$ wherein R$^5$ is C$_{1-6}$alkyl; $R^2$ is C$_{3-6}$cycloalkyl; $R^3$ is —S(O)$_2$R$^7$ wherein R$^7$ is C$_{1-6}$alkyl and $R^4$ is heteroaryl substituted with B(R$^8$)(R$^9$) or X(R$^8$)(R$^9$), wherein R$^8$ and R$^9$ are both hydroxy and wherein heteroaryl is optionally substituted with one or more substituents independently selected from the group consisting of halogen, —CN, —C(H)F$_2$ and —CF$_3$ The present invention features a compound of formula (I) wherein R is halogen; m is 1; $R^1$ is —C(O)NHR$^5$ wherein R$^5$ is C$_{1-6}$alkyl; $R^2$ is C$_{3-6}$cycloalkyl; $R^3$—S(O)$_2$R$^7$ wherein R$^7$ is C$_{1-6}$alkyl, and $R^4$ is Het substituted with one or more substituents independently selected from the group consisting of halogen, hydroxy —CN, and oxo.

The present invention features a compound of formula (I) wherein R is halogen; m is 1; $R^1$ is —C(O)NHR$^5$ wherein R$^5$ is C$_{1-6}$alkyl; $R^2$ is C$_{3-6}$cycloalkyl; $R^3$—S(O)$_2$R$^7$ wherein R$^7$ is C$_{1-6}$alkyl, and $R^4$ is Het substituted with one or more substituents independently selected from the group consisting of halogen, hydroxyl, and —CN.

The present invention also provides a compound of formula (I)':

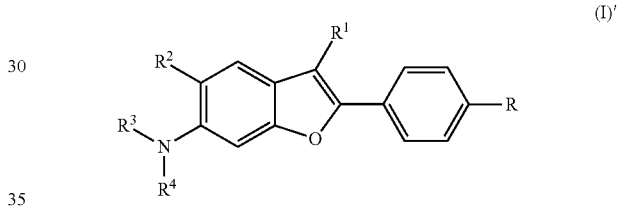

wherein:
R is F or Cl;
$R^1$ is —C(O)NHR$^5$;
$R^2$ is C$_{3-6}$cycloalkyl;
$R^3$ is —S(O)$_2$R$^7$;
$R^4$ is (a) heteroaryl substituted with B(R$^8$)(R$^9$) or XB(R$^8$)(R$^9$), and optionally substituted with one or more substituents independently selected from the group consisting of halogen, C$_{1-6}$alkoxy, —C(H)F$_2$, —CF$_3$, C$_{1-6}$alkyl, hydroxy, hydroxyalkyl, aminoalkyl, —C(O)NH$_2$, —C(O)OH, —C(O)NHR$^5$, —S(O)$_2$R$^6$, —S(O)$_2$NH$_2$, —CN, —OCF$_3$, —OR$^6$, —NR$^{10}$R$^{11}$, —NHC(O)R$^{10}$, C$_{3-6}$cycloalkyl, and heterocyclyl;

(b) C$_{6-10}$aryl substituted with B(R$^8$)(R$^9$), or XB(R$^8$)(R$^9$), and optionally substituted with one or more substituents independently selected from the group consisting of halogen, C$_{1-6}$alkoxy, —C(H)F$_2$, —CF$_3$, C$_{1-6}$alkyl, hydroxy, hydroxyalkyl, aminoalkyl, —C(O)NH$_2$, —C(O)OH, —C(O)NHR$^5$, —S(O)$_2$R$^6$, —S(O)$_2$NH$_2$, —CN, —OCF$_3$, —OR$^6$, —NR$^{10}$R$^{11}$, —NHC(O)R$^{10}$, C$_{3-6}$cycloalkyl, and heterocyclyl; or (c) Het optionally substituted with one or more substituents independently selected from the group consisting of halogen, C$_{1-6}$alkoxy, —C(H)F$_2$, —CF$_3$, C$_{1-6}$alkyl, hydroxy, hydroxyalkyl, aminoalkyl, —C(O)NH$_2$, —C(O)OH, —C(O)NHR$^5$, —S(O)$_2$R$^6$, —S(O)$_2$NH$_2$, —CN, —OCF$_3$, —OR$^6$, —NR$^{10}$R$^{11}$, —NHC(O)R$^{10}$, C$_{3-6}$cycloalkyl, and heterocyclyl;

Het is a 5 or 6-membered monocyclic heterocyclic ring or 8- to 11-membered bicyclic heterocyclic ring system any ring of which is either saturated, partially saturated or unsaturated, which may be optionally benzofused if monocyclic or which may be optionally spiro-fused, and wherein each Het consists of one or more carbon atoms and one boron atom and one or more oxygen atoms; one boron atom, one oxygen atom, and one nitrogen atom; or one boron atom and one or more nitrogen atoms;

$R^5$ is $C_{1-6}$alkyl;

$R^6$ is $C_{1-6}$alkyl or $C_{3-6}$cycloalkyl;

$R^7$ is $C_{1-6}$alkyl, hydroxyalkyl, or aminoalkyl;

$R^8$ and $R^9$ are each independently hydroxy, alkoxy, or aminoalkyl; or $R^8$ and $R^9$ together with the boron atom to which they are attached form a 5 to 14-membered ring, said ring comprising carbon atoms and optionally one or more heteroatoms which can be N or O; said ring may be optionally substituted with one or more substituents independently selected from the group consisting of $C_{1-6}$alkyl, hydroxyalkyl, aminoalkyl, amino, oxo, C(O)OH, C(O)OXOR$^{13}$, C(O)N($R^{10}$)($R^{11}$), N($R^{10}$)($R^{11}$), and $C_{3-6}$cycloalkyl each of which may be optionally substituted with one or more substituents independently selected from the group consisting of hydroxy, amino, halogen, C(O)OH, C(O)N($R^{10}$)($R^{11}$), and N($R^{10}$)($R^{11}$);

$R^{10}$ and $R^{11}$ are each independently hydrogen or $C_{1-6}$alkyl;

$R^{13}$ is alkoxy;

X is alkylene or —O-alkylene, wherein alkylene is optionally substituted with one or more substituents independently selected from the group consisting of halogen, $C_{1-6}$alkoxy, —C(H)F$_2$, —CF$_3$, $C_{1-6}$alkyl, hydroxy, hydroxyalkyl, aminoalkyl, —C(O)NH$_2$, —C(O)OH, —C(O)NHR$^5$, —S(O)$_2$R$^6$, —S(O)$_2$NH$_2$, —CN, —OCF$_3$, —OR$^6$, —NR$^{10}$R$^{11}$, —NHC(O)R$^{10}$ and $C_{3-6}$cycloalkyl;

or a pharmaceutically acceptable salt thereof.

The present invention features a compound of formula (I)' as described above, wherein $R^4$ is heteroaryl substituted with B($R^8$)($R^9$) or XB($R^8$)($R^9$), wherein $R^8$ and $R^9$ are each independently hydroxy, alkoxy, or aminoalkyl; and wherein heteroaryl is optionally substituted with one or more substituents independently selected from the group consisting of halogen, —CN, —C(H)F$_2$, and —CF$_3$.

The present invention features a compound of formula (I)' as described above, wherein $R^4$ is $C_{6-10}$aryl substituted with B($R^8$)($R^9$) or XB($R^8$)($R^9$), wherein $R^8$ and $R^9$ are each independently hydroxy, alkoxy, or aminoalkyl; and wherein $C_{6-10}$aryl is optionally substituted with one or more substituents independently selected from the group consisting of halogen, —CN, —C(H)F$_2$, and —CF$_3$.

The present invention features a compound of formula (I)' as described above, wherein $R^4$ is Het optionally substituted one or more substituents independently selected from the group consisting of halogen, $C_{1-6}$alkoxy, —C(H)F$_2$, —CF$_3$, $C_{1-6}$alkyl, hydroxy, hydroxyalkyl, aminoalkyl, —C(O)NH$_2$, —C(O)OH, —C(O)NHR$^5$, —S(O)$_2$R$^6$, —S(O)$_2$NH$_2$, —CN, —OCF$_3$, —OR$^6$, —NR$^{10}$R$^{11}$, —NHC(O)R$^{10}$, $C_{3-6}$cycloalkyl, and heterocyclyl; wherein Het is a 5- to 6-membered monocyclic heterocyclic ring or 8- to 11-membered bicyclic heterocyclic ring system any ring of which is either saturated, partially saturated or unsaturated wherein each Het consists of one or more carbon atoms and one boron atom and one or more oxygen atoms; one boron atom, one oxygen atom, and one nitrogen atom; or one boron atom and one or more nitrogen atoms.

The present invention features a compound of formula (I)' as described above, wherein $R^4$ is Het optionally substituted one or more substituents independently selected from the group consisting of halogen, $C_{1-6}$alkoxy, —C(H)F$_2$, —CF$_3$, $C_{1-6}$alkyl, hydroxy, hydroxyalkyl and aminoalkyl, The present invention features a compound of formula (I)' as described above, wherein $R^6$ is $C_{1-6}$alkyl.

The present invention features a compound of formula (I)' as described above, wherein $R^7$ is $C_{1-6}$alkyl.

The present invention features a compound of formula (I)' as described above, wherein $R^8$ and $R^9$ are each independently hydroxy.

The present invention features a compound of formula (I)' as described above, wherein X is alkylene.

The present invention features a compound of formula (I) or (I)' wherein $R^8$ and $R^9$ together with the boron atom to which they are attached form a 5 to 8-membered ring; said ring comprising carbon atoms and one or more oxygen atoms. Such 5 to 8-membered rings include those formed from pinanediol, pinacol, perfluoropinacol, ethylene glycol, diethylene glycol, catechol, 1,2,-cyclohexanediol, 1,3-propanediol, 2,3,-butanediol, 1,2,-butanediol, 1,4-butanediol, glycerol and diethanolamine.

The present invention features a compound selected from the group consisting of:

(2-Chloro-4-(N-(5-cyclopropyl-2-(4-fluorophenyl)-3-(methylcarbamoyl)benzofuran-6-yl)methylsulfonamido)phenyl)boronic acid;

(2-Chloro-4-(N-(2-(4-chlorophenyl)-5-cyclopropyl-3-(methylcarbamoyl)benzofuran-6-yl)methylsulfonamido)phenyl)boronic acid;

4-(N-(5-cyclopropyl-2-(4-fluorophenyl)-3-(methylcarbamoyl)benzofuran-6-yl)methylsulfonamido)phenylboronic acid;

3-(N-(5-cyclopropyl-2-(4-fluorophenyl)-3-(methylcarbamoyl)benzofuran-6-yl)methylsulfonamido)phenylboronic acid;

4-(N-(5-cyclopropyl-2-(4-fluorophenyl)-3-(methylcarbamoyl)benzofuran-6-yl)methylsulfonamido)-2-fluorophenylboronic acid;

4-(N-(5-cyclopropyl-2-(4-fluorophenyl)-3-(methylcarbamoyl)benzofuran-6-yl)methylsulfonamido)-3-fluorophenylboronic acid;

4-(N-(2-(4-chlorophenyl)-5-cyclopropyl-3-(methylcarbamoyl)benzofuran-6-yl)methylsulfonamido)-2-fluorophenylboronic acid;

6-(N-(5-cyclopropyl-2-(4-fluorophenyl)-3-(methylcarbamoyl)benzofuran-6-yl)methylsulfonamido)pyridin-3-ylboronic acid;

(4-(N-(5-cyclopropyl-2-(4-fluorophenyl)-3-(methylcarbamoyl)benzofuran-6-yl)methylsulfonamido)-2-(difluoromethyl)phenyl)boronic acid;

(4-(N-(5-cyclopropyl-2-(4-fluorophenyl)-3-(methylcarbamoyl)benzofuran-6-yl)methylsulfonamido)-2-(trifluoromethyl)phenyl)boronic acid;

(4-(N-(5-cyclopropyl-2-(4-fluorophenyl)-3-(methylcarbamoyl)benzofuran-6-yl)methylsulfonamido)-2,6-difluorophenyl)boronic acid;

(2-cyano-4-(N-(5-cyclopropyl-2-(4-fluorophenyl)-3-(methylcarbamoyl)benzofuran-6-yl)methylsulfonamido)phenyl)boronic acid 6-(N-(4-borono-3-chlorophenyl)methylsulfonamido)-2-(4-chlorophenyl)-5-cyclopropylbenzofuran-3-carboxylic acid;

(4-(N-(3-carbamoyl-2-(4-chlorophenyl)-5-cyclopropylbenzofuran-6-yl)methylsulfonamido)-2-chlorophenyl)boronic acid;

6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide;

(4-(N-(5-cyclopropyl-2-(4-fluorophenyl)-3-(methylcarbamoyl)benzofuran-6-yl)methylsulfonamido)-2-(methylsulfonyl)phenyl)boronic acid;

1-(2-Chloro-4-(N-(5-cyclopropyl-2-(4-fluorophenyl)-3-(methylcarbamoyl)benzofuran-6-yl)methylsulfonamido)phenyl)-4-methyl-2,6,7-trioxa-1-borabicyclo[2.2.2]octan-1-uide;

((4-(N-(5-Cyclopropyl-2-(4-fluorophenyl)-3-(methylcarbamoyl)benzofuran-6-yl)methylsulfonamido)phenoxy)methyl)boronic acid;

((2-Chloro-4-(N-(5-cyclopropyl-2-(4-fluorophenyl)-3-(methylcarbamoyl)benzofuran-6-yl)methylsulfonamido)phenoxy)methyl)boronic acid;

5-Cyclopropyl-2-(4-fluorophenyl)-6-(N-(1-hydroxy-1,3-dihydrobenzo[c][1,2]oxaborol-5-yl)methylsulfonamido)-N-methylbenzofuran-3-carboxamide;

(4-(N-(2-(4-Chlorophenyl)-5-cyclopropyl-3-(methylcarbamoyl)benzofuran-6-yl)methylsulfonamido)-2-cyanophenyl)boronic acid;

5-Cyclopropyl-2-(4-fluorophenyl)-N-methyl-6-(N-(3-methyl-4-(4,4,5,5-tetramethyl-1,3,2-dioxaborolan-2-yl)phenyl)methylsulfonamido)benzofuran-3-carboxamide;

(2-Chloro-4-(N-(5-cyclopropyl-2-(4-fluorophenyl)-3-(methylcarbamoyl)benzofuran-6-yl)methylsulfonamido)phenethyl)boronic acid;

5-Cyclopropyl-6-(N-(7-fluoro-1-hydroxy-1,3-dihydrobenzo[c][1,2]oxaborol-5-yl)methylsulfonamido)-2-(4-fluorophenyl)-N-methylbenzofuran-3-carboxamide;

6-(N-(3-Chloro-4-(2-hydroxy-1,2-oxaborolan-4-yl)phenyl)methylsulfonamido)-5-cyclopropyl-2-(4-fluorophenyl)-N-methylbenzofuran-3-carboxamide;

(3-(N-(5-Cyclopropyl-2-(4-fluorophenyl)-3-(methylcarbamoyl)benzofuran-6-yl)methylsulfonamido)phenethyl)boronic acid;

6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide;

6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide, enantiomer 1;

6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide, enantiomer 2;

5-Cyclopropyl-2-(4-fluorophenyl)-6-(N-(1-hydroxy-3,4-dihydro-1H-benzo[c][1,2]oxaborinin-6-yl)methylsulfonamido)-N-methylbenzofuran-3-carboxamide;

and pharmaceutically acceptable salts thereof.

Compounds of formula (I) and (I)', in which the boron-containing ring is directly linked to the sulfonamide, demonstrate increased metabolic stability compared to compounds of PCT/US2011/024822 (WO2011/103063) and PCT/US2011/024824 (WO2012/067663) in which the boron-containing ring is linked via an alkylene linker. Comparative pharmacokinetic studies in rat, dog, and monkey indicated that clearance was markedly improved (Table 2).

Certain compounds of formula (I) and (I)' may exist in stereoisomeric forms (e.g. they may contain one or more asymmetric carbon atoms). The individual stereoisomers (enantiomers and diastereomers) and mixtures of these are included within the scope of the present invention. The invention also extends to conformational isomers of compounds of formula (I) and (I)' and any geometric (cis and/or trans) isomers of said compounds. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

Diastereoisomeric mixtures of compounds of formula (I) and (I)' may be separated according to methods well known in the literature, for example by preparative HPLC or by chromatographic purifications. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

It is understood that compounds of formula (I) and (I)' may exist in tautomeric forms other than that shown in the formula and these are also included within the scope of the present invention.

It will also be appreciated that compounds of the invention which exist as polymorphs, and mixtures thereof, are within the scope of the present invention.

Substitution with isotopes such as deuterium, i.e. $^2$H, may afford certain therapeutic advantages resulting from greater metabolic stability, for example, increased in vivo half-life or reduced dosage requirements, and hence may be preferred in some circumstances.

The present invention also features a compound of formula (I) or (I)' or a pharmaceutically acceptable salt thereof. As used herein, the term "pharmaceutically acceptable" means a compound which is suitable for pharmaceutical use. The term "pharmaceutically acceptable" when used in relation to an ingredient which may be included in a pharmaceutical composition for administration to a patient, refers to that ingredient being acceptable in the sense of being compatible with any other ingredients present in the pharmaceutical composition and not being deleterious to the recipient thereof.

Salts of compounds of formula (I) and (I)' which are suitable for use in medicine are those wherein the counterion is pharmaceutically acceptable. However, salts having non-pharmaceutically acceptable counterions are within the scope of the present invention, for example, for use as intermediates in the preparation of other compounds of formula (I) or (I)' and their pharmaceutically acceptable salts. It will be appreciated that for use in medicine the salts of formula (I) and (I)' should be physiologically (i.e. pharmaceutically) acceptable.

The compounds of the present invention may be in the form of their free base or pharmaceutically acceptable salts, pharmaceutically acceptable solvates or pharmaceutically acceptable esters thereof.

Also included in the present invention are pharmaceutically acceptable salt complexes. The present invention also covers the pharmaceutically acceptable salts of the compounds of formula (I) and (I)'. As used herein, the term "pharmaceutically acceptable salts" refers to salts that retain the desired biological activity of the subject compound and exhibit minimal undesired toxicological effects. For a review on suitable salts see Berge et al, J. Pharm. Sci., 1977, 66, 1-19. The term "pharmaceutically acceptable salts" includes both pharmaceutically acceptable acid addition salts and pharmaceutically acceptable base addition salts. These pharmaceutically acceptable salts may be prepared in situ during the final isolation and purification of the compound, or by separately reacting the purified compound in its free acid or free base form with a suitable base or acid, respectively. The salt may precipitate from solution and be collected by filtration or may be recovered by evaporation of the solvent.

Therefore, according to a further aspect, the invention provides a pharmaceutically acceptable salt of a compound of formula (I) or (I)' and embodiments thereof.

In certain embodiments, compounds of formula (I) or (I)' may contain an acidic functional group and may therefore be capable of forming pharmaceutically acceptable base addition salts by treatment with a suitable base. A pharmaceutically acceptable base addition salt may be formed by reaction of a compound of formula (I) or (I)' with a suitable strong base, optionally in a suitable solvent such as an organic solvent, to give the base addition salt which may be isolated for example by crystallisation and filtration. Pharmaceutically acceptable base salts include ammonium salts (for example ammonium or tetraalkylammonium), metal salts, for example alkali-metal or alkaline-earth-metal salts (such as hydroxides, sodium, potassium, calcium or magnesium), organic amines (such as tris [also known as tromethamine or tris(hydroxymethyl)aminomethane], ethanolamine, diethylamine, triethanolamine, choline, isopropylamine, dicyclohexylamine or N-methyl-D-glucamine), cationic amino acids (such as arginine, lysine or histidine) or bases for insoluble salts (such as procaine or benzathine).

In certain embodiments, compounds according to formula (I) or (I)' may contain a basic functional group and may therefore be capable of forming pharmaceutically acceptable acid addition salts by treatment with a suitable acid. A pharmaceutically acceptable acid addition salt may be formed by reaction of a compound of formula (I) or (I)' with a suitable strong inorganic acid (such as hydrobromic, hydrochloric, sulfuric, nitric, phosphoric or perchloric) or a suitable strong organic acid, for example, sulfonic acids [such as p-toluenesulfonic, benzenesulfonic, methanesulfonic, ethanesulfonic, 2-hydroxyethanesulfonic, naphthalenesulfonic (e.g. 2-naphthalenesulfonic)], carboxylic acids (such as acetic, propionic, fumaric, maleic, benzoic, salicylic or succinic), anionic amino acids (such as glutamaic or aspartic), hydroxyl acids (such as citric, lactic, tartaric or glycolic), fatty acids (such as caproic, caprylic, decanoic, oleic or stearic) or acids for insoluble salts (such as pamoic or resinic [e.g. polystyrene sulfonate]), optionally in a suitable solvent such as an organic solvent, to give the salt which is usually isolated for example by crystallisation and filtration. In one embodiment, a pharmaceutically acceptable acid addition salt of a compound of formula (I) or (I)' is a salt of a strong acid, for example a hydrobromide, hydrochloride, hydroiodide, sulfate, nitrate, perchlorate, phosphate p-toluenesulfonic, benzenesulfonic or methanesulfonic salt.

It will be appreciated by those skilled in the art that organoboronic acids and/or their organoboronate esters may form "ate" complex addition salts, such as organoborate complex addition salts, in the presence of suitable nucleophilic complexing reagents. Suitable nucleophilic complexing reagents include, but are not limited to alkali metal hydroxides, for example lithium hydroxide, sodium hydroxide or potassium hydroxide, or fluoride. Examples of organoborate complex addition salts and methods for their preparation will be readily apparent. For example, one such suitable organoborate complex addition salt is an alkali metal trihydroxyorganoborate salt, such as a sodium trihydroxyorganoborate salt. By way of illustration, sodium trihydroxyarylborate and sodium trihydroxyalkylborate complex addition salts and methods for their preparation are described in Cammidge, A. N. et al, Org. Lett., 2006, 8, 4071-4074. Pharmaceutically acceptable "ate" complex addition salts as described herein are also considered to be within the scope of this invention.

The present invention features suitable pharmaceutically acceptable salts of the compounds of formula (I) and (I)' including acid salts, for example sodium, potassium, calcium, magnesium, ammonium, tetraalkylammonium and tris (tromethamine-tris(hydroxymethyl)aminomethane) salts and the like, or mono- or di-basic salts with the appropriate acid for example organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids and the like.

The present invention features pharmaceutically acceptable base addition salts of a compound of formula (I) or (I)' which are salts of a strong base, for example, sodium, lysine, ammonium, N-methyl-D-glucamine, potassium, choline, arginine (for example L-arginine) or magnesium. In a further aspect the salt is sodium, lysine, ammonium, N-methyl-D-glucamine, potassium, choline or arginine (for example L-arginine).

Other non-pharmaceutically acceptable salts, for example oxalates, may be used, for example in the isolation of compounds of formula (I) or (I)' and are included within the scope of this invention.

The invention includes within its scope all possible stoichiometric and non-stoichiometric forms of the salts of the compounds of formula (I) and (I)'.

The salts of a compound of formula (I) and (I)' may be prepared by contacting appropriate stoichiometric amounts of the free acid with the appropriate base in a suitable solvent. The free acid of a compound of formula (I) or (I)' may for example be in solution with the appropriate base added as a solid or both the free acid of a compound of formula (I) or (I)' and the appropriate acid may independently be in solution.

Suitable solvents for solubilising a compound of formula (I) or (I)' free acid include for example alcohols such as isopropanol; ketones such as acetone; acetonitrile or toluene. If the base is to be added as a solution in a solvent, the solvent used may include acetone, methanol or water.

The salts of a compound of formula (I) or (I)' may be isolated in solid form by conventional means from a solution thereof obtained as above. For example, a non-crystalline salt may be prepared by precipitation from solution, spray drying or freeze drying of solutions, evaporating a solution to a glass, or vacuum drying of oils, or solidification of melts obtained from reaction of the free base and the acid.

The salts of a compound of formula (I) and (I)' may be prepared by directly crystallising from a solvent in which the salt has limited solubility, or by triturating or otherwise crystallising a non-crystalline salt. For example, organic solvents such as acetone, acetonitrile, butanone, 1-butanol, ethanol, 1-propanol or tetrahydrofuran or mixtures of such solvents may be used. An improved yield of the salts may be obtained by the evaporation of some or all of the solvent or by crystallisation at elevated temperature followed by controlled cooling, for example in stages. Careful control of the precipitation temperature and seeding may be used to improve the reproducibility of the production process and the particle size distribution and form of the product.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of formula (I) and (I)' and solvates of the salts of the compounds of formula (I) and (I)' are included within the scope of the present invention.

As used herein, the term "solvate" refers to a complex of variable stoichiometry formed by a solute (in this invention, a compound of formula (I) or (I)' or a salt thereof) and a solvent. Such solvents for the purpose of the invention may not interfere with the biological activity of the solute. Examples of suitable solvents include water, methanol, ethanol and acetic acid. Most preferably the solvent used is water and the solvate may also be referred to as a hydrate.

Solvates of compounds of formula (I) and (I)' which are suitable for use in medicine are those wherein the solvent is pharmaceutically acceptable. However, solvates having non-pharmaceutically acceptable solvents are within the scope of the present invention, for example, for use as intermediates in the preparation of other compounds of formula (I) and their pharmaceutically acceptable salts and solvates.

Furthermore, some of the crystalline forms of the compounds of formula (I) and (I)' or salts and solvates thereof may exist in one or more polymorphic form, which are included in the present invention.

Prodrugs of the compounds of formula (I) and (I)' are included within the scope of the present invention.

It will be appreciated by those skilled in the art that certain protected derivatives of compounds of formula (I) or (I)', which may be made prior to a final deprotection stage, may not possess pharmacological activity as such, but may, in certain instances, be administered orally or parenterally and thereafter metabolised in the body to form compounds defined in the first aspect which are pharmacologically active. Such derivatives may therefore be described as "prodrugs". All protected derivatives and prodrugs of compounds defined in the first aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). Prodrugs may also be made by the methods disclosed in, for example, U.S. Pat. No. 6,958,319 and U.S. Pat. No. 6,297,217. It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds of formula (I) or (I)'. Suitable prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals, ketals, boronic esters and boronic acid anhydrides.

Boronate esters and anhydrides include those derived from sugars, such as a monosaccharide or disaccharide, for example glucose, sucrose, fructose, xylitol, mannitol and sorbitol. Such boronic esters can be prepared by any method known to one skilled in the art, for example, as described in the literature (see "p-Boronophenylalanine Complexes with Fructose and Related Carbohydrates and Polyols" PCT/US00/07833) and "Cyclic Triolborates: Air- and Water-Stable Ate Complexes of Organoboronic Acids" *Angew. Chem. Int. Ed.* 2008, 47, 928). Boronic esters and boronic anhydrides bearing a nitrogen atom bound to boron can also be prepared by those skilled in the art as described in the literature (for example, see "A Method for the Deprotection of Alkylpinacolyl Boronate Esters" *J. Org. Chem.* 2011, 76, 3571 and also "Chemoselective Suzuki Coupling of Diborylmethane for Facile Synthesis of Benzylboronates" *Org. Letters* 2011, 13, 3368).

Boronic acids can be converted to the corresponding boronic esters via treatment with an alcohol (for example ethanol) or diol (for example pinacol) in a suitable solvent (for example toluene) with a dehydrating agent (for example powdered molecular sieves).

The compounds of the invention have been found to exhibit antiviral activity, specifically HCV inhibitory activity, and may therefore useful in treating or preventing viral infections, such as HCV infections, or diseases associated with such infections.

The present invention provides a compound of formula (I) or (I)' or a pharmaceutically acceptable salt thereof for use in medical therapy.

The present invention provides the use of a compound of formula (I) or (I)' or a pharmaceutically acceptable salt thereof for the manufacture of a medicament for treating and/or preventing viral infections, such as HCV infections, and/or diseases associated with such infections.

The present invention provides a compound of formula (I) or (I)' or a pharmaceutically acceptable salt thereof for use in treating and/or preventing viral infections, such as HCV infections, and/or diseases associated with such infections.

The present invention provides a method for treating or preventing viral infections, such as HCV infections, or diseases associated with such infections which method comprises administering to a subject, for example a human, a therapeutically effective amount of a compound of formula (I) or (I)' or a pharmaceutically acceptable salt thereof.

It will be appreciated that reference herein to therapy or treatment may include, but is not limited to prevention, retardation, prophylaxis, and cure of the disease. The present invention provides compounds and pharmaceutical compositions for the treatment of viral infections, such as HCV infections, as well as diseases associated with viral infections in living hosts. It will further be appreciated that references herein to treatment or prophylaxis of HCV infection include treatment or prophylaxis of HCV-associated disease such as liver fibrosis, cirrhosis and hepatocellular carcinoma.

The present invention provides compounds and pharmaceutical compositions for the prevention of viral infections, such as HCV infections, as well as diseases associated with viral infections in living hosts. It will further be appreciated that references herein to prevention or prophylaxis of HCV infection include treatment or prophylaxis of HCV-associated disease such as liver fibrosis, cirrhosis and hepatocellular carcinoma.

The compounds of formula (I) and (I)' may be made by the processes described herein or by any method known to those skilled in the art.

The invention also includes a pharmaceutical composition comprising a compound of formula (I) or pharmaceutically acceptable salt thereof together with at least one pharmaceutically acceptable excipient. The term "excipient" refers to a compound that is useful in preparing a pharmaceutical composition, e.g. diluent, carrier.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation. The dosage forms and procedures may involve amorphous dispersions, molecular dispersions, hot melt extrusion, particle size reduction through micronization or wet bead milling (nanomilling), self emulsifying systems, or complexation, for example cyclodextrin.

The pharmaceutical compositions of the invention may be formulated for administration by any route, and include those in a form adapted for oral, topical, intravenous, intraperitoneal, subcutaneous, intramuscular, transdermal or transmucosal administration.

For oral administration, the compounds can be formulated into any suitable dosage form, for example, tablets, capsules, powders, granules, lozenges, creams or liquid preparations, such as oral or sterile solutions or suspensions, syrups, elixirs and concentrated drops.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Where the composition is in the form of a capsule, any routine encapsulation is suitable, for example a hard gelatin capsule shell or a soft gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents. A syrup formulation will generally consist of a suspension or solution of the compound or salt in a liquid carrier for example, ethanol, peanut oil, olive oil, glycerine or water with a flavoring or coloring agent.

For injection (parenteral administration) e.g. intramuscular, intravenous, intraperitoneal, subcutaneous, fluid unit dosage forms are prepared utilising the compound and a sterile vehicle, for example water, saline solution, Hank's solution or Ringer's solution. The compound, depending on the vehicle and concentration used, can be either suspended or dissolved in the vehicle. In preparing solutions, the compound can be dissolved in water for injection and filter sterilised before filling into a suitable vial or ampoule and sealing. In addition, the compounds of the invention may be formulated in solid form and redissolved or suspended immediately prior to use. Lyophilized forms can also be produced. Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories. A typical suppository formulation comprises a compound of formula (I) or (I)' or a pharmaceutically acceptable salt thereof which is active when administered in this way, with a binding and/or lubricating agent, for example polymeric glycols, gelatins, cocoa-butter or other low melting vegetable waxes or fats or their synthetic analogs. Typical compositions for inhalation are in the form of a solution, suspension or emulsion that may be administered as a dry powder or in the form of an aerosol using a conventional non-CFC propellant such as 1,1,1,2-tetrafluoroethane or 1,1,1,2,3,3,3-heptafluoropropane.

The topical formulations of the present invention may be presented as, for instance, ointments, creams, gels, salves or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions.

Preparations may be suitably formulated to give controlled/extended release of the active compound.

The amounts of various compounds to be administered can be determined by standard procedures taking into account factors such as the compound ($IC_{50}$) potency, ($EC_{50}$) efficacy, and the biological half-life (of the compound), the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered. Oral administration is a preferred method of administration of the present compounds.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

In general a suitable dose for each of the above-mentioned conditions will be in the range of 0.01 to 250 mg per kilogram body weight of the recipient (e.g. a human) per day, in the range of 0.1 to 100 mg per kilogram body weight per day, in the range of 0.5 to 30 mg per kilogram body weight per day or in the range of 1.0 to 20 mg per kilogram body weight per day. Unless otherwise indicated, all weights of active ingredient are calculated as the parent compound of formula (I) or (I)'; for salts or esters thereof, the weights would be increased proportionally. The desired dose may be presented as one, two, three, four, five, six or more sub-doses administered at appropriate intervals throughout the day. In some cases the desired dose may be given on alternative days or other appropriate schedule, for example, weekly or monthly. These sub-doses may be administered in unit dosage forms, for example, containing 0.5-100 mg, 5 to 1000 mg or 50 to 500 mg, or 20 to 500 mg, or 50 to 400 mg of active ingredient per unit dosage form.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

The compounds of formula (I) or (I)' or pharmaceutically acceptable salt(s) thereof may also be used in combination with other therapeutic agents. The invention thus provides, in a further aspect, a combination comprising a compound of formula (I) or (I)' or pharmaceutically acceptable salt thereof together with one or more further therapeutic agent(s).

Compounds of the invention may be administered in combination with other therapeutic agents, for example immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (eg ribavirin and amantidine). The compositions according to the invention may also be used in combination with gene replacement therapy.

Compounds of the invention may be administered in combination with other therapeutic anti-viral agents selected from the list: interferon, pegylated interferon, ribavirin, protease inhibitors, for example, telepravir, boceprevir, BMS650032, GS9256, BI201335, IDX320 or compounds disclosed in PCT/US2010/046782; polymerase inhibitors, for example, filibuvir, VX222, GS7977, GS9190, PSI938, PSI7792, BI207127, R7128, IDX184; inhibitors of other viral proteins such as NS5a, for example daclatasvir, and NS4a or NS4b, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds. For example, combination therapy may comprise providing a compound for formula (I) or (I)' or pharmaceutically acceptable salt thereof with other anti-viral agents, such as acyclovir, famciclovir, valganciclovir and related compounds, ribavirin and related compounds, amantadine and related compounds, various interferons such as, interferon-alpha, interferon-beta, interferon-gamma and the like as well as alternative forms of interferons such as pegylated interferons.

Interferons include interferon-α, peglyated interferon-α, a combination of interferon-α and ribavirin, and a combination of interferon-α and levovirin. Interferon-α includes, but is not limited to, recombinant interferon-α2a, interferon-α 2b, a consensus interferon, and a purified interferon-α product.

The compositions and methods of the present invention feature a compound of formula (I) or (I)' and interferon. The interferon may be selected from the group consisting of interferon-α2b, peglyated interferon-α, consensus interferon, interferon-α2a, and lymphoblastoid interferon tau.

The compositions and methods of the present invention feature a compound of formula (I) or (I)' and a compound having anti-HCV activity selected from the group consisting of interleukin 2, interleukin 6, interleukin 12, a RNA, anti-sense RNA, imiquimod, ribavirin, an inosine 5'-monophosphate dehydrogenase inhibitor, amantadine and rimantadine.

When a compound of formula (I) or (I)' or pharmaceutically acceptable salt thereof is used in combination with a second therapeutic agent the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical composition and thus pharmaceutical compositions comprising a combination as defined above together with at least one pharmaceutically acceptable carrier and/or excipient comprise a further aspect of the invention.

The individual components of such combinations may be administered either sequentially or simultaneously in separate or combined pharmaceutical compositions by any convenient route.

When administration is sequential, either the HCV inhibitor or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The following non-limiting examples illustrate the present invention.

EXAMPLES

It will be appreciated by those skilled in the art that when solvents are used in reactions it is desirable to use anhydrous solvents. It is further desirable to conduct reactions under an inert atmosphere, for example under nitrogen or argon, where appropriate.

The compounds of formula (I) and (I') may be prepared by the following methods or by any method known to one skilled in the art.

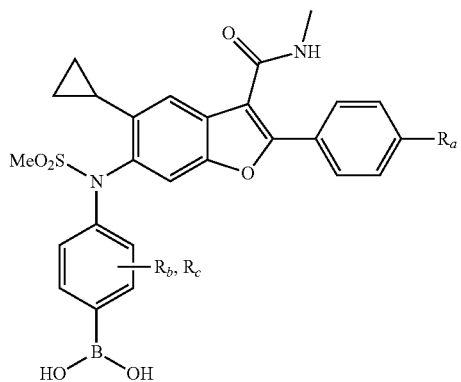

IX

-continued

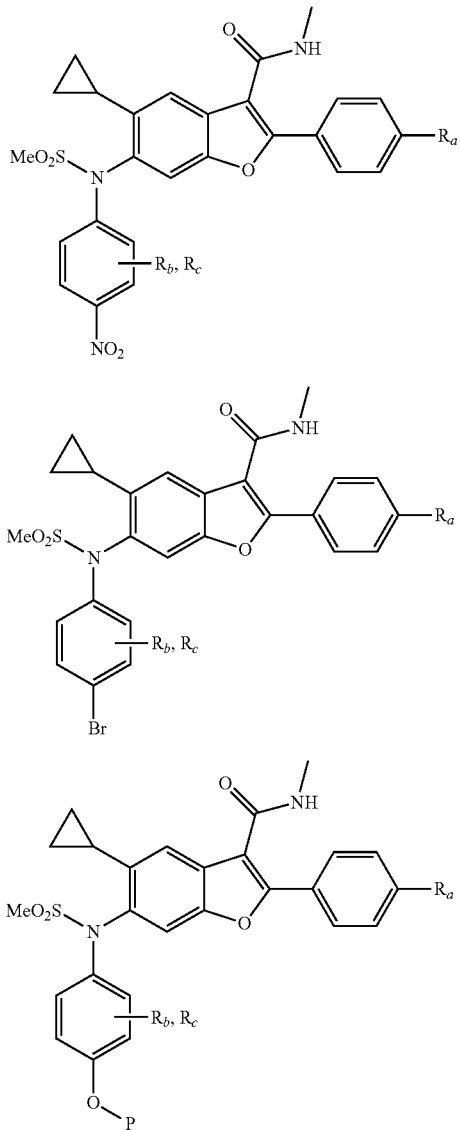

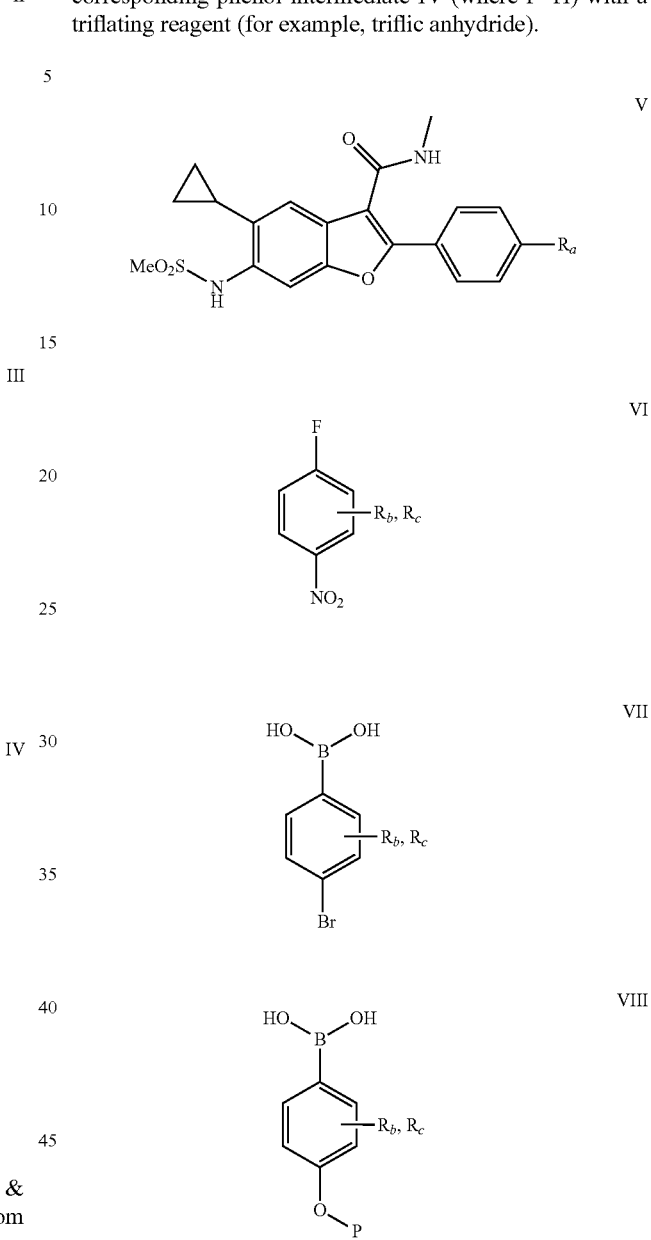

Compounds of formula (I) of type IX ($R_a$=halogen, $R_b$ & $R_c$=halogen, alkyl, alkoxy, or ring) are readily prepared from the corresponding bromide (III) compounds or corresponding triflate (IV, where P=OTf) compounds using conditions known to those skilled in the art. For example, conversion of III to the corresponding pinacol boronate can be accomplished by treatment with a catalyst (for example $PdCl_2$ (dppf)), base (for example KOAc), boron source (for example bis-pinacol diboron) in solvent (for example 1,4-dioxane) with heat (for example 80° C.). Subsequent treatment with an acid (for example HCl) in solvent mixture (for example THF/water) with a pinacol scavenger (for example polymer-supported benzeneboronic acid) or with sodium periodate affords IX. Further, those skilled in the art will recognize nitro II can be converted to the corresponding aniline using reduction conditions including a catalyst (for example 10% palladium on carbon) in a solvent (for example THF) under an atmosphere of hydrogen. Subsequent use of a Sandmeyer reaction, including an oxidant (for example sodium nitrite), an acid (for example HBr) and cuprous bromide in solvent (for example MeCN) affords III. The triflate (IV, where P=OTf) compounds can be generated by treatment of the corresponding phenol intermediate IV (where P=H) with a triflating reagent (for example, triflic anhydride).

Compounds II, III and IV are readily available from coupling of the corresponding sulfonamide V (where $R_a$=halogen) with either a nitro-fluoroarene (VI) or bromo boronic acid (VII) or phenol-protected boronic acid (VIII, where P=benzyl)). In the case of the former, direct treatment of V with a base (for example LiHMDS or potassium carbonate) in solvent (for example DMF) followed by exposure to VI gives the corresponding $SN_{AR}$ displacement products II. Additionally, treatment of sulfonamide V with an aryl boronic acid such as VII or VIII (where P=benzyl) using Chan-Lam coupling conditions, including a copper source (for example copper (II) acetate), a base (for example triethylamine), and a desiccant (for example 3 or 4 Å molecular sieves) in solvent (for example DCM) affords the corresponding bromide III or phenol-protected intermediate IV (where P=benzyl) which upon deprotection (for example via hydrogenation of the benzyl group) give the phenol intermediate IV (where P=H).

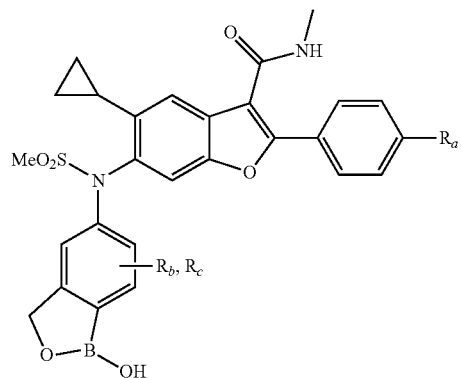

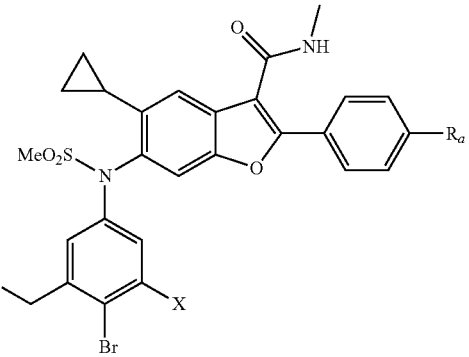

Bicyclic oxaboryl analogs such as X can be made in an analogous fashion. For example, coupling of the corresponding sulfonamide V (where Ra=halogen) with a nitro-fluoro-arene VI in the presence of a base (for example LiHMDS or potassium carbonate) in solvent (for example DMF) yields compounds such as XI. Nitro XI can be converted to the corresponding aniline XII (where X=H) using reduction conditions including a catalyst (for example 10% palladium on carbon) in a solvent (for example THF) under an atmosphere of hydrogen. The corresponding aniline XII can be converted to the bromide XIII (X=H) by those skilled in the art via a Sandmeyer reaction, wherein the aniline XII is treated with an oxidant (for example sodium nitrite), an acid (for example HBr) and cuprous bromide in solvent (for example MeCN). Alternatively, the aniline XII (where X=H) can be treated with an electrophilic halogen source (for example, N-chlorosuccinimide) in a solvent (for example, MeCN) to give the corresponding halogenated aniline XII (where X=Cl). The aniline can then be converted to the corresponding bromide XIII (where X=Cl) via the Sandmeyer reaction described previously. The ester functionality of intermediate XIII (where X=H or Cl) can be reduced to the corresponding benzylic alcohol XIV (where P=H) by a number of various reducing agents (for example, LiBH$_4$) in a solvent (for example, THF). Protection of the alcohol with any number of protecting groups (for example, -MOM) can be accomplished by those skilled in the art by treatment of the benzylic alcohol XIV (where P=H) with a base (for example, DIPEA) and a protecting group (for example, MOM-Cl) in a solvent (for example, THF) to give the MOM-protected benzylic alcohol XIV (where P=MOM). The bromide can then be converted to the corresponding boronic ester by those skilled in the art. For example, conversion of XIV (where P=MOM) to the corresponding pinacol boronate can be accomplished by treatment with a catalyst (for example PdCl$_2$(dppf)), base (for example KOAc), boron source (for example bis-pinacol diboron) in solvent (for example 1,4-dioxane) with heat (for example 80° C.). Subsequent treatment with an acid (for example HCl) in solvent (for example THF) removes both the pinacol ester and the MOM-protecting group, thereby forming the bicyclic oxaboryl analog X.

XV

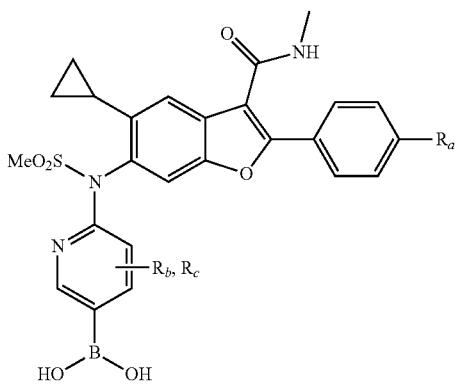

XVIII

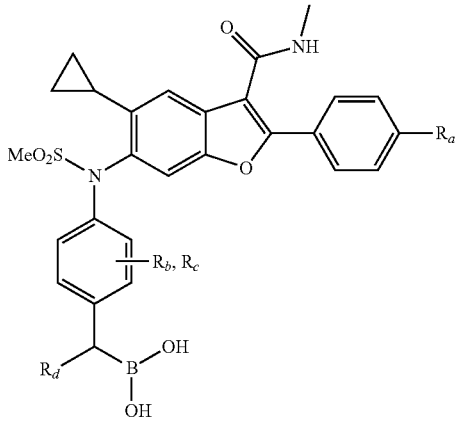

XVI

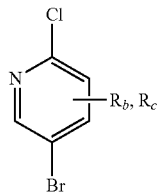

In a manner similar to that described above, compounds of type XV may be obtained directly by treatment of compounds of formula V with those of XVI in the presence of a base (for example sodium hydride or LHMDS) in solvent (for example THF). Conversion of the resulting bromide to compounds of formula XVI can be achieved in a manner analogous to the conversion of compound III to compound IX.

XVII

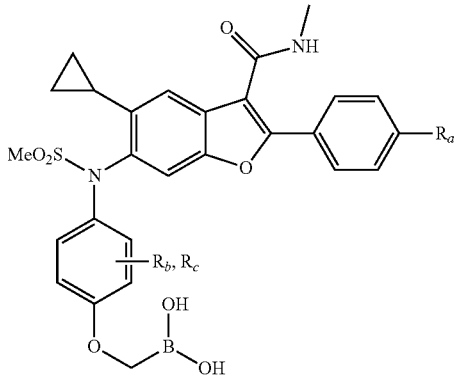

XIX

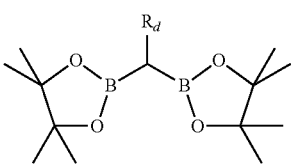

Boronic acids of type XVII are accessible via alkylation of the corresponding phenol intermediate IV (where P=H) with 2-(chloromethyl)-4,4,5,5-tetramethyl-1,3,2-dioxaborolane) in the presence of a base (for example, $K_2CO_3$) and in a suitable solvent (for example, DMF). Removal of the pinacol group with conditions described herein yields the corresponding boronic acids XVII. Those skilled in the art will recognise that benzylic boronic acids of type XVIII are accessible from the corresponding boronic esters of type IX or from the corresponding bromides of type III. For example, treatment of the appropriately protected pinacol boronic ester IX with $LiCH_2Cl$ in an appropriate solvent (for example, THF) at low temperature (for example, −78° C.) as described in the literature (for example, J. Med. Chem. 2010, 53, 7852) yields the corresponding benzylic boronic ester XVIII (where $R_d$=H). Alternatively, the corresponding benzylic boronic esters of type XVIII (where $R_d$=H) can be prepared from the appropriately substituted aryl bromides of type III via halogen-metal exchange using a suitable alkyllithium (for example, tBuLi) in a suitable solvent (for example, THF) at low temperature (for example, −78° C.) followed by the addition of 2-(chloromethyl)-4,4,5,5-tetramethyl-1,3,2-dioxaborolane). Alternatively, the corresponding benzylic boronic esters of type XVIII can be prepared from the appropriately substituted aryl bromides of type III via Pd-catalyzed cross-coupling of the aryl bromide with an appropriately substituted bis-boronic ester such XIX (where $R_d$=alkyl, benzyl) as described in the literature (for example, J. Am. Chem. Soc. 2010, 132, 11033).

XX

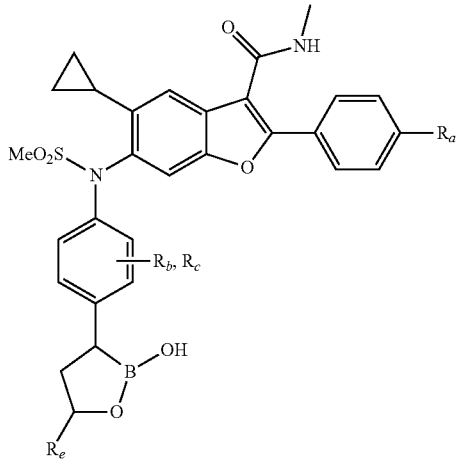

XXI

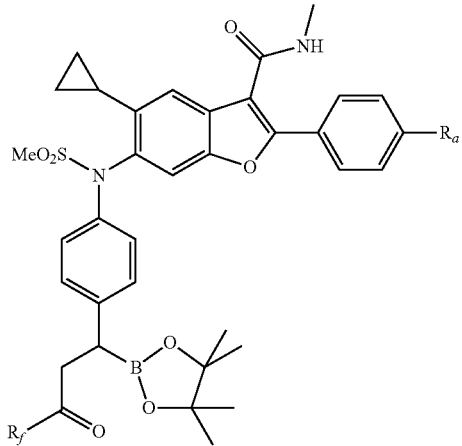

XXII

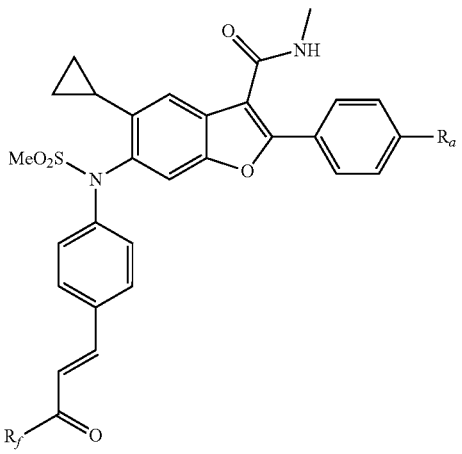

XXIII

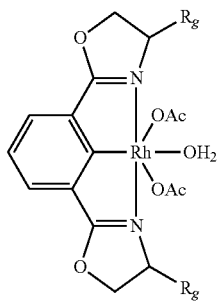

$R_g$ = iPr, sBu, Bn, Ph

Cyclic oxaboryls of type XX (where $R_e$=H, alkyl) can be prepared via multiple routes as described in the literature. For example, reaction of bis-pinacol borane ($B_2pin_2$) to α,β-unsaturated esters (for example, where $R_f$=OMe), amides (for example, where $R_f$=NMe$_2$), and ketones (for example, where $R_f$=alkyl) of type XXII in the presence of a metal catalyst (for example, CuCl or Rh(Phebox) XXIII) as described in the literature (*J. Org. Chem.* 2011, 76, 3997 or *Chem. Commun.* 2009, 5987) yields intermediates of type XXI, which upon reduction of the ester, amide, or ketone and removal of the pinacol produce the corresponding cyclic oxaboryls XX (where $R_e$=H, alkyl).

XXIV

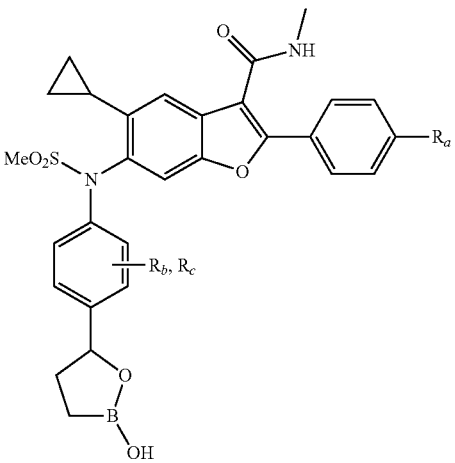

XXV

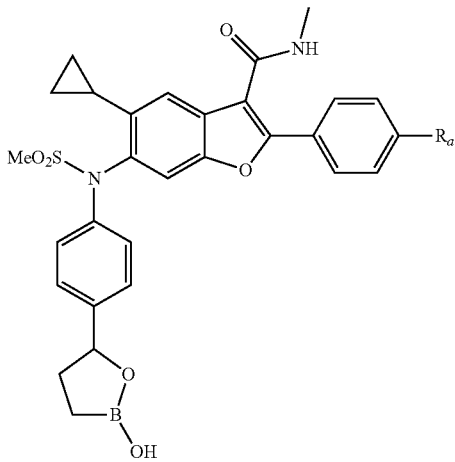

-continued

XXVI

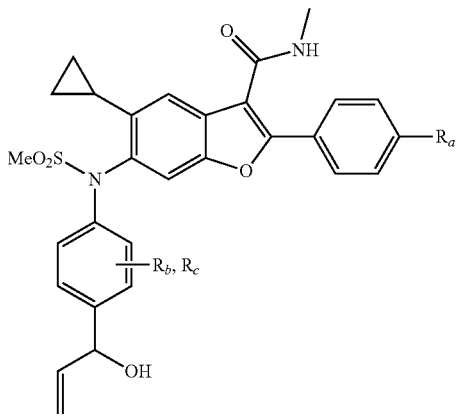

XXVII

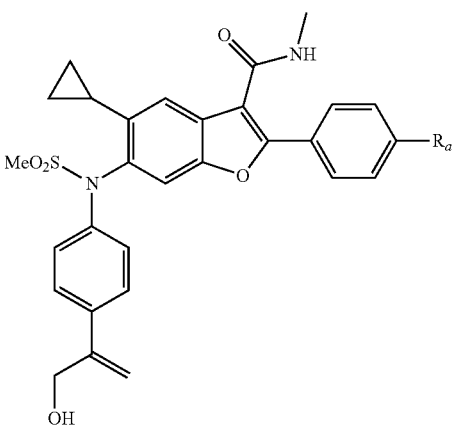

The regioisomeric cyclic oxaboryls XXIV and XXV are readily prepared via hydroboration of the corresponding alkenes (XXVI and XXVII, respectively) by standard conditions described in the literature.

Intermediate Syntheses

Intermediate 1: 2-(4-Chlorophenyl)-5-cyclopropyl-N-methyl-6-(methylsulfonamido)benzofuran-3-carboxamide

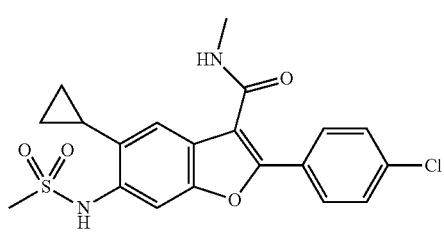 [SMILES: CNC(=O)c1c(-c2ccc(Cl)cc2)oc2cc(NS(C)(=O)=O)c(C3CC3)cc12]

Step 1: Ethyl 3-(4-chlorophenyl)-3-oxopropanoate

To a solution of 4-chlorobenzoic acid (30.0 g, 0.192 mol) in DCM (250 mL) was added oxalyl chloride (25 mL, 0.288 mol) and then DMF (0.5 mL) was added dropwise. The reaction mixture was refluxed for 2 hrs. The resulting clear yellow solution was concentrated in vacuo to afford the acid chloride as yellow liquid. TEA (67 mL) was added to a solution of ethyl potassium malonate (41 g, 0.241 mol) in acetonitrile (537 mL). Upon cooling in an ice-salt bath, $MgCl_2$ (27.4 g, 0.288 mol) was added and the resulting mixture was stirred at that temperature for 3 hrs. The acid chloride (prepared as described above) was added and the reaction mixture was warmed to ambient temperature and stirred overnight. The mixture was cooled in an ice bath and 2N HCl (600 mL) was carefully added. The mixture was stirred in the ice bath for 1.5 hrs then transferred to a separatory funnel and extracted with ethyl acetate (3×200 mL). The combined organic layers were washed with saturated sodium bicarbonate (450 mL), brine (250 mL), dried over anhydrous sodium sulfate, filtered, and concentrated in vacuo to afford the crude product ethyl 3-(4-chlorophenyl)-3-oxopropanoate (48.6 g) which was used without purification.

Step 2: Ethyl 2-(4-chlorophenyl)-5-hydroxybenzofuran-3-carboxylate

Zinc chloride (28.3 g, 0.207 mol) was stirred in anhydrous ethanol (45 mL) then heated to 95° C. (reflux) under nitrogen atmosphere using oven dried glassware. Ethyl 4-chlorobenzoylacetate (44 g, 0.194 mol) was added as a single portion followed by dropwise addition of a solution of benzoquinone (22.6 g, 0.21 mol) in anhydrous MTBE (500 mL) over 2 hours. This was performed with a simultaneous distillation of MTBE from the reaction mixture such that the reaction volume remained approximately constant. A bath temperature of 145-155° C. and an internal temperature of 75-95° C. maintained throughout most of the addition. Halfway through the addition more anhydrous ethanol (45 mL) was added because the reaction mixture became thick and a loss of some of the original volume of ethanol through the distillation was suspected. After addition was complete, heating continued for 30 minutes. The reaction mixture was cooled to room temperature and partitioned between water (100 mL) and EtOAc (250 mL). The insoluble solids were removed by filtration of the biphasic solution and the organic layer was then separated, washed with more water, dried and evaporated under vacuum. The residual brown solid was slurried in warm dichloromethane and the mixture cooled to room temperature and cooled further by refrigeration overnight. The tan solid was filtered from the dark brown solution and washed with a small volume of DCM and dried under vacuum to give ethyl 2-(4-chlorophenyl)-5-hydroxybenzofuran-3-carboxylate (27 g, 44%).

Step 3: Ethyl 2-(4-chlorophenyl)-5-isopropoxybenzofuran-3-carboxylate

Ethyl 2-(4-chlorophenyl)-5-hydroxybenzofuran-3-carboxylate (26 g, 0.051 mol) in NMP (160 mL) was added isopropyl bromide (15 mL), then cesium carbonate (33 g, 0.101 mol) was added. The reaction mixture was stirred in a 60° C. oil bath for 20 hrs then cooled to ambient temperature. The reaction mixture was treated with 5% ammonium solution and stirred for 15 min. This mixture was then diluted with water and extracted with hexane. The organic layer was washed with water, dried with anhydrous sodium sulfate, filtered, and concentrated under reduced pressure to give ethyl 2-(4-chlorophenyl)-5-isopropoxybenzofuran-3-carboxylate (15 g, 82%).

Step 4: Ethyl 2-(4-chlorophenyl)-5-isopropoxy-6-nitrobenzofuran-3-carboxylate

Ethyl 2-(4-chlorophenyl)-5-isopropoxybenzofuran-3-carboxylate 4 (30 g, 0.084 mol) was dissolved in chloroform (75 mL) and the resulting solution was cooled in an ice bath. Nitric acid (55 mL) was also dissolved in chloroform (75 mL) and cooled in an ice bath. The acid solution was added dropwise to the solution of ethyl 2-(4-chlorophenyl)-5-isopropoxybenzofuran-3-carboxylate over 1 hour, and the reaction mixture was then stirred at 0° C. for 1.5 hrs. The reaction mixture was then diluted with water (60 mL) and the layers were separated. The organic layer was dried with anhydrous sodium sulfate, filtered, and concentrated under reduced pressure to give a brown oil which was purified by column chromatography (5/1 PE/EA) to afford ethyl 2-(4-chlorophenyl)-5-isopropoxy-6-nitrobenzofuran-3-carboxylate as a brown solid (11 g, 32%).

Step 5: Ethyl 2-(4-chlorophenyl)-5-hydroxy-6-nitrobenzofuran-3-carboxylate

Ethyl 2-(4-chlorophenyl)-5-isopropoxy-6-nitrobenzofuran-3-carboxylate (11 g, 27.2 mmol) was dissolved in anhydrous DCM (150 mL) and cooled in an ice bath under an atmosphere of nitrogen. Boron trichloride (41 mL, 41.0 mmol) was added over ~20 minutes. After the reaction was complete, the reaction mixture was quenched by pouring into an ice/water mixture. The mixture was extracted with DCM, and the combined organic layers were dried over anhydrous sodium sulfate, filtered, and concentrated under vacuum to give ethyl 2-(4-chlorophenyl)-5-hydroxy-6-nitrobenzofuran-3-carboxylate (10.2 g, 84%).

Step 6: Ethyl-2-(4-chlorophenyl)-6-nitro-5-(trifluoromethylsulfonyloxy)benzofuran-3-carboxylate To a solution of ethyl 2-(4-chlorophenyl)-5-hydroxy-6-nitrobenzofuran-3-carboxylate (10.2 g, 22.9 mmol) and DMAP (0.289 g, 2.3 mmol) in anhydrous DCM (300 mL) and anhydrous TEA (4.8 mL) in an ice bath under nitrogen was added trifluoromethane sulfonic anhydride (5.62 mL, 34 mmol). The reaction mixture was stirred under nitrogen at 0° C. for 30 min then quenched at 0° C. with water (200 mL) and extracted with DCM (3×200 mL). The combined organic layers were washed with water (3×600 mL), 2N HCl (2×300 mL), water (300 mL), dried with anhydrous sodium sulfate, filtered and concentrated under reduced pressure to afford ethyl 2-(4-chlorophenyl)-6-nitro-5-(trifluoromethylsulfonyloxy)benzofuran-3-carboxylate (10 g, 80%) as a yellow solid that was used without further purification.

Step 7: Ethyl 2-(4-chlorophenyl)-5-cyclopropyl-6-nitrobenzofuran-3-carboxylate A mixture of 2-(4-chlorophenyl)-6-nitro-5-(trifluoromethylsulfonyloxy)benzofuran-3-carboxylate (10 g, 18 mmol), KF (4.64 g, 79.9 mmol), NaBr (2.48 g, 24 mmol), cyclopropylboronic acid (3.2 g, 37 mmol), and Pd(Ph$_3$P)$_4$ (1.33 g, 1.15 mmol) were added toluene (130 mL) and water (2.8 mL). The reaction flask was evacuated for ~3 minutes then filled with nitrogen. The reaction mixture was refluxed under nitrogen for 20 hrs then cooled to ambient temperature. The reaction mixture was diluted with EtOAc (150 mL), washed with water (3×200 mL), brine (200 mL), dried with anhydrous sodium sulfate, decanted, and concentrated under reduced pressure. The residue was purified by column chromatography (petroleum ether/ethyl acetate=30/1-10/1) to afford ethyl 2-(4-chlorophenyl)-5-cyclopropyl-6-nitrobenzofuran-3-carboxylate as a yellow solid (7.9 g, 99%).

Step 8: Ethyl 6-amino-2-(4-chlorophenyl)-5-cyclopropylbenzofuran-3-carboxylate To a solution of ethyl 2-(4-chlorophenyl)-5-cyclopropyl-6-nitrobenzofuran-3-carboxylate (8 g, 18.2 mmol) in ethyl acetate (450 mL) was added 10% palladium on carbonate (1.83 g), 1N HCl solution (2.5 mL), and stirred with under 0.4 MPa of hydrogen at room temperature for 8 hrs. The reaction mixture was filtered through celite and the filtrate was evaporated under vacuum to give ethyl 6-amino-2-(4-chlorophenyl)-5-cyclopropylbenzofuran-3-carboxylate as a brown solid (7.4 g, 99%).

Step 9: Ethyl 2-(4-chlorophenyl)-5-cyclopropyl-6-(N-(methylsulfonylmethyl)methylsulfonamido)benzofuran-3-carboxylate To a solution of ethyl 6-amino-2-(4-chlorophenyl)-5-cyclopropylbenzofuran-3-carboxylate (7.4 g, 18.06 mmol) in dry dichloromethane (170 mL) at −15° C. under N$_2$ atmosphere was added dry TEA (6.73 mL, 45.15 mmol) and then methanesulfonyl chloride (4.91 mL, 63.2 mmol) dropwise. The stirred solution was warmed to room temperature and stirred for 2 hours. The reaction mixture was diluted with water (100 mL) and extracted with DCM (3×150 mL). The organic layers were combined, dried with Na$_2$SO$_4$, filtered and evaporated under vacuum to afford ethyl 2-(4-chlorophenyl)-5-cyclopropyl-6-(N-(methylsulfonylmethyl)methylsulfonamido)benzofuran-3-carboxylate (9.2 g, 99%).

Step 10: 5-Cyclopropyl-2-(4-chlorophenyl)-6-(methylsulfonamido)benzofuran-3-carboxylic acid Potassium hydroxide (15.1 g, 270 mmol) was added to a solution of the ethyl 2-(4-chlorophenyl)-5-cyclopropyl-6-(N-(methylsulfonylmethyl)methylsulfonamido)benzofuran-3-carboxylate in ethanol (64 mL) and water (32 mL) under nitrogen atmosphere. The reaction was refluxed for 1 hour and then concentrated in vacuo. The remaining solid was dissolved in water and the solution was acidified with 1N HCl (250 mL) until a precipitate formed. The solid was filtered and then dried to afford 5-cyclopropyl-2-(4-chlorophenyl)-6-(methylsulfonamido)benzofuran-3-carboxylic acid (8.7 g, quantitative yield).

Step 11: 2-(4-Chlorophenyl)-5-cyclopropyl-N-methyl-6-(methylsulfonamido)benzofuran-3-carboxamide To a solution of 5-cyclopropyl-2-(4-chlorophenyl)-6-(methylsulfonamido)benzofuran-3-carboxylic acid (5 g, 11.52 mmol) in dry DMF (30 mL) was added DIPEA (3.3 g, 25.34 mmol) and HATU (5.15 g, 13.5 mmol) at 20° C. After 15 minutes, 2M Methylamine in THF (23.04 mL, 46.08 mmol) was added dropwise and the mixture was stirred for another 2 hours before water (60 mL) was added. The mixture was extracted with EA (3×200 mL), washed with water (2×200 mL), dried and concentrated to afford 2-(4-Chlorophenyl)-5-cyclopropyl-N-methyl-6-(methylsulfonamido)benzofuran-3-carboxamide as a brown solid (4.7 g, 97%). $^1$H NMR (400 MHz, DMSO-d$_6$) δ ppm 9.32 (br. s., 1H) 8.45 (q, 1H) 7.90 (d, 2H) 7.53-7.64 (m, 3H) 7.16 (s, 1H) 3.06 (s, 3H) 2.83 (d, 3H)

2.21-2.37 (m, 1H) 0.94-1.05 (m, 2H) 0.64-0.73 (m, 2H). LCMS (m/z, ES+)=419 (M+H+).

Intermediate 2: 5-Cyclopropyl-2-(4-fluorophenyl)-N-methyl-6-(methylsulfonamido)benzofuran-3-carboxamide

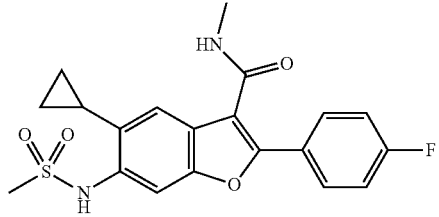 [SMILES: CNC(=O)c1c(-c2ccc(F)cc2)oc2cc(NS(C)(=O)=O)c(C3CC3)cc12]

Step 1: Methyl 2-(4-fluorophenyl)-5-hydroxy-1-benzofuran-3-carboxylate

Using oven dried glassware and under an atmosphere of nitrogen, anhydrous zinc chloride (25 g, 183 mmol) was stirred in anhydrous methanol (60 mL) then heated to a 75° C. internal temperature. Methyl 4-fluorobenzoylacetate (39.6 g, 202 mmol) was added as a single portion followed by dropwise addition of a solution of p-benzoquinone (19.83 g, 183 mmol) in anhydrous diethyl ether (500 mL) over 4 hours. This was performed with a simultaneous distillation of ether from the reaction mixture such that the reaction volume remained approximately constant (a bath temperature of 140° C. maintained an internal temperature initially at 75° C. then gradually increasing to a maximum of 115° C.). 2.5 hours after the start of the benzoquinone addition, more methanol (20 mL) was added to facilitate stirring. After addition of benzoquinone was complete, heating of the reaction mixture at 100° C. (internal) continued for 1 hour. The reaction mixture was cooled to room temperature and partitioned between water (500 mL) and ethyl acetate (800 mL). The insoluble solids were removed from the biphasic solution by filtration and the organic layer was then separated, dried ($Na_2SO_4$), filtered and evaporated under vacuum. The brown residue was slurried in warm dichloromethane (~225 mL) and the mixture was left to stand in a refrigerator for 18 hours. The resulting solids were filtered from the dark brown solution, washed with a small volume of dichloromethane then dried under vacuum to give Methyl 2-(4-fluorophenyl)-5-hydroxy-1-benzofuran-3-carboxylate. LCMS (m/z, ES+)=285 (M−1).

Step 2: Methyl 2-(4-fluorophenyl)-5-[(1-methylethyl)oxy]-1-benzofuran-3-carboxylate A mixture of methyl 2-(4-fluorophenyl)-5-hydroxy-1-benzofuran-3-carboxylate (18.86 g, 65.9 mmol), isopropyl bromide (24.74 mL, 264 mmol) and cesium carbonate (42.9 g, 132 mmol) in dry N-Methyl-2-pyrrolidone (191 mL) was stirred at 60° C. under nitrogen for 20 hours. The resultant thick suspension was allowed to cool to room temperature and then 7% aqueous ammonia solution (200 mL) was added with rapid stirring. This mixture was extracted with heptane (700 mL) and then the aqueous phase was separated off. Ethyl acetate (~100 mL) was added to the organic phase and the resultant mixture was shaken and then dried over $Na_2SO_4$ and evaporated to give a brown oil which crystallized on standing overnight. This material was recrystallized from hot methanol and the solid was collected by filtration, washed with methanol and finally dried under vacuum to give methyl 2-(4-fluorophenyl)-5-[(1-methylethyl)oxy]-1-benzofuran-3-carboxylate. LCMS (m/z, ES+)=329 (M+1). The mother liquors from the first recrystallization were crystallized a second time to give an additional batch of methyl 2-(4-fluorophenyl)-5-[(1-methylethyl)oxy]-1-benzofuran-3-carboxylate.

Step 3: Methyl 2-(4-fluorophenyl)-5-[(1-methylethyl)oxy]-6-nitro-1-benzofuran-3-carboxylate To a solution of methyl 2-(4-fluorophenyl)-5-[(1-methylethyl)oxy]-1-benzofuran-3-carboxylate (6.16 g, 18.76 mmol) in chloroform (22 mL) at −15° C. was added dropwise a cold solution of 70% nitric acid (11 mL, 172 mmol) in chloroform (22 mL). After stirring at 0° C. for 1 hour, the reaction mixture was washed with water (50 mL) and the organic phase was separated by hydrophobic filter tube then evaporated under vacuum to afford a brown solid. The solid was triturated in methyl tert-butyl ether (25 mL) and the resulting pale yellow powder was filtered off, washed with heptane and dried under vacuum to give methyl 2-(4-fluorophenyl)-5-[(1-methylethyl)oxy]-6-nitro-1-benzofuran-3-carboxylate. LCMS (m/z, ES+)=764 (2M+$NH_4$)+.

Step 4: Methyl 2-(4-fluorophenyl)-5-hydroxy-6-nitro-1-benzofuran-3-carboxylate

To a stirred solution of methyl 2-(4-fluorophenyl)-5-[(1-methylethyl)oxy]-6-nitro-1-benzofuran-3-carboxylate (5.237 g, 14.03 mmol) in dry dichloromethane (70 mL) at −15° C., under an atmosphere of nitrogen, was added a 1M solution of boron trichloride in dichloromethane (23.85 mL, 23.85 mmol) over 30 minutes using a syringe pump. The dark brown-red reaction mixture was poured over ice (~250 mL). The ice was allowed to melt and the mixture extracted with dichloromethane (~450 mL). The organic phase was separated by hydrophobic filter tube and evaporated under vacuum to give the methyl 2-(4-fluorophenyl)-5-hydroxy-6-nitro-1-benzofuran-3-carboxylate. $^1$H NMR ($d_6$-DMSO): δ 10.97 (1H, br. s), 8.34 (1H, s), 8.07 (2H, dd), 7.67 (1H, s), 7.43 (2H, t), 3.86 (3H, s).

Step 5: Methyl 2-(4-fluorophenyl)-6-nitro-5-{[(trifluoromethyl)sulfonyl]oxy}-1-benzofuran-3-carboxylate To an ice-cooled stirred mixture of methyl 2-(4-fluorophenyl)-5-hydroxy-6-nitro-1-benzofuran-3-carboxylate (4.915 g, 14.84 mmol) and 4-(dimethylamino)pyridine (0.181 g, 1.484 mmol) in anhydrous dichloromethane (130 mL) under nitrogen, was added triethylamine (3.10 mL, 22.26 mmol) followed by trifluoromethanesulfonic anhydride (3.76 mL, 22.26 mmol). After 50 minutes at 0° C., water was added and the organic layer was separated. The aqueous phase was extracted with more dichloromethane and the combined organics were washed with 2M HCl and water. The organics were dried by hydrophobic filter tube and evaporated to give the Methyl 2-(4-fluorophenyl)-6-nitro-5-{[(trifluoromethyl)sulfonyl]oxy}-1-benzofuran-3-carboxylate. LCMS (m/z, ES+)=481 (M+$NH_4$)+.

Step 6: Methyl 5-cyclopropyl-2-(4-fluorophenyl)-6-nitro-1-benzofuran-3-carboxylate Methyl 2-(4-fluorophenyl)-6-nitro-5-{[(trifluoromethyl)sulfonyl]oxy}-1-benzofuran-3-carboxylate (7.12 g, 15.37 mmol), cyclopropylboronic acid (2.19 g, 25.5 mmol), potassium fluoride (3.26 g, 56.1 mmol), sodium bromide (1.75 g, 17.01 mmol) and tetrakis(triphenylphosphine)palladium(0) (0.85 g, 0.736 mmol) were stirred together under nitrogen in a mixture of toluene (90 mL) and water (2.25 mL) and heated at 100° C. for 18 hours. The reaction mixture was cooled, diluted with ethyl acetate and washed with water. The organic phase was separated, dried by hydrophobic filter tube and evaporated under vacuum. The residue was purified by flash chromatography, eluting over silica gel with a gradient of 0-5% ethyl acetate in cyclohexane. Product containing fractions were evaporated under vacuum to give the methyl 5-cyclopropyl-2-(4-fluorophenyl)-6-nitro-1-benzofuran-3-carboxylate. LCMS (m/z, ES$^+$)=728 (2M+NH$_4$)$^+$.

Step 7: Methyl 6-amino-5-cyclopropyl-2-(4-fluorophenyl)-1-benzofuran-3-carboxylate A solution of methyl 5-cyclopropyl-2-(4-fluorophenyl)-6-nitro-1-benzofuran-3-carboxylate (3.175 g, 8.94 mmol) in ethyl acetate (250 mL) containing 2M HCl (17 drops) was stirred with 10% palladium on carbon (0.951 g, 0.894 mmol) under an atmosphere of hydrogen at 21° C. for 16 hours. The reaction mixture was filtered through celite and the filtrate was evaporated under vacuum to give a dark green solid. This was dissolved in dichloromethane, washed with sodium bicarbonate solution, separated by hydrophobic frit, then evaporated to dryness and purified by flash chromatography, eluting over silica gel with a gradient of 0-30% ethyl acetate in cyclohexane. Appropriate fractions were combined and evaporated under vacuum to give the methyl 6-amino-5-cyclopropyl-2-(4-fluorophenyl)-1-benzofuran-3-carboxylate. LCMS (m/z, ES$^+$)=326 (M+H+).

Step 8: Methyl 6-[4bis(methylsulfonyl)amino]-5-cyclopropyl-2-(4-fluorophenyl)-1-benzofuran-3-carboxylate A solution of methyl 6-amino-5-cyclopropyl-2-(4-fluorophenyl)-1-benzofuran-3-carboxylate (1.96 g, 6.02 mmol) and triethylamine (2.52 mL, 18.07 mmol) in dry dichloromethane (40 mL) was cooled (ice bath) to 0° C., then treated with methanesulfonyl chloride (1.174 mL, 15.06 mmol). The reaction was stirred at 0° C. (ice bath) for 2 hours. Water (100 mL) was added and the organics extracted 3 times with dichloromethane, dried using an hydrophobic frit and evaporated to dryness to give the methyl 6-[4bis(methylsulfonyl)amino]-5-cyclopropyl-2-(4-fluorophenyl)-1-benzofuran-3-carboxylate. LCMS (m/z, ES$^+$)=482 (M+H+).

Step 9: 5-Cyclopropyl-2-(4-fluorophenyl)-6-[(methylsulfonyl)amino]-1-benzofuran-3-carboxylic acid A suspension of methyl 6-[4bis(methylsulfonyl)amino]-5-cyclopropyl-2-(4-fluorophenyl)-1-benzofuran-3-carboxylate (2.88 g, 5.98 mmol) in ethanol (50 mL) and water (25 mL) was treated with potassium hydroxide (6.71 g, 120 mmol) and heated at reflux for 1 hour (the suspension went into solution upon heating). The reaction was concentrated under vacuum, water (100 mL) was added and the solution acidified with 2M HCl (50 mL). The resulting precipitate was filtered, washed with 0.5 M HCl, then dissolved in methanol. This solution was evaporated to dryness and azeotroped twice with toluene to give 5-Cyclopropyl-2-(4-fluorophenyl)-6-[(methylsulfonyl)amino]-1-benzofuran-3-carboxylic acid. LCMS (m/z, ES$^+$)=390 (M+H+).

Step 10: 5-Cyclopropyl-2-(4-fluorophenyl)-N-methyl-6-(methylsulfonamido)benzofuran-3-carboxamide A solution of 5-cyclopropyl-2-(4-fluorophenyl)-6-[(methylsulfonyl)amino]-1-benzofuran-3-carboxylic acid (2.52 g, 6.47 mmol), HATU (2.95 g, 7.77 mmol) and triethylamine (1.984 mL, 14.24 mmol) in dry dichloromethane (100 mL) was stirred at room temperature for 1 hour, then treated with methylamine (16.18 mL, 32.4 mmol). The solution was stirred at room temperature under nitrogen for 4 hours, during which time a precipitate formed. The reaction was diluted with dichloromethane (300 mL) and sodium bicarbonate solution (200 mL) and stirred for 10 minutes. The layers were separated and the aqueous layer extracted with further dichloromethane (150 mL). The combined organics were washed with brine (200 mL), dried using a hydrophobic frit and evaporated to dryness to give an off-white solid. The crude product was purified by flash chromatography (eluting with 0-100% ethyl acetate/cyclohexane followed by 10% methanol/dichloromethane) to give a white solid. The solid was dissolved in hot methanol-chloroform (10% v/v), preabsorped onto silica gel and purified by flash chromatography (0-10% methanol/dichloromethane) to give the 5-cyclopropyl-2-(4-fluorophenyl)-N-methyl-6-[(methylsulfonyl)amino]-1-benzofuran-3-carboxamide. $^1$H NMR (400 MHz, DMSO-d$_6$) δ ppm 9.30 (br s, 1H) 8.42 (q, 1H) 7.88-7.98 (m, 2H) 7.60 (s, 1H) 7.37 (t, 2H) 7.16 (s, 1H) 3.06 (s, 3H) 2.83 (d, 3H) 2.23-2.36 (m, 1H) 0.93-1.05 (m, 2H) 0.65-0.74 (m, 2H). LCMS (m/z, ES$^+$)=403 (M+H+).

Example 1

(2-Chloro-4-(N-(5-cyclopropyl-2-(4-fluorophenyl)-3-(methylcarbamoyl)benzofuran-6-yl)methylsulfonamido)phenyl)boronic acid

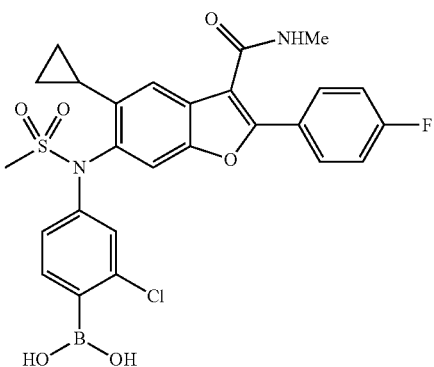 [SMILES: CNC(=O)c1c(-c2ccc(F)cc2)oc2cc(N(c3ccc(B(O)O)c(Cl)c3)S(C)(=O)=O)c(C3CC3)cc12]

Step 1: 6-(N-(3-Chloro-4-nitrophenyl)methylsulfonamido)-5-cyclopropyl-2-(4-fluorophenyl)-N-methylbenzofuran-3-carboxamide A mixture of 5-cyclopropyl-2-(4-fluorophenyl)-N-methyl-6-(methylsulfonamido)benzofuran-3-carboxamide (12.5 g, 31.1 mmol), 2-chloro-4-fluoronitrobenzene (10.9 g, 62.1 mmol) and potassium carbonate (12.9 g, 93.0 mmol) in 130 mL of 4:1 DME/water in a sealed flask was heated to 100° C. with stirring. An identical 12.5 g scale reaction was set up in a second sealed vessel. The reaction vessels were maintained at 100° C. for 70 hours, cooled to RT, and stirred for an additional 18 hours. The combined reaction mixtures were partitioned between EtOAc (300 mL) and water (600 mL), and the phases separated. The aqueous solution was extracted with two additional 150 mL portions of EtOAc. The combined EtOAc solutions were washed with half saturated brine (1×), saturated brine (1×), dried over sodium sulfate and concentrated to dryness at reduced pressure. The resulting yellow-brown solid was recrystallized from EtOAc/ether to give the title compound (22.3 g, 64%) as an off-white solid. LCMS (m/z, ES$^+$)=558 (M+H+).

Step 2: 6-(N-(4-Amino-3-chlorophenyl)methylsulfonamido)-5-cyclopropyl-2-(4-fluorophenyl)-N-methylbenzofuran-3-carboxamide A solution of 6-(N-(3-chloro-4-nitrophenyl)methylsulfonamido)-5-cyclopropyl-2-(4-fluorophenyl)-N-methylbenzofuran-3-carboxamide (11.0 g, 19.7 mmol) in 1:1 THF/MeOH (75 mL) was subjected to hydrogenation at 40 psi in the presence of 5% sulfided platinum on carbon (0.560 g). After 4 hours an additional portion of catalyst was added (0.250 g). After another 16 hours the reaction vessel was purged with nitrogen, catalyst removed by filtration through celite, and the filtrate concentrated to dryness at reduced pressure. The residue was recrystallized from hexane/EtOAc to afford the title compound (10.3 g, 99%) as a white solid. LCMS (m/z, ES$^+$)=528 (M+H+).

Step 3: 6-(N-(4-Bromo-3-chlorophenyl)methylsulfonamido)-5-cyclopropyl-2-(4-fluorophenyl)-N-methylbenzofuran-3-carboxamide To a 1 L 3-necked flask equipped with a mechanical stirrer was added 6-(N-(4-amino-3-chlorophenyl)methylsulfonamido)-5-cyclopropyl-2-(4-fluorophenyl)-N-methylbenzofuran-3-carboxamide (10.0 g, 18.9 mmol) followed by acetonitrile (200 mL) and then 48% aqueous HBr (200 mL). A thick, lumpy suspension resulted which was stirred vigorously for 30 minutes to afford a more uniform suspension. The reaction vessel was cooled in an ice water bath for 30 minutes and the mixture treated with a solution of sodium nitrite (1.96 g, 28.4 mmol) in water (20 mL) via addition funnel over 5 minutes. The resulting yellow suspension was stirred in the ice bath for 1.5 hours and then treated with CuBr (4.1 g, 28.4 mmol) in small portions over 5 minutes. This afforded a dark brown solution that was warmed to 60° C. (internal temperature) with continued stirring. After 40 minutes at elevated temperature the mixture was cooled to RT and poured into a rapidly stirred mixture of 5% aqueous sodium bisulfite (600 mL) and EtOAc (800 mL). The phases were separated and the aqueous solution extracted with two additional 150 mL portions of EtOAc. The combined EtOAc solutions were washed with 5% aqueous sodium bisulfite (2×150 mL), saturated aqueous sodium bicarbonate (2×300 mL), saturated brine (1×200 mL), dried over sodium sulfate and concentrated to dryness at reduced pressure to give a yellow foam. This material was subjected to flash chromatography (silica gel, gradient from 9:1 hexane/EtOAc to EtOAc). During concentration of the pure fractions a white solid crystallized out. After concentrating down to a thick suspension the mixture was diluted with 150 mL of hexane and the mixture stirred at RT overnight. The solid was collected by filtration in a medium fritted funnel and dried in vacuo to afford the title compound (8.55 g, 76%) as a white crystalline solid. LCMS (m/z, ES$^+$)=591, 593 (M+H+).

Step 4: (2-Chloro-4-(N-(5-cyclopropyl-2-(4-fluorophenyl)-3-(methylcarbamoyl)benzofuran-6-yl)methylsulfonamido)phenyl)boronic acid To a 350 mL screw capped flask equipped with a magnetic stirrer was added 6-(N-(4-bromo-3-chlorophenyl)methylsulfonamido)-5-cyclopropyl-2-(4-fluorophenyl)-N-methylbenzofuran-3-carboxamide (8.54 g, 14.4 mmol), bis(pinacolato)diboron (18.3 g, 72.1 mmol), potassium acetate (7.08 g, 72.1 mmol), Pd(II)(dppf)Cl$_2$ dichloromethane complex (0.589 g, 0.721 mmol) and anhydrous 1,4-dioxane (150 mL). The mixture was sparged with nitrogen for 10 minutes. The vessel was sealed and heated in an 80° C. oil bath with stirring. After 4 hours the mixture was cooled to RT and diluted with EtOAc (400 mL). The resulting black solution was washed with water (2×), saturated brine (1×), and dried over sodium sulfate. While stirring with sodium sulfate, celite was added to facilitate removal of the insoluble black material that remained suspended in solution. The mixture was filtered through a medium frit to afford a golden-brown filtrate that was concentrated to dryness at reduced pressure. The residue was dissolved in 300 mL of THF and the resulting solution cooled in an ice water bath. The solution was treated with 1N aqueous HCl (120 mL) followed by sodium periodate (46.3 g, 216 mmol). The mixture was stirred at 0° C. for 10 minutes and then allowed to warm to RT. After 18 hours the mixture was partitioned between water and EtOAc and the phases separated. The aqueous solution was extracted with EtOAc (2×). The combined EtOAc solutions were washed with 5% aqueous sodium bisulfite (4×), saturated brine (2×), dried over sodium sulfate and concentrated to dryness at reduced pressure. The residue was subjected to flash chromatography (silica gel, 2-part gradient: DCM to EtOAc over 15 minutes, then switch solvents to A=9:1 DCM/MeOH, B=DCM; gradient from 100% B to 65% A over 4 minutes, then 65% A isocratic for 15 minutes) to give a light tan foam (7.28 g). This material was dissolved in acetonitrile (75 mL) and the solution stirred with rapid dropwise addition of 0.25 N aqueous HCl (175 mL) over a 20 minute period. A white suspension was produced which was stirred at RT. After 2 hours the solid was collected by filtration in a medium fritted funnel. The filter cake was washed with water (2×), suction air dried for 30 minutes, and then dried in vacuo overnight to afford the title compound (5.90 g, 74%) as a white solid. $^1$H NMR (400 MHz, METHANOL-d$_4$) δ ppm 7.90-7.97 (m, 2H) 7.85 (s, 1H) 7.29-7.41 (m, 4H) 7.26 (t, 2H) 3.34 (s, 3H) 2.95 (s, 3H) 2.07-2.17 (m, 1H) 0.69-1.08 (m, 3H) 0.49 (br s, 1H). LCMS (m/z, ES$^+$)=557 (M+H+).

Example 2

(2-Chloro-4-(N-(2-(4-chlorophenyl)-5-cyclopropyl-3-(methylcarbamoyl)benzofuran-6-yl)methylsulfonamido)phenyl)boronic acid

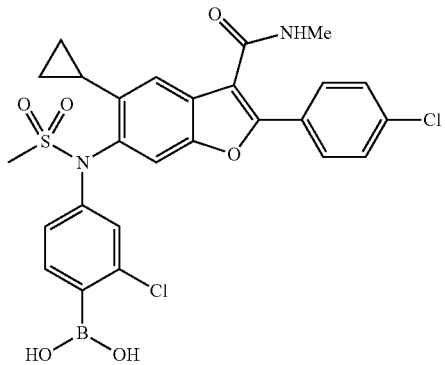 [SMILES: CNC(=O)c1c(-c2ccc(Cl)cc2)oc2cc(N(c3ccc(B(O)O)c(Cl)c3)S(C)(=O)=O)c(C3CC3)cc12]

Step 1: 6-(N-(3-Chloro-4-nitrophenyl)methylsulfonamido)-2-(4-chlorophenyl)-5-cyclopropyl-N-methylbenzofuran-3-carboxamide A mixture of 2-(4-chlorophenyl)-5-cyclopropyl-N-methyl-6-(methylsulfonamido)benzofuran-3-carboxamide (2.00 g, 4.77 mmol), 2-choro-4-fluoronitrobenzene (1.68 g, 9.55 mmol), and potassium carbonate (1.98 g, 14.3 mmol) in 4:1 DME/water (20 mL) in a sealed vessel was heated to 100° C. with stirring. After 18 hours the mixture was treated with an additional 2.00 g portion of potassium carbonate, heated at 100° C. for another 15 hours, and then stirred at RT for 3 days. The mixture was partitioned between EtOAc and water. After separating the phases, the aqueous portion was extracted with two additional portions of EtOAc. The combined EtOAc solutions were washed with water (2×), brine (1×), dried over sodium sulfate and concentrated to dryness at reduced pressure. The crude material was subjected to flash chromatography (silica gel, gradient from DCM to 7:3 DCM/EtOAc) to afford a tacky, yellow foam. This material was crystallized from hexane/EtOAc to give the title compound (1.78 g, 65%) as a light yellow solid. LCMS (m/z, ES$^+$)=574 (M+H+).

Step 2: 6-(N-(4-Amino-3-chlorophenyl)methylsulfonamido)-2-(4-chlorophenyl)-5-cyclopropyl-N-methylbenzofuran-3-carboxamide A solution of 6-(N-(3-chloro-4-nitrophenyl)methylsulfonamido)-2-(4-chlorophenyl)-5-cyclopropyl-N-methylbenzofuran-3-carboxamide (0.500 g, 0.870 mmol) in 3:1 MeOH/THF (30 mL) was subjected to hydrogenation at 45 psi in the presence of 5% sulfided platinum on carbon (50 mg). After 18 hours the reaction vessel was purged with nitrogen, catalyst removed by filtration through celite and the filtrate concentrated to dryness at reduced pressure. The residue was recrystallized from hexane/EtOAc to afford the title compound (0.45 g, 95%) as an off-white solid. LCMS (m/z, ES$^+$)=544 (M+H+).

Step 3: 6-(N-(4-Bromo-3-chlorophenyl)methylsulfonamido)-2-(4-chlorophenyl)-5-cyclopropyl-N-methylbenzofuran-3-carboxamide A stirred suspension of 6-(N-(4-amino-3-chlorophenyl)methylsulfonamido)-2-(4-chlorophenyl)-5-cyclopropyl-N-methylbenzofuran-3-carboxamide (0.421 g, 0.773 mmol) in 25 mL of acetonitrile was treated with 25 mL of 48% aqueous HBr and the resulting suspension cooled in an ice water bath. To the mixture was added a solution of sodium nitrite (0.056 g, 0.812 mmol) in 2 mL of water. After stirring at 0° C. for 30 minutes an additional 14 mg portion of sodium nitrite in 1 mL of water was added. After stirring at 0° C. for another 30 minutes, the mixture was treated with CuBr (0.130 g, 0.906 mmol) in four portions over 5 minutes. The mixture was warmed to 60° C. for 30 minutes and then cooled to RT. The mixture was partitioned between EtOAc and 5% aqueous sodium bisulfite. The EtOAc solution was washed with 5% aqueous sodium bisulfite (2×), saturated aqueous sodium bicarbonate (2×), brine (1×), dried over sodium sulfate and concentrated to dryness at reduced pressure. The crude product was purified by flash chromatography (silica gel, gradient from hexane to 3:7 hexane/EtOAc) followed by recrystallization from hexane/EtOAc to give the title compound (0.212 g, 45%) as a white solid. LCMS (m/z, ES$^+$)=609 (M+H+).

Step 4: (2-Chloro-4-(N-(2-(4-chlorophenyl)-5-cyclopropyl-3-(methylcarbamoyl)benzofuran-6-yl)methylsulfonamido)phenyl)boronic acid A mixture of 6-(N-(4-bromo-3-chlorophenyl)methylsulfonamido)-2-(4-chlorophenyl)-5-cyclopropyl-N-methylbenzofuran-3-carboxamide (0.205 g, 0.337 mmol), bis(pinacolato)diboron (0.428 g, 1.69 mmol), potassium acetate (0.165 g, 1.69 mmol) and Pd(II)(dppf)Cl$_2$ dichloromethane complex (0.0138 g, 0.017 mmol) in anhydrous 1,4-dioxane (4 mL) in a sealed tube was sparged with nitrogen for 10 minutes. The vessel was sealed and heated in an 80° C. oil bath with stirring. After 4 hours the mixture was cooled to RT and diluted with EtOAc. The resulting solution was washed with water (2×), saturated brine (1×), and dried over sodium sulfate. While stirring with sodium sulfate, celite was added to facilitate removal of the insoluble black material that remained suspended in solution. The mixture was filtered through a medium frit to afford a golden-brown filtrate that was concentrated to dryness at reduced pressure. The residue was dissolved in 10 mL of THF and the resulting solution cooled in an ice water bath. The solution was treated with 1N aqueous HCl (4 mL) followed by sodium periodate (1.08 g, 5.05 mmol). The mixture was stirred at 0° C. for 10 minutes and then allowed to warm to RT. After 18 hours the mixture was partitioned between water and EtOAc and the phases separated. The aqueous solution was extracted with EtOAc (2×). The combined EtOAc solutions were washed with 5% aqueous sodium bisulfite (4×), saturated brine (2×), dried over sodium sulfate and concentrated to dryness at reduced pressure. The residue was subjected to flash chromatography (silica gel, 2-part gradient: DCM to EtOAc over 15 minutes, then switch solvents to A=9:1 DCM/MeOH, B=DCM; gradient from 100% B to 65% A over 4 minutes, then 65% A isocratic for 15 minutes) to give a light tan foam (0.142 g). This material was dissolved in acetonitrile (3 mL) and the solution stirred with dropwise addition of 0.25 N aqueous HCl (10 mL) over a 20 minute period. A white suspension was produced which was stirred at RT. After 2 hours the solid was collected by filtration in a medium fritted funnel. The filter cake was washed with water (2×), suction air dried for 30 minutes, and then dried in vacuo overnight to afford the title compound (0.119 g, 62%) as a white solid. $^1$H NMR (400 MHz, DMSO-d$_6$) δ ppm 8.50 (q, 1H) 8.32 (s, 2H) 8.11 (s, 1H) 7.92 (d, 2H) 7.62 (d, 2H) 7.30-7.45 (m, 3H) 7.19 (s, 1H) 3.40 (s, 3H) 2.83 (d, 3H) 2.06-2.16 (m, 1H) 0.72-1.07 (m, 3H) 0.52 (br s, 1H). LCMS (m/z, ES$^+$)=573 (M+H+).

Example 3

4-(N-(5-cyclopropyl-2-(4-fluorophenyl)-3-(methylcarbamoyl)benzofuran-6-yl)methylsulfonamido)phenylboronic acid

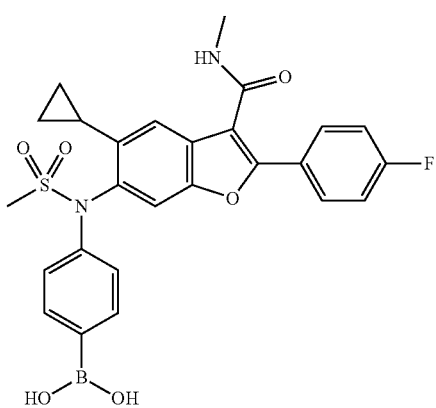 [SMILES: CNC(=O)c1c(-c2ccc(F)cc2)oc2cc(N(c3ccc(B(O)O)cc3)S(C)(=O)=O)c(C3CC3)cc12]

Step 1: 6-(N-(4-bromophenyl)methylsulfonamido)-5-cyclopropyl-2-(4-fluorophenyl)-N-methylbenzofuran-3-carboxamide A mixture of 5-cyclopropyl-2-(4-fluorophenyl)-N-methyl-6-[(methylsulfonyl)amino]-1-benzofuran-3-carboxamide (500 mg, 1.244 mmol), 4-bromophenylboronic acid (1.5 g, 7.464 mmol), copper(II) acetate monohydrate (372 mg, 1.866 mmol), triethylamine (252 mg, 2.488 mmol), and 4 Å molecular sieves (1 g) in dichloromethane (160 mL) was stirred for 2 days. The solution was filtered, concentrated to dryness, and purified by column chromatography to afford 6-(N-(4-bromophenyl)methylsulfonamido)-5-cyclopropyl-2-(4-fluorophenyl)-N-methylbenzofuran-3-carboxamide (180 mg, 0.323 mmol, 26% yield) as a brown solid. LCMS (m/z, ES$^+$)=557, 559 (M+H+).

Step 2: 5-cyclopropyl-2-(4-fluorophenyl)-N-methyl-6-(N-(4-(4,4,5,5-tetramethyl-1,3,2-dioxaborolan-2-yl)phenyl)methylsulfonamido)benzofuran-3-carboxamide A suspension of 6-(N-(4-bromophenyl)methylsulfonamido)-5-cyclopropyl-2-(4-fluorophenyl)-N-methylbenzofuran-3-carboxamide (150 mg, 0.269 mmol), potassium acetate (80 mg, 0.807 mmol), bis(pinacolato)diboron (205 mg, 0.807 mmol), and Pd(dppf)Cl$_2$ dichloromethane complex (22 mg, 0.027 mmol) in 1,4-dioxane (20 mL) was maintained at 95° C. with stirring overnight. The solution was cooled to room temperature, filtered, concentrated to dryness, and purified by column chromatography to afford 5-cyclopropyl-2-(4-fluorophenyl)-N-methyl-6-(N-(4-(4,4,5,5-tetramethyl-1,3,2-dioxaborolan-2-yl)phenyl)methylsulfonamido)benzofuran-3-carboxamide (152 mg, 0.251 mmol, 94% yield) as a brown solid. LCMS (m/z, ES$^+$)=605 (M+H+)

Step 3: 4-(N-(5-cyclopropyl-2-(4-fluorophenyl)-3-(methylcarbamoyl)benzofuran-6-yl)methylsulfonamido)phenylboronic acid A suspension of 5-cyclopropyl-2-(4-fluorophenyl)-N-methyl-6-(N-(4-(4,4,5,5-tetramethyl-1,3,2-dioxaborolan-2-yl)phenyl)methylsulfonamido)benzofuran-3-carboxamide (152 mg, 0.251 mmol), polymer-supported benzeneboronic acid (480 mg, 1.255 mmol), and aqueous 5N HCl (0.35 mL, 1.757 mmol) in tetrahydrofuran (15 mL) was stirred at room temperature for 48 hours. The solution was filtered, concentrated to dryness, and purified by reverse phase HPLC to afford 4-(N-(5-cyclopropyl-2-(4-fluorophenyl)-3-(methylcarbamoyl)benzofuran-6-yl)methylsulfonamido)phenylboronic acid (45 mg, 0.086 mmol, 34% yield) as a white solid. $^1$H NMR (METHANOL-d$_4$) δ: 7.98 (d, 1H), 7.96 (d, 1H), 7.87 (S, 1H), 7.66 (d, 2H), 7.46 (d, 2H), 7.32-7.26 (m, 3H), 3.33 (s, 3H), 2.99 (s, 3H), 2.22-2.18 (m, 1H), 1.10-0.37 (m, 4H). LCMS (m/z, ES$^+$)=523 (M+H+)

Example 4

3-(N-(5-cyclopropyl-2-(4-fluorophenyl)-3-(methylcarbamoyl)benzofuran-6-yl)methylsulfonamido)phenylboronic acid

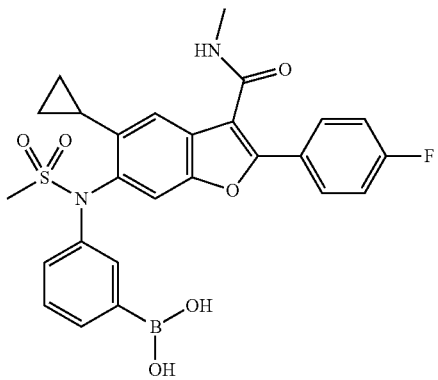 [SMILES: CNC(=O)c1c(-c2ccc(F)cc2)oc2cc(N(c3cccc(B(O)O)c3)S(C)(=O)=O)c(C3CC3)cc12]

Step 1: 6-(N-(3-bromophenyl)methylsulfonamido)-5-cyclopropyl-2-(4-fluorophenyl)-N-methylbenzofuran-3-carboxamide A mixture of 5-cyclopropyl-2-(4-fluorophenyl)-N-methyl-6-[(methylsulfonyl)amino]-1-benzofuran-3-carboxamide (500 mg, 1.24 mmol), 3-bromophenylboronic acid (1.5 g, 7.46 mmol), copper(II) acetate monohydrate (372 mg, 1.87 mmol), triethylamine (252 mg, 2.49 mmol), 4 Å molecular sieves (1 g) in dichloromethane (160 mL) was stirred for 2 days. The solid was filtered off, the filtrate was concentrated to dryness and purified by column chromatography to afford 6-(N-(3-bromophenyl)methylsulfonamido)-5-cyclopropyl-2-(4-fluorophenyl)-N-methylbenzofuran-3-carboxamide (270 mg, 0.48 mmol, 39% yield) as a brown solid. LCMS (m/z, ES$^+$)=557, 559 (M+H+).

Step 2: 5-cyclopropyl-2-(4-fluorophenyl)-N-methyl-6-(N-(3-(4,4,5,5-tetramethyl-1,3,2-dioxaborolan-2-yl)phenyl)methylsulfonamido)benzofuran-3-carboxamide A suspension of 6-(N-(3-bromophenyl)methylsulfonamido)-5-cyclopropyl-2-(4-fluorophenyl)-N-methylbenzofuran-3-carboxamide (240 mg, 0.43 mmol), potassium acetate (128 mg, 1.29 mmol), bis(pinacolato)diboron (328 mg, 1.29 mmol), and Pd(dppf)Cl$_2$ dichloromethane complex (35 mg, 0.043 mmol) in 1,4-dioxane (20 mL) was maintained at 95° C. with stirring overnight. The reaction mixture was cooled to room temperature and the solid was filtered off. The filtrate was concentrated to dryness and purified by column chromatography to afford 5-cyclopropyl-2-(4-fluorophenyl)-N-methyl-6-(N-(3-(4,4,5,5-tetramethyl-1,3,2-dioxaborolan-2-yl)phenyl)methylsulfonamido)benzofuran-3-carboxamide (269 mg, 0.45 mmol, 92% yield) as a brown solid. LCMS (m/z, ES$^+$)=605 (M+H+)

Step 3: 3-(N-(5-cyclopropyl-2-(4-fluorophenyl)-3-(methylcarbamoyl)benzofuran-6-yl)methylsulfonamido)phenylboronic acid A suspension of 5-cyclopropyl-2-(4-fluorophenyl)-N-methyl-6-(N-(3-(4,4,5,5-tetramethyl-1,3,2-dioxaborolan-2-yl)

phenyl)methylsulfonamido)benzofuran-3-carboxamide (269 mg, 0.45 mmol), polymer-supported benzeneboronic acid (770 mg, 2.23 mmol), aqueous 5N HCl (0.62 mL, 3.12 mmol) in tetrahydrofuran (15 mL) was stirred at room temperature for 48 hours. The mixture was filtered, the filtrate was concentrated to dryness and purified by reverse phase HPLC to afford 3-(N-(5-cyclopropyl-2-(4-fluorophenyl)-3-(methylcarbamoyl)benzofuran-6-yl)methylsulfonamido)phenylboronic acid (41 mg, 0.078 mmol, 17% yield) as a white solid. $^1$H NMR (METHANOL-$d_4$) δ 7.99-7.95 (m, 2H), 7.94 (s, 1H), 7.77-7.38 (m, 4H), 7.32-7.25 (m, 3H), 3.32 (s, 3H), 2.98 (s, 3H), 2.29-2.25 (m, 1H), 1.10-0.37 (m, 4H). LCMS (m/z, ES$^+$)=523 (M+H+).

Example 5

4-(N-(5-cyclopropyl-2-(4-fluorophenyl)-3-(methylcarbamoyl)benzofuran-6-yl)methylsulfonamido)-2-fluorophenylboronic acid

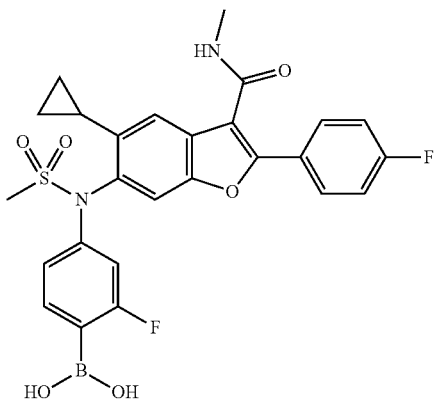 [SMILES: CNC(=O)c1c(-c2ccc(F)cc2)oc2cc(N(c3ccc(B(O)O)c(F)c3)S(C)(=O)=O)c(C3CC3)cc12]

Step 1: 5-cyclopropyl-6-(N-(3-fluoro-4-nitrophenyl) methylsulfonamido)-2-(4-fluorophenyl)-N-methylbenzofuran-3-carboxamide A suspension of 2,4-difluoro-1-nitrobenzene (261 mg, 1.64 mmol) and 5-cyclopropyl-2-(4-fluorophenyl)-N-methyl-6-[(methylsulfonyl)amino]-1-benzofuran-3-carboxamide (600 mg, 1.49 mmol) in dimethoxyethane (0.8 mL) and water (0.2 mL) was treated with potassium carbonate (616.86 mg, 4.47 mmol) and heated to 100° C. for 24 hours. The reaction mixture was concentrated and purified by column chromatography to afford 5-cyclopropyl-6-(N-(3-fluoro-4-nitrophenyl)methylsulfonamido)-2-(4-fluorophenyl)-N-methylbenzofuran-3-carboxamide (230 mg, 0.43 mmol, 29% yield) as a yellow powder. LCMS (m/z, ES$^+$)=542 (M+H+)

Step 2: 6-(N-(4-amino-3-fluorophenyl)methylsulfonamido)-5-cyclopropyl-2-(4-fluorophenyl)-N-methylbenzofuran-3-carboxamide A mixture of 5-cyclopropyl-6-(N-(3-fluoro-4-nitrophenyl) methylsulfonamido)-2-(4-fluorophenyl)-N-methylbenzofuran-3-carboxamide (230 mg, 0.43 mmol) and stannous chloride (291 mg, 1.29 mmol) in ethyl acetate (5 mL) and ethanol (5 mL) was maintained at reflux for 3 hours. The mixture was cooled to room temperature and partitioned between ethyl acetate and water. The organic layer was dried over sodium sulfate, filtered, concentrated to dryness, and purified by column chromatography to afford 6-(N-(4-amino-3-fluorophenyl)methylsulfonamido)-5-cyclopropyl-2-(4-fluorophenyl)-N-methylbenzofuran-3-carboxamide (200 mg, 0.39 mmol, 90% yield) as a yellow powder. LCMS (m/z, ES$^+$)=512 (M+H+)

Step 3: 6-(N-(4-bromo-3-fluorophenyl)methylsulfonamido)-5-cyclopropyl-2-(4-fluorophenyl)-N-methylbenzofuran-3-carboxamide A suspension of 6-(N-(4-amino-3-fluorophenyl)methylsulfonamido)-5-cyclopropyl-2-(4-fluorophenyl)-N-methylbenzofuran-3-carboxamide (200 mg, 0.39 mmol) in acetonitrile (5 mL) and aqueous hydrogen bromide solution (5 mL) was treated with an aqueous sodium nitrite (29.6 mg, 0.43 mmol) solution at 0° C. with stirring for 0.5 hours. Cuprous bromide (64.3 mg, 0.45 mmol) was then added to the solution in portions at 0° C., and heated to reflux for 2 hours. The solution was cooled to room temperature and partitioned between ethyl acetate and water. The organic layer was separated, dried over sodium sulfate, filtered, concentrated to dryness, and purified by column chromatography to afford 6-(N-(4-bromo-3-fluorophenyl)methylsulfonamido)-5-cyclopropyl-2-(4-fluorophenyl)-N-methylbenzofuran-3-carboxamide (140 mg, 0.24 mmol, 61% yield) as a white solid. LCMS (m/z, ES$^+$)=575, 577 (M+H+)

Step 4: 5-cyclopropyl-6-(N-(3-fluoro-4-(4,4,5,5-tetramethyl-1,3,2-dioxaborolan-2-yl)phenyl)methylsulfonamido)-2-(4-fluorophenyl)-N-methylbenzofuran-3-carboxamide A suspension of 6-(N-(4-bromo-3-fluorophenyl)methylsulfonamido)-5-cyclopropyl-2-(4-fluorophenyl)-N-methylbenzofuran-3-carboxamide (140 mg, 0.24 mmol) and bis(pinacolato)diboron (914 mg, 3.60 mmol) in anhydrous dioxane (5 mL) was treated with PdCl$_2$(dppf) (19.6 mg, 0.024 mmol), potassium acetate (47.04 mg, 0.48 mmol) and maintained under N$_2$ with stirring at 90° C. for 4 hours. The suspension was cooled to room temperature and partitioned between ethyl acetate and water. The organic layer was separated, dried over sodium sulfate, filtered, concentrated to dryness, and purified by column chromatography to afford 5-cyclopropyl-6-(N-(3-fluoro-4-(4,4,5,5-tetramethyl-1,3,2-dioxaborolan-2-yl)phenyl)methylsulfonamido)-2-(4-fluorophenyl)-N-methylbenzofuran-3-carboxamide (140 mg, 0.22 mmol, 56% yield) as a white solid. LCMS (m/z, ES$^+$)=623 (M+H+)

Step 5: 4-(N-(5-cyclopropyl-2-(4-fluorophenyl)-3-(methylcarbamoyl)benzofuran-6-yl)methylsulfonamido)-2-fluorophenylboronic acid A solution of 5-cyclopropyl-6-(N-(3-fluoro-4-(4,4,5,5-tetramethyl-1,3,2-dioxaborolan-2-yl)phenyl)methylsulfonamido)-2-(4-fluorophenyl)-N-methylbenzofuran-3-carboxamide (140 mg, 0.22 mmol) and 1N aqueous HCl (2 mL) in anhydrous THF (10 mL) was treated with polymer-supported benzeneboronic acid (5000 mg) and stirred at room temperature for 24 hours. The mixture was partitioned between ethyl acetate and water. The organic layer was separated, dried over sodium sulfate, filtered, concentrated to dryness, and purified by reverse phase HPLC to afford 4-(N-(5-cyclopropyl-2-(4-fluorophenyl)-3-(methylcarbamoyl)benzofuran-6-yl)methylsulfonamido)-2-fluorophenylboronic acid (50 mg, 0.092 mmol, 42% yield) as a white solid. $^1$H NMR (300 MHz, METHANOL-d4) δ 7.96 (dd, 2H), 7.83 (s, 1H), 7.45-7.15 (m, 6H), 3.43 (s, 3H), 2.96 (s, 3H), 2.12 (m, 1H), 1.01-0.52 (m, 4H). LCMS (m/z, ES+)=541 (M+H+)

Example 6

4-(N-(5-cyclopropyl-2-(4-fluorophenyl)-3-(methylcarbamoyl)benzofuran-6-yl)methylsulfonamido)-3-fluorophenylboronic acid

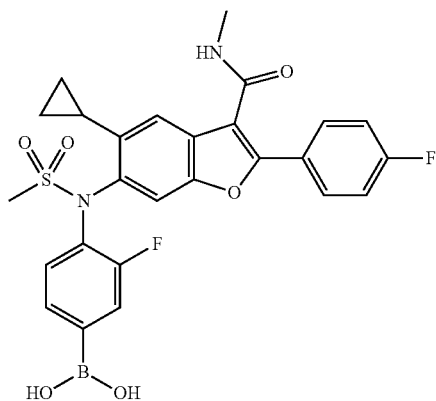 [SMILES: CNC(=O)c1c(-c2ccc(F)cc2)oc2cc(N(c3ccc(B(O)O)cc3F)S(C)(=O)=O)c(C3CC3)cc12]

Step 1: 5-cyclopropyl-6-(N-(2-fluoro-4-nitrophenyl)methylsulfonamido)-2-(4-fluorophenyl)-N-methylbenzofuran-3-carboxamide A mixture of 5-cyclopropyl-2-(4-fluorophenyl)-N-methyl-6-[(methylsulfonyl)amino]-1-benzofuran-3-carboxamide (402 mg, 1 mmol), 1,2-difluoro-4-nitrobenzene (318 mg, 2 mmol) and potassium carbonate (414 mg, 3 mmol) in 1,2-dimethoxyethane (20 mL) and water (5 mL) was heated at 100° C. for 48 hours. The solution was cooled to room temperature and concentrated, diluted with ethyl acetate (50 mL) and washed with water. The organic layer was dried over sodium sulfate, filtered, concentrated to dryness, and purified by column chromatography to afford 5-cyclopropyl-6-(N-(2-fluoro-4-nitrophenyl)methylsulfonamido)-2-(4-fluorophenyl)-N-methylbenzofuran-3-carboxamide (420 mg, 0.77 mmol, 77% yield) as a yellow solid. LCMS (m/z, ES$^+$)=542 (M+H+)

Step 2: 6-(N-(4-amino-2-fluorophenyl)methylsulfonamido)-5-cyclopropyl-2-(4-fluorophenyl)-N-methylbenzofuran-3-carboxamide A suspension of 5-cyclopropyl-6-(N-(2-fluoro-4-nitrophenyl)methylsulfonamido)-2-(4-fluorophenyl)-N-methylbenzofuran-3-carboxamide (420 mg, 0.77 mmol) and tin(II) chloride dihydrate (519 mg, 2.31 mmol) in ethyl acetate (15 mL) and ethanol (15 mL) was heated at 80° C. for 2 hours. The solution was cooled to room temperature and concentrated, diluted with ethyl acetate (50 mL) and washed with sodium carbonate solution. The organic layer was dried over sodium sulfate, filtered, concentrated to dryness, and purified by column chromatography to afford 6-(N-(4-amino-2-fluorophenyl)methylsulfonamido)-5-cyclopropyl-2-(4-fluorophenyl)-N-methylbenzofuran-3-carboxamide (360 mg, 0.7 mmol, 91% yield) as a yellow solid. LCMS (m/z, ES$^+$)=512 (M+H+).

Step 3: 6-(N-(4-bromo-2-fluorophenyl)methylsulfonamido)-5-cyclopropyl-2-(4-fluorophenyl)-N-methylbenzofuran-3-carboxamide To a solution of 6-(N-(4-amino-2-fluorophenyl)methylsulfonamido)-5-cyclopropyl-2-(4-fluorophenyl)-N-methylbenzofuran-3-carboxamide (360 mg, 0.7 mmol) in acetonitrile (20 mL) was added hydrobromic acid (5 mL, 40% in water) followed by sodium nitrite (49 mg, 0.77 mmol in 2 mL water) dropwise at 0° C. After stirring for 10 minutes at 0° C., cuprous bromide (115 mg, 0.8 mmol) was added. The mixture was warmed to 80° C. and stirred for 1 hour. The mixture was cooled to room temperature and diluted with water (20 mL). The aqueous layer was extracted with ethyl acetate (3×20 mL), dried over sodium sulfate, filtered, concentrated to dryness, and purified by column chromatography to afford 6-(N-(4-bromo-2-fluorophenyl)methylsulfonamido)-5-cyclopropyl-2-(4-fluorophenyl)-N-methylbenzofuran-3-carboxamide (240 mg, 0.42 mmol, 60% yield) as an off-white solid. LCMS (m/z, ES$^+$)=575, 577 (M+H+).

Step 4: 5-cyclopropyl-6-(N-(2-fluoro-4-(4,4,5,5-tetramethyl-1,3,2-dioxaborolan-2-yl)phenyl)methylsulfonamido)-2-(4-fluorophenyl)-N-methylbenzofuran-3-carboxamide A suspension of 6-(N-(4-bromo-2-fluorophenyl)methylsulfonamido)-5-cyclopropyl-2-(4-fluorophenyl)-N-methylbenzofuran-3-carboxamide (240 mg, 0.42 mmol), potassium acetate (123 mg, 1.26 mmol), bis(pinacolato)diboron (533 mg, 2.1 mmol) and PdCl$_2$(dppf) (68.5 mg, 0.084 mmol) in 1,4-dioxane (30 mL) was heated at 100° C. under nitrogen with stirring for 16 h. The solution was cooled to room temperature, filtered, concentrated, and purified by column chromatography to afford 5-cyclopropyl-6-(N-(2-fluoro-4-(4,4,5,5-tetramethyl-1,3,2-dioxaborolan-2-yl)phenyl)methylsulfonamido)-2-(4-fluorophenyl)-N-methylbenzofuran-3-carboxamide (200 mg, 0.32 mmol, 76% yield) as a light yellow solid. LCMS (m/z, ES$^+$)=623 (M+H+).

Step 5: 4-(N-(5-cyclopropyl-2-(4-fluorophenyl)-3-(methylcarbamoyl)benzofuran-6-yl)methylsulfonamido)-3-fluorophenylboronic acid A suspension of 5-cyclopropyl-6-(N-(2-fluoro-4-(4,4,5,5-tetramethyl-1,3,2-dioxaborolan-2-yl)phenyl)methylsulfonamido)-2-(4-fluorophenyl)-N-methylbenzofuran-3-carboxamide (200 mg, 0.32 mmol), polymer supported benzeneboronic acid (600 mg, 1.60 mmol) and aqueous 5N HCl (0.45 mL, 2.24 mmol) in tetrahydrofuran (20 mL) was stirred at room temperature for 24 h. The solution was filtered, concentrated to dryness, and purified by reverse phase HPLC to afford 4-(N-(5-cyclopropyl-2-(4-fluorophenyl)-3-(methylcarbamoyl)benzofuran-6-yl)methylsulfonamido)-3-fluorophenylboronic acid (61 mg, 0.11 mmol, 35% yield) as a white solid. $^1$H NMR (METHANOL-d$_4$) δ 8.03 (s, 1H), 7.97-

7.79 (m, 2H), 7.57 (dd, 3H), 7.24 (dd, 3H), 3.29 (s, 3H), 2.94 (s, 3H), 2.42 (s, 1H), 1.00 (d, 2H), 0.69 (s, 2H). LCMS (m/z, ES$^+$)=541 (M+H+).

Example 7

4-(N-(2-(4-chlorophenyl)-5-cyclopropyl-3-(methylcarbamoyl)benzofuran-6-yl)methylsulfonamido)-2-fluorophenylboronic acid

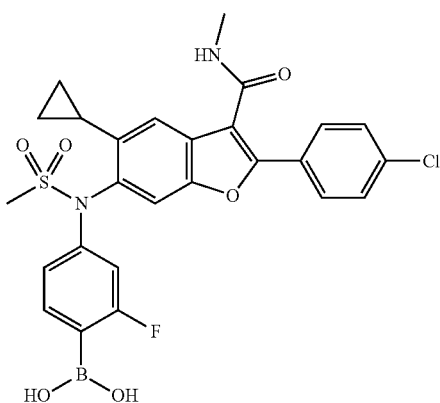 [SMILES: CNC(=O)c1c(-c2ccc(Cl)cc2)oc2cc(N(c3ccc(B(O)O)c(F)c3)S(C)(=O)=O)c(C3CC3)cc12]

Step 1: 6-(N-(4-(benzyloxy)-3-fluorophenyl)methylsulfonamido)-2-(4-chlorophenyl)-5-cyclopropyl-N-methylbenzofuran-3-carboxamide A mixture of 2-(4-chlorophenyl)-5-cyclopropyl-N-methyl-6-(methylsulfonamido)benzofuran-3-carboxamide (2.0 g, 4.77 mmol), (4-(benzyloxy)-3-fluorophenyl)boronic acid (1.762 g, 7.16 mmol), Cu(OAc)$_2$ (1.301 g, 7.16 mmol), triethylamine (3.33 mL, 23.87 mmol) and powdered 3 Å molecular sieves (2 g) in CH$_2$Cl$_2$ (60 mL) was stirred in a flask open to the air and equipped with a drying tube. After 12 hours the mixture was treated with additional (4-(benzyloxy)-3-fluorophenyl)boronic acid (1.762 g, 7.16 mmol) and Cu(OAc)$_2$ (1.301 g, 7.16 mmol) and stirred at room temperature for 4 d. The mixture was diluted with CH$_2$Cl$_2$, filtered through Celite and the dark brown filtrate was concentrated to dryness. The crude material was purified by flash chromatography on silica gel (0-4% EtOAc/CH$_2$Cl$_2$) to afford the desired compound which was further purified by flash chromatography on silica gel eluted (0-40% EtOAc/hexane) to give the desired compound as a light-tan solid (406 mg, 14%). LCMS (m/z, ES$^+$)=619 (M+H+).

Step 2: 2-(4-chlorophenyl)-5-cyclopropyl-6-(N-(3-fluoro-4-hydroxyphenyl)methylsulfonamido)-N-methylbenzofuran-3-carboxamide 6-(N-(4-(benzyloxy)-3-fluorophenyl)methylsulfonamido)-2-(4-chlorophenyl)-5-cyclopropyl-N-methylbenzofuran-3-carboxamide (350 mg, 0.565 mmol) was dissolved in ethyl acetate (8.0 mL) and ethanol (8.0 mL). 10% of Pd/C (30.1 mg, 0.283 mmol) was added followed by the addition of H$_2$ (1 atmosphere, balloon). The mixture was stirred for 2 h at RT and filtered through Celite. The filtrate was concentrated to dryness and rinsed twice with hexane to give the desired product as a white solid which was used without further purification. LCMS (m/z, ES$^+$)=529 (M+H+).

Step 3: 4-(N-(2-(4-chlorophenyl)-5-cyclopropyl-3-(methylcarbamoyl)benzofuran-6-yl)methylsulfonamido)-2-fluorophenyl trifluoromethanesulfonate Tf$_2$O (0.157 mL, 0.930 mmol) in CH$_2$Cl$_2$ (1 mL) was added dropwise to a suspension of 2-(4-chlorophenyl)-5-cyclopropyl-6-(N-(3-fluoro-4-hydroxyphenyl)methylsulfonamido)-N-methylbenzofuran-3-carboxamide (328 mg, 0.620 mmol) and pyridine (0.251 mL, 3.10 mmol) in CH$_2$Cl$_2$ (5 mL) under N$_2$ at room temperature. The mixture was stirred at room temperature for 3 h then water was added. The mixture was extracted with CH$_2$Cl$_2$ and the combined organic phases were dried over Na$_2$SO$_4$, filtered, concentrated at reduced pressure, and purified by flash chromatography on silica gel eluted (0-40% EtOAc/hexane) to give the desired compound as a white solid (410 mg, 83% yield). LCMS (m/z, ES$^+$)=661 (M+H+).

Step 4: 2-(4-chlorophenyl)-5-cyclopropyl-6-(N-(3-fluoro-4-(4,4,5,5-tetramethyl-1,3,2-dioxaborolan-2-yl)phenyl)methylsulfonamido)-N-methylbenzofuran-3-carboxamide A mixture of 4-(N-(2-(4-chlorophenyl)-5-cyclopropyl-3-(methylcarbamoyl)benzofuran-6-yl)methylsulfonamido)-2-fluorophenyl trifluoromethanesulfonate (170 mg, 0.257 mmol), potassium acetate (76 mg, 0.772 mmol), bis(pinacolato)diboron (98 mg, 0.386 mmol) and PdCl$_2$(dppf)-CH$_2$Cl$_2$ adduct (10.50 mg, 0.013 mmol) in 1,4-dioxane (2.0 ml) was heated at 80° C. in a seal tube under N$_2$ overnight. The mixture was cooled to room temperature, diluted with EtOAc, and filtered through a pad of silica gel and Celite. The filtrate was concentrated to dryness to give the crude product as tan foam which was used without further purification. LCMS (m/z, ES$^+$)=639 (M+H+).

Step 5: (4-(N-(2-(4-chlorophenyl)-5-cyclopropyl-3-(methylcarbamoyl)benzofuran-6-yl)methylsulfonamido)-2-fluorophenyl)boronic acid Sodium periodate (549 mg, 2.57 mmol) was added to a mixture of 2-(4-chlorophenyl)-5-cyclopropyl-6-(N-(3-fluoro-4-(4,4,5,5-tetramethyl-1,3,2-dioxaborolan-2-yl)phenyl)methylsulfonamido)-N-methylbenzofuran-3-carboxamide (164 mg, 0.257 mmol) in THF (6 mL) and 1N HCl (3.21 mL, 3.21 mmol). The mixture was stirred at room temperature overnight and EtOAc and water were added. The aqueous layer was extracted with EtOAc (2×) and the combined organic phases were washed with 10% aq. Na$_2$S$_2$O$_3$, brine, dried over Na$_2$SO$_4$, filtered and concentrated to dryness. The residue was purified by reverse phase HPLC (MeCN/H$_2$O with 0.1% TFA) to give the title compound as a white solid (80 mg, 56%). $^1$H NMR (400 MHz, DMSO-d$_6$) δ ppm 8.52 (q, 1H) 8.23 (br. s., 1H) 8.07 (s, 1H) 7.94 (d, 2H) 7.64 (d, 2H) 7.55 (t, 1H) 7.22 (s, 1H) 7.11 (s, 1H) 7.07-7.10 (m, 1H) 3.45

(s, 4H) 2.85 (d, 3H) 2.04-2.15 (m, 1H) 1.00 (br. s., 1H) 0.82 (d, 2H) 0.54 (br. s., 1H). LCMS (m/z, ES+)=557 (M+H+).

Example 8

6-(N-(5-cyclopropyl-2-(4-fluorophenyl)-3-(methylcarbamoyl)benzofuran-6-yl)methylsulfonamido)pyridin-3-ylboronic acid

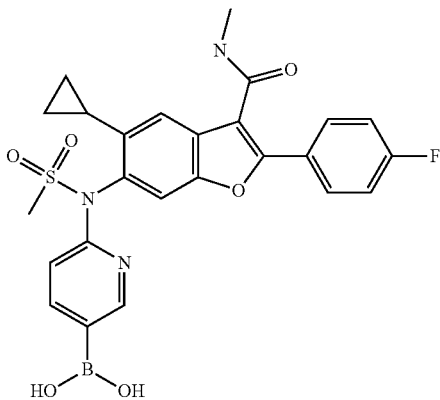 [SMILES: CNC(=O)c1c(-c2ccc(F)cc2)oc2cc(N(c3ccc(B(O)O)cn3)S(C)(=O)=O)c(C3CC3)cc12]

Step 1: 6-(N-(5-bromopyridin-2-yl)methylsulfonamido)-5-cyclopropyl-2-(4-fluorophenyl)-N-methylbenzofuran-3-carboxamide To a solution of 5-cyclopropyl-2-(4-fluorophenyl)-N-methyl-6-[(methylsulfonyl)amino]-1-benzofuran-3-carboxamide (400 mg, 1.00 mmol) in dimethylformamide (5 mL) at 0° C. was added lithium bis(trimethylsilyl)amide (1.5 mL, 1.50 mmol). After 1 hour 5-bromo-2-fluoropyridine (350 mg, 2.00 mmol) was added and stirring was maintained at 80° C. for 16 hours. The solution was cooled to room temperature, diluted with water, and extracted with ethyl acetate (3×50 mL). The combined extracts were washed with brine, dried over sodium sulfate and concentrated to dryness at reduced pressure. The crude material was purified by column chromatography to afford 6-(N-(5-bromopyridin-2-yl)methylsulfonamido)-5-cyclopropyl-2-(4-fluorophenyl)-N-methylbenzofuran-3-carboxamide (430 mg, 0.775 mmol, 77.5% yield) as a yellow solid. LCMS (m/z, ES+)=559 (M+H+).

Step 2: 5-cyclopropyl-2-(4-fluorophenyl)-N-methyl-6-(N-(5-(4,4,5,5-tetramethyl-1,3,2-dioxaborolan-2-yl)pyridin-2-yl)methylsulfonamido)benzofuran-3-carboxamide A suspension of 6-(N-(5-bromopyridin-2-yl)methylsulfonamido)-5-cyclopropyl-2-(4-fluorophenyl)-N-methylbenzofuran-3-carboxamide (400 mg, 0.72 mmol), potassium acetate (210 mg, 2.14 mmol), bis(pinacolato)diboron (2721 mg, 10.71 mmol), and PdCl$_2$(dppf) (58 mg, 0.071 mmol) in 1,4-dioxane (10 mL) in a thick-walled glass pressure vessel was maintained at 90° C. with stirring for 16 hours. The solution was cooled to room temperature and filtered. The filtrates were concentrated and purified by column chromatography to afford 5-cyclopropyl-2-(4-fluorophenyl)-N-methyl-6-(N-(5-(4,4,5,5-tetramethyl-1,3,2-dioxaborolan-2-yl)pyridin-2-yl)methylsulfonamido)benzofuran-3-carboxamide (320 mg, 0.53 mmol, 74% yield) as a white solid. LCMS (m/z, ES+)=606 (M+H+).

Step 3: 6-(N-(5-cyclopropyl-2-(4-fluorophenyl)-3-(methylcarbamoyl)benzofuran-6-yl)methylsulfonamido)pyridin-3-yl)boronic acid A suspension of 5-cyclopropyl-2-(4-fluorophenyl)-N-methyl-6-(N-(5-(4,4,5,5-tetramethyl-1,3,2-dioxaborolan-2-yl)pyridin-2-yl)methylsulfonamido)benzofuran-3-carboxamide (320 mg, 0.53 mmol), polymer-supported benzeneboronic acid (862 mg, 2.65 mmol) and 5N aqueous HCl (0.74 mL, 3.78 mmol) in tetrahydrofuran (10 mL) was stirred at room temperature for 48 h. The solution was filtered, concentrated to dryness, and purified by reverse phase HPLC to afford 6-(N-(5-cyclopropyl-2-(4-fluorophenyl)-3-(methylcarbamoyl)benzofuran-6-yl)methylsulfonamido)pyridin-3-yl)boronic acid (80 mg, 0.153 mmol, 29% yield) as a white solid. $^1$H NMR (300 MHz, METHANOL-d$_4$) δ 8.36 (s, 1H), 7.72 (m, 3H), 7.57 (s, 1H), 7.25-7.1 (m, 3H), 6.90-6.87 (m, 1H), 3.59 (s, 3H), 3.03 (s, 3H), 2.13-2.09 (m, 1H), 1.07-1.03 (m, 2H), 0.70 (m, 2H). LCMS (m/z, ES+)=524 (M+H+).

Example 9

(4-(N-(5-cyclopropyl-2-(4-fluorophenyl)-3-(methylcarbamoyl)benzofuran-6-yl)methylsulfonamido)-2-(difluoromethyl)phenyl)boronic acid

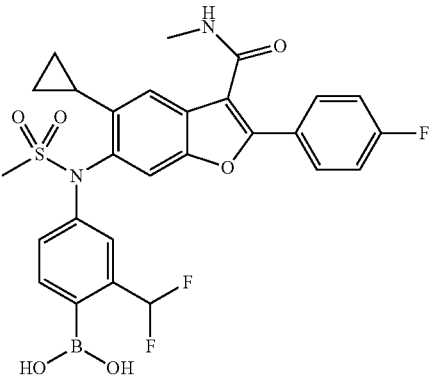 [SMILES: CNC(=O)c1c(-c2ccc(F)cc2)oc2cc(N(c3ccc(B(O)O)c(C(F)F)c3)S(C)(=O)=O)c(C3CC3)cc12]

Step 1: 2-(difluoromethyl)-4-fluoro-1-nitrobenzene

Diethylaminosulfur trifluoride (0.78 mL, 5.91 mmol) was added slowly to a 0° C. solution of 5-fluoro-2-nitrobenzaldehyde (1 g, 5.91 mmol) in dichloromethane (30 mL). The reaction mixture was stirred for 10 min at 0° C., 2.5 h at room temperature, cooled to 0° C. and quenched by the slow addition of saturated aqueous NaHCO$_3$. The aqueous layer was extracted with dichloromethane. The combined organic layers were dried (Na$_2$SO$_4$), filtered and evaporated to afford 2-(difluoromethyl)-4-fluoro-1-nitrobenzene (1.13 g, quant.) as a brown liquid. $^1$H NMR (400 MHz, CHLOROFORM-d) δ ppm 8.26 (dd, 1H), 7.60 (dd, 1H), 7.28-7.56 (m, 2H).

Step 2: 5-cyclopropyl-6-(N-(3-(difluoromethyl)-4-nitrophenyl)methylsulfonamido)-2-(4-fluorophenyl)-N-methylbenzofuran-3-carboxamide A solution of 5-cyclopropyl-2-(4-fluorophenyl)-N-methyl-6-(methylsulfonamido)benzofuran-3-carboxamide (1.00 g, 2.49 mmol), 2-(difluoromethyl)-4-fluoro-1-nitrobenzene (1.13 g, 5.91 mmol) and K$_2$CO$_3$ (0.85 g, 6.15 mmol) in HMPA (6.2 mL) was stirred at 60° C. for 15 h. The reaction mixture was diluted with EtOAc and water. The organic layer was washed with brine, dried (Na$_2$SO$_4$), filtered, evaporated and purified by silica gel chromatography (0-80% EtOAc/hexanes) to afford the title compound (1.45 g, 97%) as a yellow solid. LCMS (m/z, ES$^+$)=574.3 (M+H+).

Step 3: 6-(N-(4-amino-3-(difluoromethyl)phenyl) methylsulfonamido)-5-cyclopropyl-2-(4-fluorophenyl)-N-methylbenzofuran-3-carboxamide A solution of 5-cyclopropyl-6-(N-(3-(difluoromethyl)-4-nitrophenyl)methylsulfonamido)-2-(4-fluorophenyl)-N-methylbenzofuran-3-carboxamide (1.45 g, 2.53 mmol) and 10% Pd/C (catalytic) in MeOH (15 mL) was stirred under a hydrogen atmosphere (20 psi) for 3 h. The reaction mixture was filtered through celite, evaporated, and purified by silica gel chromatography (0-50% EtOAc/hexanes) to afford the title compound (0.87 g, 63%) as a white solid. LCMS (m/z, ES$^+$)= 544.3 (M+H+).

Step 4: 6-(N-(4-bromo-3-(difluoromethyl)phenyl) methylsulfonamido)-5-cyclopropyl-2-(4-fluorophenyl)-N-methylbenzofuran-3-carboxamide Sodium nitrite (0.12 g, 1.75 mmol) was added to a 0° C. solution of 6-(N-(4-amino-3-(difluoromethyl)phenyl)methylsulfonamido)-5-cyclopropyl-2-(4-fluorophenyl)-N-methylbenzofuran-3-carboxamide (0.87 g, 1.59 mmol) in acetonitrile (10 ml) and aq HBr (48%) (10 mL). The reaction mixture was stirred for 30 min at 0° C. and copper (I) bromide (0.27 g, 1.91 mmol) was added. The reaction mixture was stirred at 75° C. for 2 h and diluted with EtOAc and water. The organic layer was washed with brine, dried (Na$_2$SO$_4$), filtered, evaporated and purified by silica gel chromatography (0-50% EtOAc/hexanes) to afford the title compound (0.38 g, 39%) as a white foam. LCMS (m/z, ES$^+$)=607, 609 (M+H+).

Step 5: (4-(N-(5-cyclopropyl-2-(4-fluorophenyl)-3-(methylcarbamoyl)benzofuran-6-yl)methylsulfonamido)-2-(difluoromethyl)phenyl)boronic acid A solution of 6-(N-(4-bromo-3-(difluoromethyl)phenyl) methylsulfonamido)-5-cyclopropyl-2-(4-fluorophenyl)-N-methylbenzofuran-3-carboxamide (0.20 g, 0.33 mmol), potassium acetate (0.13 g, 1.32 mmol), PdCl$_2$(dppf)-CH$_2$Cl$_2$ adduct (0.027 g, 0.033 mmol), and bis(pinacolato)diboron (0.25 g, 0.99 mmol) in 1,4-dioxane (4.12 ml) was degassed, purged with nitrogen and heated at 80° C. for 3 h 45 mins. The reaction mixture was diluted with EtOAc and water, filtered through celite, and evaporated. The brown residue was dissolved in 10 mL THF, and 5 mL 1M HCl. NaIO$_4$ (0.56 g, 2.63 mmol) was added and the suspension was stirred for 1 h and diluted with EtOAc and water. The organic layer was washed with water, brine, dried (Na$_2$SO$_4$), filtered, evaporated and purified by reverse phase chromatography (5-100% CH$_3$CN/ H$_2$O (0.1% formic acid)) to afford the title compound (0.085 g, 45%) as a white solid. $^1$H NMR (400 MHz, METHANOL-d4) δ ppm 7.90-7.97 (m, 2H), 7.87 (s, 1H), 7.43-7.61 (m, 3H), 7.30 (s, 1H), 7.21-7.29 (m, 2H), 6.65-7.01 (m, 1H), 3.33 (s, 3H), 2.94 (s, 3H), 2.08-2.21 (m, 1H), 0.35-1.10 (m, 4H). LCMS (m/z, ES$^+$)=573.3 (M+H+).

Example 10

(4-(N-(5-cyclopropyl-2-(4-fluorophenyl)-3-(methylcarbamoyl)benzofuran-6-yl)methylsulfonamido)-2-(trifluoromethyl)phenyl)boronic acid

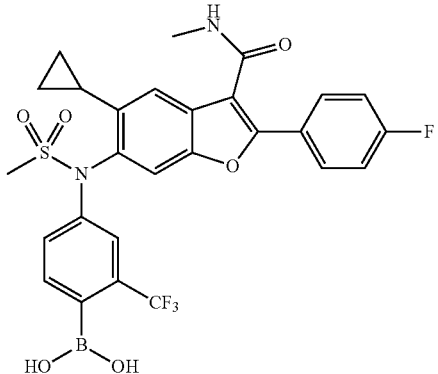 [SMILES: CNC(=O)c1c(-c2ccc(F)cc2)oc2cc(N(c3ccc(B(O)O)c(C(F)(F)F)c3)S(C)(=O)=O)c(C3CC3)cc12]

Step 1: 5-cyclopropyl-2-(4-fluorophenyl)-N-methyl-6-(N-(4-nitro-3-(trifluoromethyl)phenyl)methylsulfonamido)benzofuran-3-carboxamide A solution of 5-cyclopropyl-2-(4-fluorophenyl)-N-methyl-6-(methylsulfonamido)benzofuran-3-carboxamide (1.00 g, 2.49 mmol), 4-fluoro-1-nitro-2-(trifluoromethyl) benzene (1.04 g, 4.97 mmol), K$_2$CO$_3$ (1.03 g, 7.45 mmol) in HMPA (6.2 mL) was stirred at 60° C. for 15 h. The reaction mixture was diluted with EtOAc and water. The organic layer was washed with brine, dried (Na$_2$SO$_4$), filtered, evaporated and purified by silica gel chromatography (0-50% EtOAc/ hexanes) to afford the title compound (1.37 g, 93%) as an orange solid. LCMS (m/z, ES$^+$)=592.2 (M+H+).

Step 2: 6-(N-(4-amino-3-(trifluoromethyl)phenyl) methylsulfonamido)-5-cyclopropyl-2-(4-fluorophenyl)-N-methylbenzofuran-3-carboxamide A solution of 5-cyclopropyl-2-(4-fluorophenyl)-N-methyl-6-(N-(4-nitro-3-(trifluoromethyl)phenyl)methylsulfonamido)benzofuran-3-carboxamide (1.37 g, 2.31 mmol) and 10% Pd/C (catalytic) in MeOH (23 mL) was stirred under a hydrogen atmosphere (10 psi) for 1 h. The reaction mixture was filtered through celite, evaporated, and purified by silica gel chromatography (0-50% EtOAc/hexanes) to afford the title compound (1.3 g, quant.) as a white solid. LCMS (m/z, ES$^+$)=562.3 (M+H+).

Step 3: 6-(N-(4-bromo-3-(trifluoromethyl)phenyl) methylsulfonamido)-5-cyclopropyl-2-(4-fluorophenyl)-N-methylbenzofuran-3-carboxamide Sodium nitrite (0.18 g, 2.55 mmol) was added to a 0° C. solution of 6-(N-(4-amino-3-(trifluoromethyl)phenyl)methylsulfonamido)-5-cyclopropyl-2-(4-fluorophenyl)-N-methylbenzofuran-3-carboxamide (1.3 g, 2.32 mmol) in acetonitrile (14 ml) and aq HBr (48%) (14 mL). The reaction mixture was stirred for 30 min at 0° C. and copper (I) bromide (0.40 g, 2.78 mmol) was added. The reaction mixture was stirred at 60° C. for 1 h and diluted with EtOAc and water. The organic layer was washed with brine, dried ($Na_2SO_4$), filtered, evaporated and purified by silica gel chromatography (0-50% EtOAc/hexanes) to afford the title compound (1.06 g, 73%) as a white foam. LCMS (m/z, $ES^+$)=625.2, 627.2 (M+H+).

Step 4: (4-(N-(5-cyclopropyl-2-(4-fluorophenyl)-3-(methylcarbamoyl)benzofuran-6-yl)methylsulfonamido)-2-(trifluoromethyl)phenyl)boronic acid A solution of 6-(N-(4-bromo-3-(trifluoromethyl)phenyl) methylsulfonamido)-5-cyclopropyl-2-(4-fluorophenyl)-N-methylbenzofuran-3-carboxamide (0.20 g, 0.32 mmol), potassium acetate (0.13 g, 1.28 mmol), $PdCl_2$(dppf)-$CH_2Cl_2$ adduct (0.026 g, 0.032 mmol), bis(pinacolato)diboron (0.24 g, 0.96 mmol) in 1,4-dioxane (4 ml) was degassed, purged with nitrogen and heated at 80° C. for 4 h. The reaction mixture was diluted with EtOAc and water, filtered through celite, and evaporated. The brown residue was dissolved in 10 mL THF, and 5 mL 1M HCl. $NaIO_4$ (0.64 g, 3.20 mmol) was added and the suspension was stirred for 3 h and diluted with EtOAc and water. The organic layer was washed with water, brine, dried ($Na_2SO_4$), filtered, evaporated and purified by reverse phase chromatography (5-100% $CH_3CN/H_2O$ (0.1% formic acid)) to afford the title compound (0.092 g, 49%) as a white solid. $^1$H NMR (400 MHz, METHANOL-d4) δ ppm 7.85-8.00 (m, 3H), 7.59-7.72 (m, 2H), 7.47 (d, 1H), 7.29-7.34 (m, 1H), 7.20-7.29 (m, 2H), 3.35 (s, 3H), 2.94 (s, 3H), 2.12 (tt, 1H), 0.28-1.10 (m, 4H). LCMS (m/z, $ES^+$)=591.3 (M+H+).

Example 11

(4-(N-(5-cyclopropyl-2-(4-fluorophenyl)-3-(methylcarbamoyl)benzofuran-6-yl)methylsulfonamido)-2,6-difluorophenyl)boronic acid

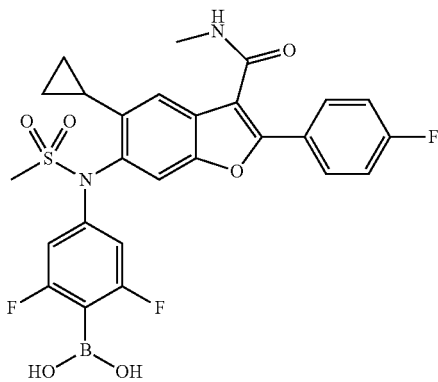 [SMILES: CNC(=O)c1c(-c2ccc(F)cc2)oc2cc(N(c3cc(F)c(B(O)O)c(F)c3)S(C)(=O)=O)c(C3CC3)cc12]

Step 1: 5-cyclopropyl-6-(N-(3,5-difluoro-4-nitrophenyl)methylsulfonamido)-2-(4-fluorophenyl)-N-methylbenzofuran-3-carboxamide A solution of 5-cyclopropyl-2-(4-fluorophenyl)-N-methyl-6-(methylsulfonamido)benzofuran-3-carboxamide (1.00 g, 2.49 mmol), 1,3,5-trifluoro-2-nitrobenzene (0.91 g, 5.11 mmol), $K_2CO_3$ (1.06 g, 7.67 mmol) in HMPA (7 mL) was stirred at 50° C. for 8 h. An additional portion of 1,3,5-trifluoro-2-nitrobenzene (0.91 g, 5.11 mmol) was added and the reaction mixture was stirred at 50° C. for another 15 h. The reaction mixture was diluted with EtOAc and water. The organic layer was washed with brine, dried ($Na_2SO_4$), filtered, and evaporated. The residue was taken up in 1:1 CH2Cl2:acetone. The desired isomer precipitated out and was collected by vacuum filtration and dried to afford the title compound (0.92 g, 65%) as a white solid. LCMS (m/z, $ES^+$)= 560.2 (M+H).

Step 2: 6-(N-(4-amino-3,5-difluorophenyl)methylsulfonamido)-5-cyclopropyl-2-(4-fluorophenyl)-N-methylbenzofuran-3-carboxamide A solution of 5-cyclopropyl-6-(N-(3,5-difluoro-4-nitrophenyl)methylsulfonamido)-2-(4-fluorophenyl)-N-methylbenzofuran-3-carboxamide (0.65 g, 1.16 mmol) and tin (II) chloride (0.66 g, 3.49 mmol) in EtOAc (10 mL) and ethanol (10 mL) was heated under reflux for 2 h. The reaction mixture was diluted with EtOAc and water and the suspension was filtered through celite. The organic layer was dried ($Na_2SO_4$), filtered, evaporated and purified by silica gel chromatography (0-50% EtOAc/hexanes) to afford the title compound (0.34 g, 55%) as a white solid. LCMS (m/z, $ES^+$)=530.2 (M+H+).

Step 3: 6-(N-(4-bromo-3,5-difluorophenyl)methylsulfonamido)-5-cyclopropyl-2-(4-fluorophenyl)-N-methylbenzofuran-3-carboxamide Sodium nitrite (0.034 g, 0.49 mmol) was added to a 0° C. solution of 6-(N-(4-amino-3,5-difluorophenyl)methylsulfonamido)-5-cyclopropyl-2-(4-fluorophenyl)-N-methylbenzofuran-3-carboxamide (0.235 g, 0.444 mmol) in Acetonitrile (3 ml) and aq HBr (48%) (3 mL). The reaction mixture was stirred for 30 min at 0° C. and copper (I) bromide (0.076 g, 0.53 mmol) was added. The reaction mixture was stirred at 90° C. for 2 h and diluted with EtOAc and water. The organic layer was washed with brine, dried ($Na_2SO_4$), filtered, evaporated and purified by silica gel chromatography (0-50% EtOAc/hexanes) to afford the title compound (0.094 g, 36%) as a white foam. LCMS (m/z, $ES^+$)=593.2, 595.2 (M+H+).

Step 4: (4-(N-(5-cyclopropyl-2-(4-fluorophenyl)-3-(methylcarbamoyl)benzofuran-6-yl)methylsulfonamido)-2,6-difluorophenyl)boronic acid A solution of 6-(N-(4-bromo-3,5-difluorophenyl)methylsulfonamido)-5-cyclopropyl-2-(4-fluorophenyl)-N-methylbenzofuran-3-carboxamide (0.093 g, 0.157 mmol), potassium acetate (0.062 g, 0.627 mmol), $PdCl_2$(dppf)-$CH_2Cl_2$ adduct (0.013 g, 0.016 mmol), bis(pinacolato)diboron (0.080 g, 0.31 mmol) in 1,4-Dioxane (1.6 ml) was degassed, purged with nitrogen and heated at 90° C. for 4 h. The reaction mixture was diluted with EtOAc and water, filtered through celite, and evaporated. The brown residue was dissolved in 5 mL THF, and 2.5 mL 1M HCl. $NaIO_4$ (0.27 g, 1.25 mmol) was added and the suspension was stirred for 2.5 h and diluted with EtOAc and water. The organic layer was washed with water, brine, dried ($Na_2SO_4$), filtered, evaporated and purified by reverse phase chromatography (5-100% $CH_3CN/H_2O$ (0.1% formic acid)) to afford the title compound (0.017 g, 19%) as a white solid. $^1$H NMR (400 MHz, METHANOL-d4) δ ppm 7.91-7.98 (m, 2H), 7.79 (s, 1H), 7.34 (s, 1H), 7.20-7.29 (m, 2H), 6.82-6.92 (m, 2H), 3.38 (s, 3H), 2.95 (s, 3H), 2.01-2.11 (m, 1H), 0.70-1.07 (m, 3H), 0.54 (br. s., 1H). LCMS (m/z, ES$^+$)=559.3 (M+H+).

Example 12

(2-cyano-4-(N-(5-cyclopropyl-2-(4-fluorophenyl)-3-(methylcarbamoyl)benzofuran-6-yl)methylsulfonamido)phenyl)boronic acid

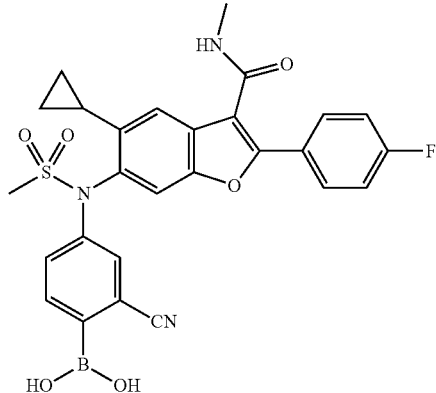 [SMILES: CNC(=O)c1c(-c2ccc(F)cc2)oc2cc(N(c3ccc(B(O)O)c(C#N)c3)S(C)(=O)=O)c(C3CC3)cc12]

Step 1: 6-(N-(3-cyano-4-nitrophenyl)methylsulfonamido)-5-cyclopropyl-2-(4-fluorophenyl)-N-methylbenzofuran-3-carboxamide A mixture of 5-fluoro-2-nitrobenzonitrile (1.280 mL, 11.18 mmol), 5-cyclopropyl-2-(4-fluorophenyl)-N-methyl-6-(methylsulfonamido)benzofuran-3-carboxamide (3.0 g, 7.45 mmol) and K$_2$CO$_3$ (3.09 g, 22.36 mmol) in 1,2-dimethoxyethane (30 mL) and water (7.5 mL) in a seal tube was heated to 80° C. overnight. It was cooled down to room temperature, diluted with EtOAc, filtered and the off-white solid was washed with water and then dried in vacuo to give crude desired product as a yellow solid (80% purity, 3.9 g, 76%). LCMS (m/z, ES$^+$)=549 (M+H+)

Step 2: 6-(N-(4-amino-3-cyanophenyl)methylsulfonamido)-5-cyclopropyl-2-(4-fluorophenyl)-N-methylbenzofuran-3-carboxamide A solution of Na$_2$S$_2$O$_4$ (7.24 g, 41.6 mmol) in water (70 mL) was added dropwise to a solution of 6-(N-(3-cyano-4-nitrophenyl)methylsulfonamido)-5-cyclopropyl-2-(4-fluorophenyl)-N-methylbenzofuran-3-carboxamide (3.8 g, 6.93 mmol) in THF at room temperature under N$_2$. The mixture was stirred overnight. H$_2$O was added to the mixture and then extracted with EtOAc. The combined extracts were washed with brine, dried over Na$_2$SO$_4$. After concentration, the crude residue was purified by chromatography on silica gel eluted with 0-20% EtOAC in DCM to give the desired product as a white solid (2.67 g, 74.3%). LCMS (m/z, ES$^+$)=519 (M+H+)

Step 3: 6-(N-(4-bromo-3-cyanophenyl)methylsulfonamido)-5-cyclopropyl-2-(4-fluorophenyl)-N-methylbenzofuran-3-carboxamide tBuNO$_2$ (0.859 ml, 7.23 mmol) was added dropwise to a solution of CuBr$_2$ (1.292 g, 5.79 mmol) in acetonitrile (10 mL). The mixture was heated to 50° C. for 10 min and then a suspension of 6-(N-(4-amino-3-cyanophenyl)methylsulfonamido)-5-cyclopropyl-2-(4-fluorophenyl)-N-methylbenzofuran-3-carboxamide (1.5 g, 2.89 mmol) in acetonitrile (40 mL) was added portions to above solution. It was stirred for 30 min at 50° C. and then cooled to room temperature. The reaction was quenched with ice-cooled 1N HCl and then extracted with EtOAc. The combined extracts were washed with 10% Na$_2$S$_2$O$_3$ and brine, and then dried over Na$_2$SO$_4$. After concentration, the crude residue was purified by chromatography on silica gel eluted with 0-5% EtOAC in DCM to give the desired product as a white foam (1.18 g, 70%). LCMS (m/z, ES$^+$)=583 (M+H+)

Step 4: 6-(N-(3-cyano-4-(4,4,5,5-tetramethyl-1,3,2-dioxaborolan-2-yl)phenyl)methylsulfonamido)-5-cyclopropyl-2-(4-fluorophenyl)-N-methylbenzofuran-3-carboxamide A mixture of 6-(N-(4-bromo-3-cyanophenyl)methylsulfonamido)-5-cyclopropyl-2-(4-fluorophenyl)-N-methylbenzofuran-3-carboxamide (100 mg, 0.172 mmol), potassium acetate (67.4 mg, 0.687 mmol), bis(pinacolato)diboron (87 mg, 0.343 mmol) and bis(tricyclohexylphosphine)palladium (II) dichloride (12.67 mg, 0.017 mmol) in 1,4-dioxane (2.0 ml) was maintained at 90° C. in a sealed tube under N$_2$ overnight. The mixture was allowed to cool to room temperature, diluted with EtOAc, filtered through a pad of silic gel and celite and then concentrated to dryness to give the crude product as tan foam which was used for the next step without further purification. LCMS (m/z, ES$^+$)=630 (M+H+).

Step 5: (2-cyano-4-(N-(5-cyclopropyl-2-(4-fluorophenyl)-3-(methylcarbamoyl)benzofuran-6-yl)methylsulfonamido)phenyl)boronic acid The crude 6-(N-(3-cyano-4-(4,4,5,5-tetramethyl-1,3,2-dioxaborolan-2-yl)phenyl)methylsulfonamido)-5-cyclopropyl-2-(4-fluorophenyl)-N-methylbenzofuran-3-carboxamide (108 mg, 0.172 mmol) was dissolved in tetrahydrofuran (4.0 mL). 1M HCl (2.059 mL, 1.029 mmol) was added followed by sodium periodate (294 mg, 1.373 mmol). The mixture was stirred at room temperature overnight. The reaction was partitioned between EtOAc and water. The aqueous layer was extracted with EtOAc (2×). The organic phase was washed with 10% aq. Na$_2$S$_2$O$_3$, brine, and dried over Na$_2$SO$_4$. After concentration, the crude residue was purified by reverse phase HPLC (10-100% MeCN/H$_2$O with 0.1% TFA) to give the title compound as a white solid (58 mg, 62%). $^1$H NMR (400 MHz, DMSO-d$_6$) δ ppm 8.60 (br. s., 1H) 8.48 (q, 1H) 8.12 (s, 1H) 7.94-8.02 (m, 2H) 7.73-7.80 (m, 2H) 7.58-7.65 (m, 1H) 7.41 (t, 2H) 7.21 (s, 1H) 3.46 (s, 3H) 2.84

(d, 3H) 2.03-2.14 (m, 1H) 0.99 (br. s., 1H) 0.85 (br. s., 2H) 0.45 (br. s., 1H). LCMS (m/z, ES+)=548 (M+H+).

Example 13

6-(N-(4-borono-3-chlorophenyl)methylsulfonamido)-2-(4-chlorophenyl)-5-cyclopropylbenzofuran-3-carboxylic acid

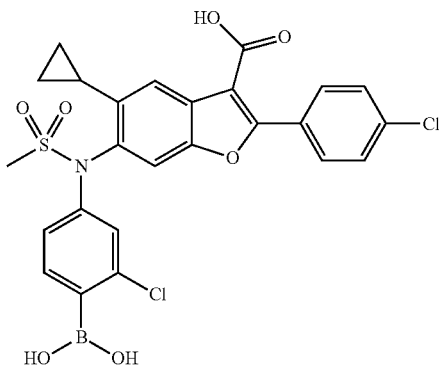 [SMILES: CS(=O)(=O)N(c1ccc(B(O)O)c(Cl)c1)c1cc2oc(-c3ccc(Cl)cc3)c(C(=O)O)c2cc1C1CC1]

Step 1: ethyl 6-((4-bromo-3-chlorophenyl)amino)-2-(4-chlorophenyl)-5-cyclopropylbenzofuran-3-carboxylate NEt$_3$ (0.490 mL, 3.51 mmol) was added to a suspension of (4-bromo-3-chlorophenyl)boronic acid (364 mg, 1.546 mmol) in DCM (7 mL) and the resulting solution was added dropwise to mixture of ethyl 6-amino-2-(4-chlorophenyl)-5-cyclopropylbenzofuran-3-carboxylate (500 mg, 1.405 mmol), copper(II) acetate (281 mg, 1.546 mmol), 3 Å molecular sieves (1 g) and NEt$_3$ (0.490 mL, 3.51 mmol) in DCM (7 mL) stirring vigorously at RT open to the air in a flask equipped with a drying tube. After stirring for 4 h at RT, another solution of NEt$_3$ (0.490 mL, 3.51 mmol) and (4-bromo-3-chlorophenyl)boronic acid (364 mg, 1.546 mmol) in DCM (7 mL) was added dropwise to the reaction mixture, followed by more copper(II) acetate (281 mg, 1.546 mmol). The reaction mixture was stirred for 3 d and more solution of NEt$_3$ (0.490 mL, 3.51 mmol) and (4-bromo-3-chlorophenyl)boronic acid (364 mg, 1.546 mmol) in DCM (7 mL) was added dropwise with further addition of copper(II) acetate (281 mg, 1.546 mmol). After 2 h, EtOAc was added followed by Celite. The mixture was stirred for 30 min then filtered through a pad of Celite and the brown solution was concentrated to dryness. EtOAc was added followed by water. The organic layer was separated, washed with water, brine, dried over MgSO$_4$, filtered and concentrated. The crude product was purified on silica gel (hex/EtOAc) to give ethyl 6-((4-bromo-3-chlorophenyl)amino)-2-(4-chlorophenyl)-5-cyclopropylbenzofuran-3-carboxylate (685 mg, 1.231 mmol, 88% yield) as an orange foam. $^1$H NMR (400 MHz, DMSO-d$_6$) δ ppm 8.17 (s, 1H), 7.98-8.07 (m, 2H), 7.58-7.65 (m, 3H), 7.49-7.56 (m, 2H), 7.11 (d, 1H), 6.87 (dd, 1H), 4.36 (q, 2H), 1.95-2.12 (m, 1H), 1.36 (t, 3H), 0.93-1.05 (m, 2H), 0.57-0.71 (m, 2H).

Step 2: ethyl 6-(N-(4-bromo-3-chlorophenyl)methylsulfonamido)-2-(4-chlorophenyl)-5-cyclopropylbenzofuran-3-carboxylate A 1M solution of LiHMDS in THF (1.049 mL, 1.049 mmol) was added dropwise to a solution of ethyl 6-((4-bromo-3-chlorophenyl)amino)-2-(4-chlorophenyl)-5-cyclopropylbenzofuran-3-carboxylate (440 mg, 0.807 mmol) in THF (15 mL) at −78° C. After stirring for 45 min, the red solution was added dropwise via cannula to a solution of MsCl (0.252 mL, 3.23 mmol) in THF (1 mL) at −78° C. Upon complete addition the yellow solution was allowed to warm to RT and stirred overnight. Water (150 mL) and EtOAc (150 mL) were added. The organic layer was separated and washed with water, brine, dried over MgSO$_4$, filtered and concentrated. The crude product was purified on silica gel (hex/EtOAc) to give ethyl 6-(N-(4-bromo-3-chlorophenyl)methylsulfonamido)-2-(4-chlorophenyl)-5-cyclopropylbenzofuran-3-carboxylate (259 mg, 0.395 mmol, 49% yield). $^1$H NMR (400 MHz, DMSO-d$_6$)$_6$ ppm 8.22 (s, 1H), 8.05 (d, 2H), 7.78 (d, 1H), 7.64-7.71 (m, 3H), 7.62 (s, 1H), 7.31 (dd, 1H), 4.35 (q, 2H), 3.46 (s, 3H), 2.10-2.22 (m, 1H), 1.34 (t, 3H), 0.69-1.13 (m, 3H), 0.42 (br. s., 1H).

Step 3: 6-(N-(4-bromo-3-chlorophenyl)methylsulfonamido)-2-(4-chlorophenyl)-5-cyclopropylbenzofuran-3-carboxylic acid A 1M solution of NaOH (1.877 mL, 1.877 mmol) was added to a solution of ethyl 6-(N-(4-bromo-3-chlorophenyl)methylsulfonamido)-2-(4-chlorophenyl)-5-cyclopropylbenzofuran-3-carboxylate (234 mg, 0.375 mmol) in THF (2 mL) and MeOH (1 mL) at RT. After 1 h a white precipitate formed but starting material is still evident by LCMS. THF (3 mL) and a 4N solution of NaOH (1 mL) were added and the mixture was heated to 60° C. for 4 h. EtOAc was added and the aqueous layer was made acidic with the addition of 1N HCl. The organic layer was separated, washed with water, brine, dried over Na$_2$SO$_4$, filtered and concentrated to give 6-(N-(4-bromo-3-chlorophenyl)methylsulfonamido)-2-(4-chlorophenyl)-5-cyclopropylbenzofuran-3-carboxylic acid (220 mg, 0.351 mmol, 94% yield) as a white solid. LCMS (m/z, ES+)=594.0 (M−H).

Step 4: 6-(N-(3-chloro-4-(4,4,5,5-tetramethyl-1,3,2-dioxaborolan-2-yl)phenyl)methylsulfonamido)-2-(4-chlorophenyl)-5-cyclopropylbenzofuran-3-carboxylic acid A flask containing 6-(N-(4-bromo-3-chlorophenyl)methylsulfonamido)-2-(4-chlorophenyl)-5-cyclopropylbenzofuran-3-carboxylic acid (100 mg, 0.168 mmol), 4,4,4',4',5,5,5',5'-octamethyl-2,2'-bi(1,3,2-dioxaborolane) (85 mg, 0.336 mmol), potassium acetate (65.9 mg, 0.672 mmol) and PdCl$_2$(dppf)-CH$_2$Cl$_2$ adduct (13.72 mg, 0.017 mmol) was evacuated and purged with nitrogen (2×) then 1,4-Dioxane (4 mL) was added and the mixture was heated to 90° C. under nitrogen for 16 h. The reaction was cooled to RT, diluted with EtOAc, filtered through Celite and water was added. The organic layer was separated, dried over Na$_2$SO$_4$, filtered and concentrated to dryness. The crude product was used as is in next step.

Step 5: 6-(N-(4-borono-3-chlorophenyl)methylsulfonamido)-2-(4-chlorophenyl)-5-cyclopropylbenzofuran-3-carboxylic acid A solution of 6-(N-(3-chloro-4-(4,4,5,5-tetramethyl-1,3,2-dioxaborolan-2-yl)phenyl)methylsulfonamido)-2-(4-chlorophenyl)-5-cyclopropylbenzofuran-3-carboxylic acid (110 mg, 0.171 mmol) and sodium periodate (183 mg, 0.856 mmol) in THF (14 mL) and aqueous 1N HCl (7 mL) was stirred at RT for 4 h then water and EtOAc were added. The organic layer was separated, washed with brine, dried over Na$_2$SO$_4$, filtered and concentrated. The crude product was purified by Reverse Phase HPLC (water/ACN+0.1% formic acid) to give 6-(N-(4-borono-3-chlorophenyl)methylsulfonamido)-2-(4-chlorophenyl)-5-cyclopropylbenzofuran-3-carboxylic acid (24 mg, 0.041 mmol, 24% yield) as a white powder. $^1$H NMR (400 MHz, DMSO-d$_6$) δ ppm 13.31 (br. s., 1H), 8.33 (s, 2H), 8.16 (s, 1H), 8.03 (d, 2H), 7.52-7.70 (m, 3H), 7.37-7.48 (m, 2H), 7.34 (dd, 1H), 3.40 (s, 3H), 2.09-2.22 (m, 1H), 0.64-1.11 (m, 3H), 0.47 (br. s., 1H). LCMS (m/z, ES$^+$)=558.1 (M−H).

Example 14

(4-(N-(3-carbamoyl-2-(4-chlorophenyl)-5-cyclopropylbenzofuran-6-yl)methylsulfonamido)-2-chlorophenyl)boronic acid

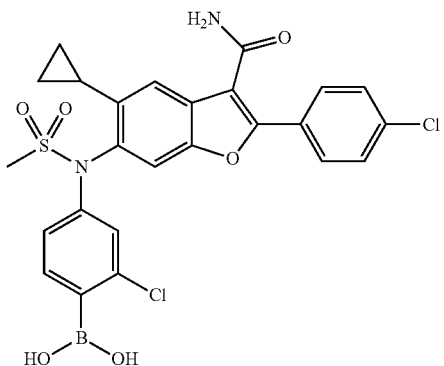 [SMILES: CS(=O)(=O)N(c1ccc(B(O)O)c(Cl)c1)c1cc2oc(-c3ccc(Cl)cc3)c(C(N)=O)c2cc1C1CC1]

HATU (27.1 mg, 0.071 mmol) was added to a solution of 6-(N-(4-borono-3-chlorophenyl)methylsulfonamido)-2-(4-chlorophenyl)-5-cyclopropylbenzofuran-3-carboxylic acid (20 mg, 0.036 mmol) and Hunig's base (0.031 mL, 0.179 mmol) in DMF (3 mL). After stirring for 1 h at RT, a 2M solution of ammonia in MeOH (0.357 mL, 0.714 mmol) was added and the solution was stirred for 16 h. Water and EtOAc were added. The organic layer was separated, washed with water, brine, dried over Na2SO4, filtered and concentrated. The crude product was purified by Reverse Phase HPLC (water/MeCN+0.1% formic acid) to give (4-(N-(3-carbamoyl-2-(4-chlorophenyl)-5-cyclopropylbenzofuran-6-yl)methylsulfonamido)-2-chlorophenyl)boronic acid (9 mg, 0.015 mmol, 43% yield) as a white powder. $^1$H NMR (400 MHz, DMSO-d$_6$) δ ppm 8.33 (s, 2H), 8.12 (s, 1H), 8.05 (s, 1H), 7.94-8.01 (m, 2H), 7.80 (s, 1H), 7.59-7.68 (m, 2H), 7.41-7.46 (m, 1H), 7.39 (d, 1H), 7.30-7.37 (m, 1H), 7.23 (s, 1H), 3.41 (s, 3H), 2.05-2.21 (m, 1H), 1.02 (br. s., 1H), 0.83 (br. s., 2H), 0.53 (br. s., 1H). LCMS (m/z, ES+)=559.2 (M+H+).

Example 15

6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide

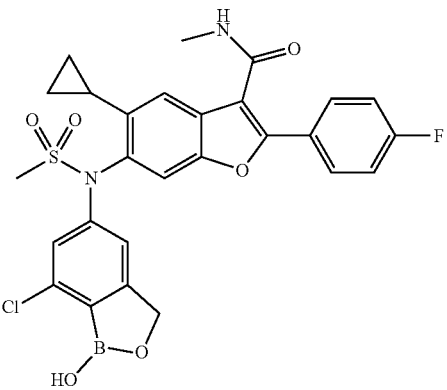 [SMILES: CNC(=O)c1c(-c2ccc(F)cc2)oc2cc(N(c3cc(Cl)c4c(c3)COB4O)S(C)(=O)=O)c(C3CC3)cc12]

Step 1: methyl 5-(N-(5-cyclopropyl-2-(4-fluorophenyl)-3-(methylcarbamoyl)benzofuran-6-yl)methylsulfonamido)-2-nitrobenzoate A solution of 5-cyclopropyl-2-(4-fluorophenyl)-N-methyl-6-(methylsulfonamido)benzofuran-3-carboxamide (1.0 g, 2.49 mmol), methyl 5-fluoro-2-nitrobenzoate (0.99 g, 4.97 mmol), and potassium carbonate (1.03 g, 7.45 mmol) in HMPA (6.2 mL) was stirred at 60° C. for 3 days. The solution was diluted with EtOAc and water and the organic layer was washed with brine, dried (Na$_2$SO$_4$), filtered, evaporated and purified by silica gel chromatography (0-80% EtOAc/hexanes) to afford the title compound (1.33 g, 92%) as a yellow solid. $^1$H NMR (400 MHz, CHLOROFORM-d) δ ppm 7.99 (d, J=9.09 Hz, 1H), 7.85-7.92 (m, 2H), 7.56 (s, 1H), 7.53 (s, 1H), 7.50 (dd, J=9.09, 2.64 Hz, 1H), 7.43 (d, J=2.64 Hz, 1H), 7.19-7.26 (m, 2H), 5.80 (d, J=4.59 Hz, 1H), 3.90 (s, 3H), 3.34 (s, 3H), 3.02 (d, J=4.98 Hz, 3H), 1.91 (tt, J=8.37, 5.31 Hz, 1H), 1.01 (br. s., 1H), 0.89 (br. s., 1H), 0.73-0.85 (m, 1H), 0.58 (br. s., 1H).

Step 2: methyl 2-amino-5-(N-(5-cyclopropyl-2-(4-fluorophenyl)-3-(methylcarbamoyl)benzofuran-6-yl)methylsulfonamido)benzoate A solution of methyl 5-(N-(5-cyclopropyl-2-(4-fluorophenyl)-3-(methylcarbamoyl)benzofuran-6-yl)methylsulfonamido)-2-nitrobenzoate (1.33 g, 2.29 mmol) and 10% Pd/C (cat.) in MeOH (20 mL) was stirred under a hydrogen atmosphere (15 psi) for 1.5 h. The solution was filtered through celite and evaporated to afford the title compound (1.26 g, quant.) as a light yellow solid that was used without further purification.

Step 3: methyl 2-amino-3-chloro-5-(N-(5-cyclopropyl-2-(4-fluorophenyl)-3-(methylcarbamoyl)benzofuran-6-yl)methylsulfonamido)benzoate A solution of methyl 2-amino-5-(N-(5-cyclopropyl-2-(4-fluorophenyl)-3-(methylcarbamoyl)benzofuran-6-yl)methylsulfonamido)benzoate (1.60 g, 2.91 mmol) and NCS (0.39 g, 2.91 mmol) in 80 mL CH₃CN was stirred at 40° C. for 30 mins. Additional NCS (0.39 g, 2.91 mmol) was added, the reaction mixture was heated at 40° C. for another 30 mins, evaporated onto silica gel, and purified by silica gel chromatography (0-70% EtOAc/hexanes) to afford the title compound (1.29 g, 76%) as a light pink solid. ¹H NMR (400 MHz, CHLOROFORM-d) δ ppm 8.00 (d, J=2.54 Hz, 1H), 7.85-7.92 (m, 2H), 7.71 (s, 1H), 7.65 (d, J=2.63 Hz, 1H), 7.43 (s, 1H), 7.15-7.22 (m, 2H), 6.36 (br. s., 2H), 5.85 (d, J=4.78 Hz, 1H), 3.87 (s, 3H), 3.19 (s, 3H), 2.98 (d, J=4.88 Hz, 3H), 2.15-2.30 (m, 1H), 0.31-1.11 (m, 4H).

Step 4: methyl 2-bromo-3-chloro-5-(N-(5-cyclopropyl-2-(4-fluorophenyl)-3-(methylcarbamoyl)benzofuran-6-yl)methylsulfonamido)benzoate Sodium nitrite (0.17 g, 2.42 mmol) was added to a 0° C. solution of methyl 2-amino-3-chloro-5-(N-(5-cyclopropyl-2-(4-fluorophenyl)-3-(methylcarbamoyl)benzofuran-6-yl)methylsulfonamido)benzoate (1.29 g, 2.20 mmol) in acetonitrile (7.3 ml) and 48% aqueous HBr (7.3 ml) at 0° C. and the reaction mixture was stirred at 0° C. for 30 mins, Copper(I) bromide (0.38 g, 2.64 mmol) was added and the solution was heated at 50° C. for 30 mins. The reaction mixture was cooled to RT, diluted with EtOAc and water. The organic layer was washed with brine, dried (Na₂SO₄), filtered, evaporated and purified by silica gel chromatography (0-50% EtOAc/hexanes) to afford the title compound (1.24 g, 86%) as a white foam. ¹H NMR (400 MHz, CHLOROFORM-d) δ ppm 7.86-7.93 (m, 2H), 7.50-7.63 (m, 4H), 7.17-7.25 (m, 2H), 5.79 (br. s., 1H), 3.92 (s, 3H), 3.28 (s, 3H), 3.01 (d, J=4.88 Hz, 3H), 1.94-2.04 (m, 1H), 0.76-1.09 (m, 3H), 0.55 (br. s., 1H).

Step 5: 6-(N-(4-bromo-3-chloro-5-((methoxymethoxy)methyl)phenyl)methylsulfonamido)-5-cyclopropyl-2-(4-fluorophenyl)-N-methylbenzofuran-3-carboxamide LiBH₄ (2.85 ml, 5.71 mmol) solution (2M in THF) was added dropwise to a 0° C. solution of methyl 2-bromo-3-chloro-5-(N-(5-cyclopropyl-2-(4-fluorophenyl)-3-(methylcarbamoyl)benzofuran-6-yl)methylsulfonamido)benzoate (1.24 g, 1.90 mmol) in Tetrahydrofuran (THF) (13.5 ml) and Methanol (1.3 ml). The reaction mixture was stirred at 0° C. for 1 h and quenched with 1M NaOH. The reaction mixture was diluted with EtOAc and water. The organic layer was washed with brine, dried (Na₂SO₄), filtered and evaporated. The crude alcohol was taken up in THF (14 mL). DIEA (1.0 ml, 5.71 mmol) and MOM-Cl (0.36 ml, 4.76 mmol) were added and the reaction mixture was stirred at 50° C. overnight. Sat'd NaHCO₃ was added and the mixture was extracted with EtOAc. The organic layer was washed with brine, dried (Na₂SO₄), filtered, evaporated and purified by silica gel chromatography (0-50% EtOAc/hexanes) to obtain the title compound (1.08 g, 85%) as a white foam. ¹H NMR (400 MHz, CHLOROFORM-d) δ ppm 7.86-7.93 (m, 2H), 7.61 (s, 1H), 7.50 (d, 1H), 7.49 (s, 1H), 7.42 (d, J=2.83 Hz, 1H), 7.18-7.25 (m, 2H), 5.80 (br. s., 1H), 4.73 (s, 2H), 4.62 (s, 2H), 3.38 (s, 3H), 3.27 (s, 3H), 3.01 (d, J=4.98 Hz, 3H), 2.05-2.14 (m, 1H), 0.75-1.11 (m, 3H), 0.58 (br. s., 1H).

Step 6: 6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide A solution of 6-(N-(4-bromo-3-chloro-5-((methoxymethoxy)methyl)phenyl)methylsulfonamido)-5-cyclopropyl-2-(4-fluorophenyl)-N-methylbenzofuran-3-carboxamide (0.25 g, 0.38 mmol), potassium acetate (0.15 g, 1.50 mmol), PdCl₂(dppf)-CH₂Cl₂ adduct (0.031 g, 0.038 mmol), bis(pinacolato)diboron (0.29 g, 1.13 mmol) in 1,4-Dioxane (3.75 ml) was degassed, purged with nitrogen and heated at 90° C. for 15 h. The reaction mixture was diluted with EtOAc and water, filtered through celite, and evaporated. The brown residue was dissolved in THF (5 mL), and 1M HCl (5 mL) and the solution was heated at 70° C. for 4 h. MeOH (2 mL) was added and the solution was heated at 70° C. for another 15 h and diluted with EtOAc and water. The organic layer was washed with brine, dried (Na₂SO₄), filtered, evaporated and purified by silica gel chromatography (100% EtOAc to 10% MeOH/CH₂Cl₂) to obtain the title compound as a clear oil. MeOH was added and the precipitate was collected by vacuum filtration, washed with MeOH and dried to afford the title compound (0.0831 g, 39%) as a light tan solid. The filtrate was purified by reverse phase chromatography (5-100% CH₃CN/H₂O (0.1% formic acid)) to afford an additional batch of the title compound (0.0146 g, 7%) as a white solid. ¹H NMR (400 MHz, DMSO-d6) δ ppm 9.17 (s, 1H), 8.50 (d, J=4.68 Hz, 1H), 8.09 (s, 1H), 7.94-8.02 (m, 2H), 7.37-7.46 (m, 3H), 7.28 (d, J=1.56 Hz, 1H), 7.22 (s, 1H), 4.96 (s, 2H), 3.47 (s, 3H), 2.84 (d, J=4.59 Hz, 3H), 2.02-2.14 (m, 1H), 0.98 (br. s., 1H), 0.82 (br. s., 2H), 0.49 (br. s., 1H). LCMS (m/z, ES⁺)=569.2 (M+H+).

Example 16

(4-(N-(5-cyclopropyl-2-(4-fluorophenyl)-3-(methylcarbamoyl)benzofuran-6-yl)methylsulfonamido)-2-(methylsulfonyl)phenyl)boronic acid

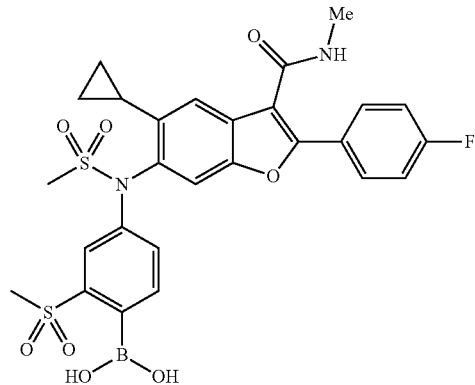 [SMILES: CNC(=O)c1c(-c2ccc(F)cc2)oc2cc(N(c3ccc(B(O)O)c(S(C)(=O)=O)c3)S(C)(=O)=O)c(C3CC3)cc12]

Step 1: 5-cyclopropyl-2-(4-fluorophenyl)-N-methyl-6-(N-(3-(methylthio)-4-nitrophenyl)methylsulfonamido)benzofuran-3-carboxamide A mixture of 6-(N-(3-chloro-4-nitrophenyl)methylsulfonamido)-5-cyclopropyl-2-(4-fluorophenyl)-N-methylbenzofuran-3-carboxamide (2 g, 3.58 mmol), and sodium thiomethoxide (0.685 g, 9.78 mmol) was dissolved in 20 mL of 1:1 CH₃CN/Isopropanol and was stirred at room temperature for 3 h. Solvent was evaporated and water (60 mL) was added. The yellowish solid formed was filtered, washed with water to provide light yellowish solid which was used in the next step. (1.6 g, 86%) LCMS (m/z, ES⁺)=570 (M+H+).

Step 2: 5-cyclopropyl-2-(4-fluorophenyl)-N-methyl-6-(N-(3-(methylsulfonyl)-4-nitrophenyl)methylsulfonamido)benzofuran-3-carboxamide To 5-cyclopropyl-2-(4-fluorophenyl)-N-methyl-6-(N-(3-(methylthio)-4-nitrophenyl)methylsulfonamido)benzofuran-3-carboxamide (1 g, 1.756 mmol) in acetic acid (5 mL) was carefully added $H_2O_2$ (1.630 mL, 15.96 mmol). The reaction mixture was stirred at 90° C. for 5 h. The resulting yellow suspension was concentrated and cooled in an ice bath and sat $NaHCO_3$ was added. The resulting yellow solid was filtered, washed 3 times (3×15 mL) with water and dried. This material was used in the next step. (0.8 g, 83%). LCMS (m/z, $ES^+$)=602 (M+H+).

Step 3: 6-(N-(4-amino-3-(methylsulfonyl)phenyl)methylsulfonamido)-5-cyclopropyl-2-(4-fluorophenyl)-N-methylbenzofuran-3-carboxamide To a solution of 5-cyclopropyl-2-(4-fluorophenyl)-N-methyl-6-(N-(3-(methylsulfonyl)-4-nitrophenyl)methylsulfonamido)benzofuran-3-carboxamide (0.7 g, 1.164 mmol) in 1:1 EtOH/Ethyl acetate (10 mL) was added tin(II) chloride (1.324 g, 6.98 mmol). The reaction was heated at 70° C. for 3 h. Solvent was evaporated and the reaction was partitioned between EtOAc and water. The resulting semi viscous mass was filtered (6 h) and the solid obtained (0.5 g, 75%) was progressed as is to the next step. LCMS (m/z, $ES^+$)=572 (M+H+).

Step 4: 6-(N-(4-bromo-3-(methylsulfonyl)phenyl)methylsulfonamido)-5-cyclopropyl-2-(4-fluorophenyl)-N-methylbenzofuran-3-carboxamide To a solution of 6-(N-(4-amino-3-(methylsulfonyl)phenyl)methylsulfonamido)-5-cyclopropyl-2-(4-fluorophenyl)-N-methylbenzofuran-3-carboxamide (0.4 g, 0.700 mmol) in acetonitrile (3 mL) was added 8M HBr (0.437 mL, 3.50 mmol). The resulting solution was cooled in an ice water bath for 15 minutes and the mixture was treated with a solution of sodium nitrite (0.072 g, 1.050 mmol) in water (2 mL) over 5 min. The resulting yellow suspension was stirred in an ice bath for 1.5 hours and then treated with copper(I) bromide (0.201 g, 1.399 mmol) in small portions over 5 minutes. This dark brown solution that was warmed to 60° C. and stirring continued for additional 2 h. The mixture was cooled to RT and poured into a mixture of 5% aqueous sodium bisulfite (6 mL) and EtOAc (80 mL). The phases were separated and the aqueous solution extracted with two additional 15 mL portions of EtOAc. The combined EtOAc solutions were washed with 5% aqueous sodium bisulfite, saturated aqueous sodium bicarbonate, saturated brine, dried over sodium sulfate and concentrated to dryness at reduced pressure to give a yellow foam. This material was subjected to flash chromatography (silica gel, gradient from 9:1 hexane/EtOAc to EtOAc) to afford the title compound (0.3 g, 68%). LCMS (m/z, $ES^+$) =635, 637 (M+H+).

Step 5: (4-(N-(5-cyclopropyl-2-(4-fluorophenyl)-3-(methylcarbamoyl)benzofuran-6-yl)methylsulfonamido)-2-(methylsulfonyl)phenyl)boronic acid To a solution of 6-(N-(4-bromo-3-(methylsulfonyl)phenyl)methylsulfonamido)-5-cyclopropyl-2-(4-fluorophenyl)-N-methylbenzofuran-3-carboxamide (200 mg, 0.315 mmol) in 1,4-Dioxane (2 mL) wad added 4,4,4',4',5,5,5',5'-octamethyl-2,2'-bi(1,3,2-dioxaborolane) (400 mg, 1.574 mmol), potassium acetate (154 mg, 1.574 mmol) and Pd(II)(dppf)Cl$_2$ DCM complex (12.85 mg, 0.016 mmol). The mixture was stirred under nitrogen at 80° C. After 4 hours the mixture was cooled to RT and diluted with EtOAc (10 mL). The resulting solution was washed with water, saturated brine, and dried over sodium sulfate. After evaporation of the solvent, the crude residue was dissolved in 10 mL of THF and the resulting solution cooled in an ice water bath. The solution was treated with 1N aqueous HCl (1.574 mL, 1.574 mmol) followed by sodium periodate (135 mg, 0.629 mmol). The mixture was stirred at 0° C. for 20 minutes and then allowed to warm to RT. After 18 hours, the mixture was partitioned between water and EtOAc and the phases separated. The aqueous solution was extracted with EtOAc. The combined EtOAc solutions were washed with 5% aqueous sodium bisulfite, saturated brine, dried over sodium sulfate and concentrated to dryness at reduced pressure. The residue was subjected to HPLC purification (ACN: Water-0.1% Formic acid) to provide the pure product (12 mg, 6.4%). $^1$H NMR (400 MHz, CHLOROFORM-d) δ ppm 7.97 (br. s., 2H), 7.87 (d, J=5.37 Hz, 2H), 7.56-7.64 (m, 2H), 7.49 (s, 1H), 7.15-7.24 (m, 2H), 6.15-6.37 (m, 1H), 5.77-5.92 (m, 1H), 3.30 (s, 3H), 3.13 (br. s., 3H), 3.00 (d, J=2.34 Hz, 3H), 1.91-2.10 (m, 1H), 1.18-1.34 (m, 1H), 0.95-1.10 (m, 1H), 0.83-0.93 (m, 1H), 0.69-0.83 (m, 1H), 0.44-0.61 (m, 1H). LCMS (m/z, $ES^+$)=601 (M+H+).

Example 17

1-(2-Chloro-4-(N-(5-cyclopropyl-2-(4-fluorophenyl)-3-(methylcarbamoyl)benzofuran-6-yl)methylsulfonamido)phenyl)-4-methyl-2,6,7-trioxa-1-borabicyclo[2.2.2]octan-1-uide potassium salt

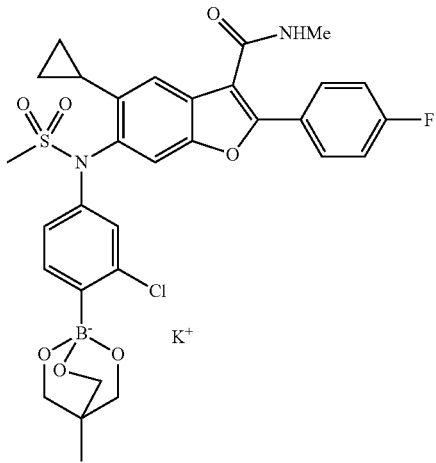 [SMILES: CNC(=O)c1c(-c2ccc(F)cc2)oc2cc(N(c3ccc([B-]45OCC(C)(CO4)CO5)c(Cl)c3)S(C)(=O)=O)c(C3CC3)cc12 ; [K+]]

To a stirred solution of (2-chloro-4-(N-(5-cyclopropyl-2-(4-fluorophenyl)-3-(methylcarbamoyl)benzofuran-6-yl)methylsulfonamido)phenyl)boronic acid (0.0750 g, 0.135 mmol) and 1,1,1-tris(hydroxymethyl)ethane (0.0180 g, 0.148 mmol) in anhydrous THF (6 mL) was added activated 3 angstrom molecular sieves (0.400 g). The resulting mixture was heated to reflux for 4 hours and cooled to RT. The mixture was filtered to remove solids and the filtrate concentrated to dryness at reduced pressure. The residue was dissolved in 5 mL of anhydrous THF and the solution cooled to 0° C. The solution was treated with 1M potassium t-butoxide/THF (135 μL, 0.135 mmol) by dropwise addition. After warming to RT the solution was concentrated to dryness at reduced pressure to afford the title compound as a light yellow solid in quantitative yield. ¹H NMR (400 MHz, DMSO-d₆) δ ppm 8.48 (d, J=4.0 Hz, 1H) 8.09 (s, 1H) 7.98 (dd, J=8.9, 5.5 Hz, 2H) 7.51 (d, J=7.9 Hz, 1H) 7.39 (t, J=8.9 Hz, 2H) 7.07-7.18 (m, 3H) 3.55 (s, 6H) 3.28 (s, 3H) 2.82 (d, J=3.4 Hz, 3H) 2.10-2.23 (m, 1H) 0.73-1.04 (m, 4H) 0.45 (s, 3H).

Example 18

((4-(N-(5-Cyclopropyl-2-(4-fluorophenyl)-3-(methylcarbamoyl)benzofuran-6-yl)methylsulfonamido)phenoxy)methyl)boronic acid

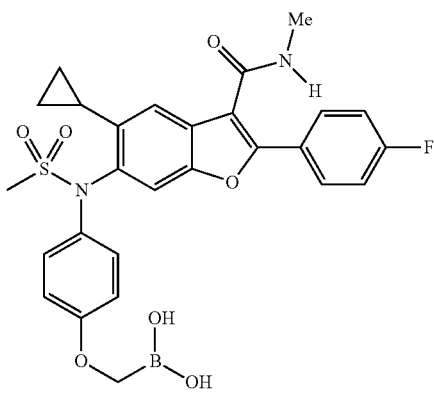 [SMILES: CNC(=O)c1c(-c2ccc(F)cc2)oc2cc(N(c3ccc(OCB(O)O)cc3)S(C)(=O)=O)c(C3CC3)cc12]

Step 1: 6-(N-(4-(Benzyloxy)phenyl)methylsulfonamido)-5-cyclopropyl-2-(4-fluorophenyl)-N-methylbenzofuran-3-carboxamide A stirred mixture of 5-cyclopropyl-2-(4-fluorophenyl)-N-methyl-6-(methylsulfonamido)benzofuran-3-carboxamide (0.500 g, 1.24 mmol), (4-(benzyloxy)phenyl)boronic acid (0.567 g, 2.49 mmol), copper(II) acetate (0.451 g, 2.49 mmol), and triethylamine (1.00 mL, 7.12 mmol) in DCM (25 mL) was treated with 1.00 g of powdered 3 angstrom molecular sieves. The resulting mixture was stirred at RT under air using a drying tube to exclude moisture. After 18 hours the mixture was treated with an additional 250 mg portion of (4-(benzyloxy)phenyl)boronic acid and stirring at RT continued. After another 8 hours the mixture was filtered through Celite and the filtrate concentrated to dryness at reduced pressure. The black residue was suspended in EtOAc and the undissolved solids removed by filtration through Celite. The filtrate was concentrated to dryness at reduced pressure and the residue subjected to flash chromatography (silica gel, gradient elution from DCM to 1:1 DCM/EtOAc to give the title compound (0.403 g, 56%) as a white solid. ¹H NMR (400 MHz, DMSO-d₆) δ ppm 8.39-8.47 (m, 1H) 8.12-8.18 (m, 1H) 7.92-7.99 (m, 2H) 7.55 (d, J=8.9 Hz, 2H) 7.28-7.46 (m, 7H) 7.13 (s, 1H) 7.03 (d, J=9.0 Hz, 2H) 5.09 (s, 2H) 3.29 (s, 3H) 2.82 (d, J=4.5 Hz, 3H) 2.25-2.35 (m, 1H) 0.75-1.14 (m, 3H) 0.32-0.58 (m, 1H). LCMS (m/z, ES⁺)=585 (M+H+).

Step 2: 5-Cyclopropyl-2-(4-fluorophenyl)-6-(N-(4-hydroxyphenyl)methylsulfonamido)-N-methylbenzofuran-3-carboxamide A solution of 6-(N-(4-(benzyloxy)phenyl)methylsulfonamido)-5-cyclopropyl-2-(4-fluorophenyl)-N-methylbenzofuran-3-carboxamide (0.174 g, 0.298 mmol) in 3:1 THF/EtOH (20 mL) was subjected to hydrogenation at 40 psi in the presence of 5% palladium on charcoal (20 mg). After 3 hours the reaction vessel was purged with nitrogen, catalyst removed by filtration through Celite and the filtrate concentrated to dryness at reduced pressure. The residue was triturated with DCM/hexane. The resulting solid was collected by filtration and dried in vacuo to afford the title compound (144 mg, 98%) as an off-white solid. ¹H NMR (400 MHz, DMSO-d₆) δ ppm 9.67 (br. s., 1H) 8.44 (q, J=4.4 Hz, 1H) 8.13 (s, 1H) 7.97 (dd, J=8.9, 5.4 Hz, 2H) 7.46 (d, J=8.9 Hz, 2H) 7.40 (t, J=8.9 Hz, 2H) 7.12 (s, 1H) 6.77 (d, J=8.9 Hz, 2H) 3.27 (s, 3H) 2.83 (d, J=4.6 Hz, 3H) 2.28-2.39 (m, 1H) 0.76-1.11 (m, 3H) 0.47 (br. s., 1H). LCMS (m/z, ES⁺)=495 (M+H+).

Step 3: ((4-(N-(5-Cyclopropyl-2-(4-fluorophenyl)-3-(methylcarbamoyl)benzofuran-6-yl)methylsulfonamido)phenoxy)methyl)boronic acid A mixture of 5-cyclopropyl-2-(4-fluorophenyl)-6-(N-(4-hydroxyphenyl)methylsulfonamido)-N-methylbenzofuran-3-carboxamide (85.0 mg, 0.172 mmol), potassium carbonate (0.119 g, 0.859 mmol), and 2-(bromomethyl)-4,4,5,5-tetramethyl-1,3,2-dioxaborolane (0.152 g, 0.688 mmol) in MeCN (3 mL) in a sealed tube was heated to 65° C. with stirring. After 2 hours the mixture was cooled to RT, filtered to remove solids, and the filtrate concentrated to dryness at reduced pressure. The residue was subjected to RP-HPLC purification (C18, MeCN/water/0.1% formic acid) followed by lyophilization from MeCN/water to give the title compound (77 mg, 81%) as a white powder. ¹H NMR (400 MHz, DMSO-d₆) δ ppm 8.40-8.47 (m, 1H) 8.15 (s, 1H) 8.03 (s, 2H) 7.97 (dd, J=8.8, 5.4 Hz, 2H) 7.53 (d, J=9.0 Hz, 2H) 7.40 (t, J=8.9 Hz, 2H) 7.12 (s, 1H) 6.90 (d, J=9.1 Hz, 2H) 3.58 (s, 2H) 3.33 (s, 3H) 2.82 (d, J=4.5 Hz, 3H) 2.24-2.38 (m, 1H) 0.76-1.10 (m, 3H) 0.47 (br. s., 1H). LCMS (m/z, ES⁺)=553 (M+H+).

Example 19

((2-Chloro-4-(N-(5-cyclopropyl-2-(4-fluorophenyl)-3-(methylcarbamoyl)benzofuran-6-yl)methylsulfonamido)phenoxy)methyl)boronic acid

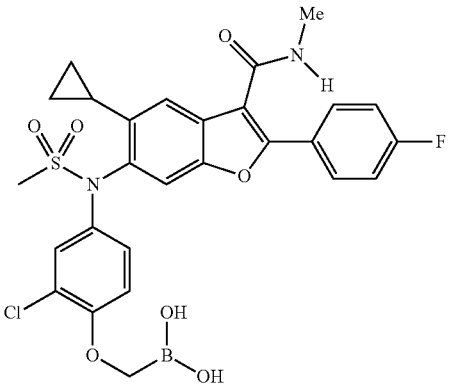 [SMILES: CNC(=O)c1c(-c2ccc(F)cc2)oc2cc(N(c3ccc(OCB(O)O)c(Cl)c3)S(C)(=O)=O)c(C3CC3)cc12]

Step 1: 6-(N-(4-(Benzyloxy)-3-chlorophenyl)methylsulfonamido)-5-cyclopropyl-2-(4-fluorophenyl)-N-methylbenzofuran-3-carboxamide A mixture of 5-cyclopropyl-2-(4-fluorophenyl)-N-methyl-6-(methylsulfonamido)benzofuran-3-carboxamide (1.00 g, 2.49 mmol), (4-(benzyloxy)-3-chlorophenyl)boronic acid (1.31 g, 4.97 mmol), copper(II) acetate (0.903 g, 4.97 mmol), and triethylamine (2.00 mL, 14.4 mmol) in anhydrous DCM (25 mL) was treated with powdered 3 angstrom molecular sieves (2.00 g). The resulting mixture was stirred at RT under air using a drying tube to exclude moisture. After 18 hours the mixture was treated with an additional 1.00 g portion of (4-(benzyloxy)-3-chlorophenyl)boronic acid. After another 18 hours the mixture was diluted with 15 mL of DCM and treated with 1.30 g of (4-(benzyloxy)-3-chlorophenyl)boronic acid, 0.900 g of copper(II) acetate, 2.00 g of 3 angstrom molecular sieves and 2 mL of triethylamine. After 16 more hours the mixture was filtered through Celite to remove solids and the filtrate concentrated to dryness at reduced pressure. The residue was suspended in EtOAc and the undissolved solids removed by filtration through Celite. The filtrate was washed with water (2×), brine (1×), dried over sodium sulfate and concentrated to dryness at reduced pressure. The crude material was purified by flash chromatography (silica gel, gradient from DCM to 7:3 DCM/EtOAc) followed by recrystallization from hexane/EtOAc to afford the title compound (0.83 g, 54%) as an off white solid. $^1$H NMR (400 MHz, DMSO-$d_6$) δ ppm 8.40-8.47 (m, 1H) 8.20 (s, 1H) 7.93-8.00 (m, 2H) 7.69 (d, J=2.6 Hz, 1H) 7.52 (dd, J=8.9, 2.7 Hz, 1H) 7.30-7.48 (m, 7H) 7.25 (d, J=9.1 Hz, 1H) 7.14 (s, 1H) 5.21 (s, 2H) 3.33 (s, 3H) 2.82 (d, J=4.6 Hz, 3H) 2.17-2.33 (m, 1H) 0.75-1.09 (m, 3H) 0.42 (br. s., 1H). LCMS (m/z, ES$^+$)=619, 621 (M+H+).

Step 2: 6-(N-(3-Chloro-4-hydroxyphenyl)methylsulfonamido)-5-cyclopropyl-2-(4-fluorophenyl)-N-methylbenzofuran-3-carboxamide A solution of 6-(N-(4-(benzyloxy)-3-chlorophenyl)methylsulfonamido)-5-cyclopropyl-2-(4-fluorophenyl)-N-methylbenzofuran-3-carboxamide (0.300 g, 0.485.mmol) in anhydrous DCM (12 mL) was cooled in an ice water bath and treated with 1M BCl$_3$/DCM (2.00 mL, 2.00 mmol). After stirring in the ice bath for 10 minutes the solution was allowed to warm to RT. This solution was then combined with the solution from an analogous 50 mg scale reaction and poured into 50 mL of stirred ice water. The mixture was diluted with 50 mL of EtOAc, stirred vigorously for several minutes and the phases separated. The EtOAc solution was washed with water (2×), brine (1×), dried over sodium sulfate and concentrated to dryness at reduced pressure. The crude material was subjected to flash chromatography (silica gel, gradient from DCM to 1:1 DCM/EtOAc) followed by recrystallization from hexane/EtOAc to afford the title compound (0.110 g, 37%) as a white powder. Impure fractions from the above chromatography were combined, concentrated, and subjected to RP-HPLC purification (C18, MeCN/water/0.1% formic acid) to afford an additional portion of the title compound (0.107 g, 36%) for a total yield of 73%. $^1$H NMR (400 MHz, DMSO-$d_6$) δ ppm 10.45 (s, 1H) 8.40-8.48 (m, 1H) 8.18 (s, 1H) 7.90-8.01 (m, 2H) 7.61 (d, J=2.6 Hz, 1H) 7.34-7.45 (m, 3H) 7.14 (s, 1H) 6.96 (d, J=8.8 Hz, 1H) 3.30 (s, 3H) 2.82 (d, J=4.6 Hz, 3H) 2.20-2.34 (m, 1H) 0.77-1.09 (m, 3H) 0.43 (br. s., 1H). LCMS (m/z, ES$^+$)=529 (M+H+).

Step 3: ((2-Chloro-4-(N-(5-cyclopropyl-2-(4-fluorophenyl)-3-(methylcarbamoyl)benzofuran-6-yl)methylsulfonamido)phenoxy)methyl)boronic acid A mixture of 6-(N-(3-chloro-4-hydroxyphenyl)methylsulfonamido)-5-cyclopropyl-2-(4-fluorophenyl)-N-methylbenzofuran-3-carboxamide (65.0 mg, 0.123 mmol), potassium carbonate (85.0 mg, 0.614 mmol), and 2-(bromomethyl)-4,4,5,5-tetramethyl-1,3,2-dioxaborolane (0.109 g, 0.492 mmol) in 4 mL of anhydrous MeCN in a sealed tube was heated to 65° C. with stirring. After 2 hours the mixture was cooled to RT, filtered to remove solids, and the filtrate concentrated to dryness at reduced pressure. The residue was subjected to RP-HPLC purification (C18, MeCN/water/0.1% formic acid) followed by lyophilization from MeCN/water to afford the title compound (43 mg, 60%) as a white powder. $^1$H NMR (400 MHz, DMSO-$d_6$) δ ppm 8.40-8.47 (m, 1H) 8.20 (s, 1H) 8.05 (s, 2H) 7.97 (dd, J=8.7, 5.5 Hz, 2H) 7.65 (d, J=2.5 Hz, 1H) 7.53 (dd, J=8.9, 2.6 Hz, 1H) 7.40 (t, J=8.8 Hz, 2H) 7.14 (s, 1H) 7.00 (d, J=9.1 Hz, 1H) 3.73 (s, 2H) 3.32 (s, 3H) 2.82 (d, J=4.5 Hz, 3H) 2.20-2.35 (m, 1H) 0.90 (br. s., 3H) 0.45 (br. s., 1H). LCMS (m/z, ES$^+$)=587 (M+H+).

Example 20

5-Cyclopropyl-2-(4-fluorophenyl)-6-(N-(1-hydroxy-1,3-dihydrobenzo[c][1,2]oxaborol-5-yl)methylsulfonamido)-N-methylbenzofuran-3-carboxamide

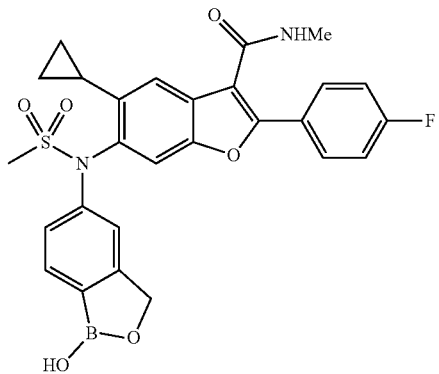 [SMILES: CNC(=O)c1c(-c2ccc(F)cc2)oc2cc(N(c3ccc4c(c3)COB4O)S(C)(=O)=O)c(C3CC3)cc12]

Step 1: Methyl 5-(N-(5-cyclopropyl-2-(4-fluorophenyl)-3-(methylcarbamoyl)benzofuran-6-yl)methylsulfonamido)-2-nitrobenzoate A mixture of methyl 5-fluoro-2-nitrobenzoate (2.138 g, 10.73 mmol), 5-cyclopropyl-2-(4-fluorophenyl)-N-methyl-6-(methylsulfonamido)benzofuran-3-carboxamide (4.0 g, 9.94 mmol) and K$_2$CO$_3$ (4.12 g, 29.8 mmol) in hexamethylphosphoramide (25 mL) in a seal tube was stirred at 60° C. for 3 days. Cooled down to room temperature, the mixture was diluted with EtOAc and then filtered through a pad of Celite. The filtrate was washed with water and brine and dried over Na$_2$SO$_4$. Concentrated under reduced pressure, the residue was purified by flashing chromatography on silica gel eluted with 0-50% EtOAc in hexane to give the product (3.2 g, 55%) as a yellow solid. $^1$H NMR (400 MHz, CHLOROFORM-d) δ ppm 8.00 (d, J=9.17 Hz, 1H) 7.89 (dd, J=8.78, 5.27 Hz, 2H) 7.55 (d, J=9.37 Hz, 2H) 7.50 (dd, J=9.07, 2.63 Hz, 1H) 7.44 (d, J=2.73 Hz, 1H) 7.23 (t, J=8.68 Hz, 2H) 5.81 (d, J=4.49 Hz, 1H) 3.91 (s, 3H) 3.35 (s, 3H) 3.02 (d, J=4.88 Hz, 3H) 1.86-1.96 (m, 1H) 0.97-1.05 (m, 1H) 0.89 (br. s., 2H) 0.59 (br. s., 1H). LCMS (m/z, ES$^+$)=582 (M+H+).

Step 2: Methyl 2-amino-5-(N-(5-cyclopropyl-2-(4-fluorophenyl)-3-(methylcarbamoyl)benzofuran-6-yl)methylsulfonamido)benzoate Methyl 5-(N-(5-cyclopropyl-2-(4-fluorophenyl)-3-(methylcarbamoyl)benzofuran-6-yl)methylsulfonamido)-2-nitrobenzoate (3.2 g, 5.50 mmol) was dissolved in methanol (50 mL), hydrogenation was carried out under $H_2$ (($H_2$ balloon) in the present of 10% Pd/C (0.586 g, 0.550 mmol) at room temperature. The mixture was stirred for 6 hours, It was then filtered by pass through a pad of Celite. Concentrated under reduced pressure, it was rinsed twice with hexane to give the desired product (3.0 g, 98%) as a yellow solid which was used for the next step without further purification. LCMS (m/z, $ES^+$)=552 (M+H+).

Step 3: Methyl 2-bromo-5-(N-(5-cyclopropyl-2-(4-fluorophenyl)-3-(methylcarbamoyl)benzofuran-6-yl) methylsulfonamido)benzoate A suspension of methyl 2-amino-5-(N-(5-cyclopropyl-2-(4-fluorophenyl)-3-(methylcarbamoyl)benzofuran-6-yl)methylsulfonamido)benzoate (1.6 g, 2.70 mmol) in acetonitrile (30 mL) and hydrogen bromide (25 mL, 2.70 mmol) was treated with aqueous sodium nitrite (0.205 g, 2.97 mmol) at 0° C. and the mixture was stirred for 30 min, copper(I) bromide (0.464 g, 3.24 mmol) was added in portions at the same temperature. It was allowed to warm up to room temperature and then heated to 55° C. overnight. The mixture was cooled down to room temperature and partitioned between EtOAc and water. The organic phase was washed with brine, dried over $Na_2SO_4$. Concentrated under reduced pressure, the residue was purified by flashing chromatography on silica gel eluted with 0-50% EtOAc in hexane to give the product (0.92 g, 55%) as a white foam. $^1$H NMR (400 MHz, DMSO-$d_6$) δ ppm 8.49 (q, J=4.23 Hz, 1H) 8.14 (s, 1H) 7.97 (dd, J=8.78, 5.46 Hz, 2H) 7.80 (d, J=2.93 Hz, 1H) 7.75 (d, J=8.78 Hz, 1H) 7.50 (dd, J=8.88, 2.83 Hz, 1H) 7.41 (t, J=8.88 Hz, 2H) 7.22 (s, 1H) 3.84 (s, 3H) 3.44 (s, 3H) 2.84 (d, J=4.68 Hz, 3H) 2.05-2.15 (m, 1H) 0.92-1.05 (br. s, 1H) 0.87 (br. s., 2H) 0.40 (br. s., 1H). LCMS (m/z, $ES^+$)=617 (M+H+).

Step 4: 6-(N-(4-Bromo-3-(hydroxymethyl)phenyl) methylsulfonamido)-5-cyclopropyl-2-(4-fluorophenyl)-N-methylbenzofuran-3-carboxamide $LiBH_4$ (1.593 mL, 3.19 mmol) solution (2M in THF) was added dropwise to a solution of methyl 2-bromo-5-(N-(5-cyclopropyl-2-(4-fluorophenyl)-3-(methylcarbamoyl)benzofuran-6-yl)methylsulfonamido)benzoate (0.76 g, 1.062 mmol) in tetrahydrofuran (6.0 mL) and methanol (0.600 mL) at 0° C. under $N_2$. The mixture was stirred for 3 hours at the same temperature. It was quenched with 1M NaOH and then partitioned between EtOAc and water. The aqueous layer was extracted with EtOAc (2×). The organic phase was washed with brine, dried over $Na_2SO_4$. It was concentrated to dryness to give the crude product (>99%) as tan foam which was used for the next step without further purification. LCMS (m/z, $ES^+$)=587 (M+H+).

Step 5: 6-(N-(4-Bromo-3-((methoxymethoxy)methyl)phenyl)methylsulfonamido)-5-cyclopropyl-2-(4-fluorophenyl)-N-methylbenzofuran-3-carboxamide Chloro(methoxy)methane (0.201 mL, 2.65 mmol) was added dropwise to a solution of 6-(N-(4-bromo-3-(hydroxymethyl)phenyl)methylsulfonamido)-5-cyclopropyl-2-(4-fluorophenyl)-N-methylbenzofuran-3-carboxamide (0.724 g, 1.06 mmol) and DIEA (0.555 mL, 3.18 mmol) in tetrahydrofuran (10 mL) under $N_2$. The mixture was heated to 50° C. overnight. Cooled down to room temperature and aqueous $NaHCO_3$ was added, the aqueous layer was extracted with EtOAc (2×). The organic phase was washed with brine, dried over $Na_2SO_4$. The crude residue was purified by chromatography on silica gel eluted with 0-50% EtOAC in hexane to give the product (0.65 g, 97%) as a white solid. $^1$H NMR (400 MHz, CHLOROFORM-d) δ ppm 7.90 (dd, J=8.78, 5.27 Hz, 2H) 7.64 (s, 1H) 7.57 (d, J=2.73 Hz, 1H) 7.50 (d, J=8.78 Hz, 1H) 7.47 (s, 1H) 7.18-7.26 (m, 3H) 5.79 (d, J=4.49 Hz, 1H) 4.74 (s, 2H) 4.61 (s, 2H) 3.39 (s, 3H) 3.25 (s, 3H) 3.01 (d, J=4.88 Hz, 3H) 2.08-2.18 (m, 1H) 0.75-1.14 (m, 3H) 0.58 (br. s., 1H). LCMS (m/z, $ES^+$)=633 (M+H+).

Step 6: 5-Cyclopropyl-2-(4-fluorophenyl)-6-(N-(3-((methoxymethoxy)methyl)-4-(4,4,5,5-tetramethyl-1,3,2-dioxaborolan-2-yl)phenyl)methylsulfonamido)-N-methylbenzofuran-3-carboxamide A mixture of 6-(N-(4-bromo-3-((methoxymethoxy)methyl)phenyl)methylsulfonamido)-5-cyclopropyl-2-(4-fluorophenyl)-N-methylbenzofuran-3-carboxamide (200 mg, 0.317 mmol), potassium acetate (124 mg, 1.267 mmol), bis (pinacolato)diboron (161 mg, 0.633 mmol) and $PdCl_2$(dppf)-$CH_2Cl_2$ adduct (25.9 mg, 0.032 mmol) in 1,4-dioxane (3.0 ml) was maintained at 90° C. in a seal tube under $N_2$ overnight. The mixture was cooled down to room temperature, diluted with EtOAc, filtered through a pad of silic gel and Celite and then concentrated to dryness to give the crude product as tan foam which was used for the next step without further purification. LCMS (m/z, $ES^+$)=679 (M+H+).

Step 7: (4-(N-(5-Cyclopropyl-2-(4-fluorophenyl)-3-(methylcarbamoyl)benzofuran-6-yl)methylsulfonamido)-2-((methoxymethoxy)methyl)phenyl)boronic acid The crude 5-cyclopropyl-2-(4-fluorophenyl)-6-(N-(3-((methoxymethoxy)methyl)-4-(4,4,5,5-tetramethyl-1,3,2-dioxaborolan-2-yl)phenyl)methylsulfonamido)-N-methylbenzofuran-3-carboxamide (215 mg, 0.317 mmol) was dissolved in methanol (1.0 mL) and tetrahydrofuran (4.0 mL). HCl (4.0 mL, 4.00 mmol) was added followed by addition of sodium periodate (542 mg, 2.54 mmol). The mixture was stirred at room temperature overnight. It was partitioned between EtOAc and water. The aqueous layer was extracted with EtOAc (2×). The organic phase was washed with 10% aq. $Na_2S_2O_3$, brine, dried over $Na_2SO_4$. Concentrated under reduced pressure, the residue was purified by reversed phase HPLC (10-100 MeCN/$H_2O$ with 0.05% TFA) to give product (54 mg, 29%) as a white solid. $^1$H NMR (400 MHz, DMSO-$d_6$) δ ppm 8.47 (q, J=4.36 Hz, 1H) 8.07 (s, 1H) 7.97 (dd, J=8.88, 5.37 Hz, 2H) 7.31-7.53 (m, 5H) 7.14-7.20 (m, 1H) 4.65 (s, 2H) 4.59 (s, 2H) 3.37 (s, 2H) 3.24 (s, 2H) 2.83 (d, J=4.68 Hz, 3H) 2.11-2.26 (m, 1H) 1.01 (br. s., 1H) 0.84 (br. s., 2H) 0.52 (br. s., 1H). LCMS (m/z, $ES^+$)=597 (M+H+).

Step 8: 5-Cyclopropyl-2-(4-fluorophenyl)-6-(N-(1-hydroxy-1,3-dihydrobenzo[c][1,2]oxaborol-5-yl) methylsulfonamido)-N-methylbenzofuran-3-carboxamide HCl (1.0 mL, 1.000 mmol) was added to a solution of (4-(N-(5-cyclopropyl-2-(4-fluorophenyl)-3-(methylcarbamoyl)benzofuran-6-yl)methylsulfonamido)-2-((methoxymethoxy)methyl)phenyl)boronic acid (53 mg, 0.089 mmol) in tetrahydrofuran (1.0 mL) and methanol (0.2 mL). The mixture was heated to 70° C. under $N_2$ overnight. Cooled down to room temperature, it was then evaporated to dry under reduced pressure to give the desired product (46 mg, 97%) as light-yellow solid.

¹H NMR (400 MHz, DMSO-d₆) δ ppm 9.20 (br. s., 1H) 8.49 (q, J=4.42 Hz, 1H) 8.06 (s, 1H) 7.97 (dd, J=8.98, 5.46 Hz, 2H) 7.71 (d, J=8.19 Hz, 1H) 7.48 (s, 1H) 7.35-7.44 (m, 3H) 7.19 (s, 1H) 4.96 (s, 2H) 3.42 (s, 3H) 2.84 (d, J=4.68 Hz, 3H) 2.09-2.21 (m, 1H) 0.99 (br. s., 1H) 0.81 (d, J=5.27 Hz, 2H) 0.50 (br. s., 1H). LCMS (m/z, ES⁺)=535 (M+H+).

Example 21

(4-(N-(2-(4-Chlorophenyl)-5-cyclopropyl-3-(methylcarbamoyl)benzofuran-6-yl)methylsulfonamido)-2-cyanophenyl)boronic acid

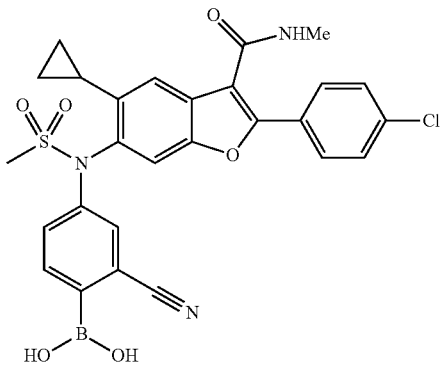 [SMILES: CNC(=O)c1c(-c2ccc(Cl)cc2)oc2cc(N(c3ccc(B(O)O)c(C#N)c3)S(C)(=O)=O)c(C3CC3)cc12]

Step 1: 2-(4-Chlorophenyl)-6-(N-(3-cyano-4-nitrophenyl)methylsulfonamido)-5-cyclopropyl-N-methylbenzofuran-3-carboxamide A mixture of 5-fluoro-2-nitrobenzonitrile (0.656 mL, 5.73 mmol), 2-(4-chlorophenyl)-5-cyclopropyl-N-methyl-6-(methylsulfonamido)benzofuran-3-carboxamide (2.0 g, 4.77 mmol) and K₂CO₃ (1.980 g, 14.32 mmol) in 1,2-dimethoxyethane (20 mL) and water (5.0 mL) in a seal tube was heated to 80° C. overnight. Cooled down to room temperature, it was diluted with EtOAc. The mixture was washed with water and brine, dried over Na₂SO₄. It was concentrated to dryness to give the crude product (>99%) as yellow solid which was used for the next step without further purification. LCMS (m/z, ES⁺)=565 (M+H+).

Step 2: 6-(N-(4-Amino-3-cyanophenyl)methylsulfonamido)-2-(4-chlorophenyl)-5-cyclopropyl-N-methylbenzofuran-3-carboxamide A solution of Na₂S₂O₄ (4.98 g, 28.6 mmol) in water (50 mL) was added dropwise to a solution of 2-(4-chlorophenyl)-6-(N-(3-cyano-4-nitrophenyl)methylsulfonamido)-5-cyclopropyl-N-methylbenzofuran-3-carboxamide (2.70 g, 4.77 mmol) in THF at room temperature under N₂. The mixture was stirred overnight. More water was added and then extracted with EtOAc. The combined extracts were washed with brine, dried over Na₂SO₄. Concentrated under reduced pressure, the crude residue was purified by chromatography on silica gel eluted with 0-15% EtOAc in DCM to give the product (2.3 g, 83%) as a white solid. LCMS (m/z, ES⁺)=535 (M+H+).

Step 3: 6-(N-(4-Bromo-3-cyanophenyl)methylsulfonamido)-2-(4-chlorophenyl)-5-cyclopropyl-N-methylbenzofuran-3-carboxamide tBuNO₂ (0.611 ml, 5.14 mmol) was added dropwise to a solution of CuBr₂ (0.918 g, 4.11 mmol) in acetonitrile (5 mL). The mixture was heated to 50° C. for 10 min and then a suspension of 6-(N-(4-amino-3-cyanophenyl)methylsulfonamido)-2-(4-chlorophenyl)-5-cyclopropyl-N-methylbenzofuran-3-carboxamide (1.1 g, 2.056 mmol) in acetonitrile (25 mL) was added in portions to above mixture. It was stirred for 30 min at 50° C. and then cooled down to room temperature. It was quenched with ice-cooled HCl (1N) and then extracted with EtOAc. The combined extracts were washed with 10% Na₂S₂O₃ and brine, dried over Na₂SO₄. Concentrated under reduced pressure, the residue was purified by flashing chromatography on silica gel eluted with 0-5% EtOAc in DCM to give the product (0.64 g, 52%) as a light-yellow foam. ¹H NMR (400 MHz, CHLOROFORM-d) δ ppm 7.84 (d, J=8.59 Hz, 2H) 7.58-7.64 (m, 3H) 7.47-7.53 (m, 4H) 5.80 (d, J=4.29 Hz, 1H) 3.28 (s, 3H) 3.03 (d, J=4.88 Hz, 3H) 1.91-2.00 (m, 1H) 0.72-1.11 (m, 3H) 0.55 (br. s., 1H). LCMS (m/z, ES⁺)=600 (M+H+).

Step 4: 2-(4-Chlorophenyl)-6-(N-(3-cyano-4-(4,4,5,5-tetramethyl-1,3,2-dioxaborolan-2-yl)phenyl)methylsulfonamido)-5-cyclopropyl-N-methylbenzofuran-3-carboxamide A mixture of 6-(N-(4-bromo-3-cyanophenyl)methylsulfonamido)-2-(4-chlorophenyl)-5-cyclopropyl-N-methylbenzofuran-3-carboxamide (150 mg, 0.250 mmol), potassium acetate (98 mg, 1.002 mmol), bis(pinacolato)diboron (127 mg, 0.501 mmol) and PdCl₂(dppf)-CH₂Cl₂ adduct (20.5 mg, 0.025 mmol) in 1,4-dioxane (3 ml) was maintained at 90° C. in a seal tube under N2 for 3 hours. LCMS (UV 254) showed 47% of desired product, 53% of the corresponding boronic acid (generated on LC probably?). The mixture was cooled down to room temperature, diluted with EtOAc, filtered through a pad of silic gel and Celite and then concentrated to dryness to give the crude product (>99%) as light-yellow foam which was used for the next step without further purification. LCMS (m/z, ES⁺)=646 (M+H+).

Step 5: (4-(N-(2-(4-Chlorophenyl)-5-cyclopropyl-3-(methylcarbamoyl)benzofuran-6-yl)methylsulfonamido)-2-cyanophenyl)boronic acid The crude 2-(4-chlorophenyl)-6-(N-(3-cyano-4-(4,4,5,5-tetramethyl-1,3,2-dioxaborolan-2-yl)phenyl)methylsulfonamido)-5-cyclopropyl-N-methylbenzofuran-3-carboxamide (162 mg, 0.251 mmol) was dissolved in tetrahydrofuran (6.0 mL). HCl (3.01 mL, 1.505 mmol) was added followed by addition of sodium periodate (429 mg, 2.006 mmol). The mixture was stirred at room temperature overnight. It was partitioned between EtOAc and water. The aqueous layer was extracted with EtOAc (2×). The organic phase was washed with 10% aq. Na₂S₂O₃ and brine, dried over Na₂SO₄. Concentrated under reduced pressure, the residue was purified by reversed phase HPLC (10-100 MeCN/H₂O with 0.05% TFA) to give product (88 mg, 62%) as a white solid. ¹H NMR (400 MHz, DMSO-d₆) δ ppm 8.54-8.74 (br.s., 1H) 8.51 (q, J=4.49 Hz, 2H) 8.13 (s, 1H) 7.93 (d, J=8.78 Hz, 2H) 7.74-7.79 (m, 2H) 7.58-7.67 (m, 3H) 7.22 (s, 1H) 3.47 (s, 3H) 2.84 (d, J=4.68 Hz, 3H) 2.03-2.14 (m, 1H) 0.99 (br. s., 1H) 0.85 (br. s., 2H) 0.45 (br. s., 1H). LCMS (m/z, ES$^+$)=564 (M+H+).

Example 22

5-Cyclopropyl-2-(4-fluorophenyl)-N-methyl-6-(N-(3-methyl-4-(4,4,5,5-tetramethyl-1,3,2-dioxaborolan-2-yl)phenyl)methylsulfonamido)benzofuran-3-carboxamide

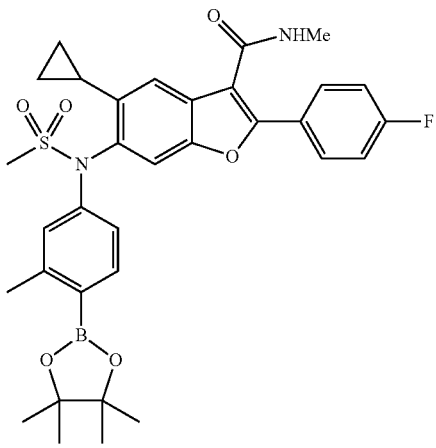 [SMILES: CNC(=O)c1c(-c2ccc(F)cc2)oc2cc(N(c3ccc(B4OC(C)(C)C(C)(C)O4)c(C)c3)S(C)(=O)=O)c(C3CC3)cc12]

Step 1: 5-Cyclopropyl-2-(4-fluorophenyl)-N-methyl-6-(N-(3-methyl-4-nitrophenyl)methylsulfonamido)benzofuran-3-carboxamide To the mixture of 6-(N-(3-chloro-4-nitrophenyl)methylsulfonamido)-5-cyclopropyl-2-(4-fluorophenyl)-N-methylbenzofuran-3-carboxamide (2.5 g, 4.48 mmol) and DABAL-Me$_3$ (1.366 g, 5.38 mmol) in dry Tetrahydrofuran (10 mL) under nitrogen atmosphere was added Pd$_2$(dba)$_3$ (0.041 g, 0.045 mmol) and Xantphos (0.052 g, 0.090 mmol) and the reaction was refluxed at 100° C. for 0.5 h. Reaction mixture was filtered through Celite and washed with methanol (50 mL). After evaporation of the solvent, the crude was redissolved in DCM and washed with water. DCM was dried over anhydrous Na$_2$SO$_4$ and evaporated to give the title compound as a yellow solid in 82% yield. $^1$H NMR (400 MHz, DMSO-d$_6$) δ ppm: 8.02 (d, J=9.2 Hz, 1H), 7.86-7.93 (m, 2H), 7.55 (d, J=1.8 Hz, 2H), 7.17-7.27 (m, 4H), 5.80 (d, J=4.5 Hz, 1H), 3.22-3.44 (m, 3H), 3.02 (d, J=4.9 Hz, 3H), 2.47-2.66 (m, 3H), 1.88-2.11 (m, 1H), 1.03 (br. s., 1H), 0.89 (d, J=7.2 Hz, 2H), 0.62 (br. s., 1H). LCMS (m/z, ES$^+$)=538 (M+H+).

Step 2: 6-(N-(4-Amino-3-methylphenyl)methylsulfonamido)-5-cyclopropyl-2-(4-fluorophenyl)-N-methylbenzofuran-3-carboxamide To 5-cyclopropyl-2-(4-fluorophenyl)-N-methyl-6-(N-(3-methyl-4-nitrophenyl)methylsulfonamido)benzofuran-3-carboxamide (2.0 g, 3.72 mmol) in Ethanol (10 mL) and THF (2 mL), Pd/C (0.396 g) was added and subjected to hydrogenation at RT for 12 h. The reaction mixture was filtered through Celite. The solvent was evaporated under reduced pressure to afford the title compound in 86% yield. $^1$H NMR (400 MHz, DMSO-d$_6$) δ ppm: 7.85-7.95 (m, 1H), 7.67-7.73 (m, 1H), 7.37-7.42 (m, 1H), 7.11-7.26 (m, 1H), 6.59-6.68 (m, 1H), 5.86 (br. s., 1H), 3.18 (s, 1H), 2.99 (s, 2H), 2.10-2.17 (m, 1H), 1.37-1.51 (m, 1H), 1.08-1.19 (m, 1H), 0.91-1.06 (m, 1H), 0.45-0.92 (m, 1H). LCMS (m/z, ES$^+$)=508 (M+H+).

Step 3: 5-Cyclopropyl-2-(4-fluorophenyl)-6-(N-(4-iodo-3-methylphenyl)methylsulfonamido)-N-methylbenzofuran-3-carboxamide 6-(N-(4-Amino-3-methylphenyl)methylsulfonamido)-5-cyclopropyl-2-(4-fluorophenyl)-N-methylbenzofuran-3-carboxamide (1.0 g, 1.97 mmol) was added to p-TsOH (1.12 g, 5.91 mmol) in t-butanol (2 mL) at 5° C. and stirred for 10 min. Then a mixture of sodium nitrite (0.272 g, 3.94 mmol) and KI (0.818 g, 4.93 mmol) in water (1 mL) was added to the reaction mixture. Stirred for 15 min at same temperature, brought to RT and heated at 60° C. for 15 min. Water, sodium bicarbonate solution and sodium thiosulfate solutions (20 mL) were added successively. The resulting precipitate was filtered and dried to give the title compound as a yellow solid in 83% yield. $^1$H NMR (400 MHz, DMSO-d$_6$) δ ppm: 7.84-7.97 (m, 2H), 7.74 (d, J=8.8 Hz, 1H), 7.58-7.67 (m, 1H), 7.47 (s, 1H), 7.26 (br. s., 1H), 7.22 (t, J=8.6 Hz, 2H), 6.92-7.05 (m, 1H), 5.79 (br. s., 1H), 3.25 (s, 3H), 3.02 (d, J=4.9 Hz, 3H), 2.39 (s, 3H), 0.96 (d, J=6.8 Hz, 2H), 0.85 (br. s., 2H), 0.61 (br. s., 1H). LCMS (m/z, ES$^+$)=618 (M+H+).

Step 4: 5-Cyclopropyl-2-(4-fluorophenyl)-N-methyl-6-(N-(3-methyl-4-(4,4,5,5-tetramethyl-1,3,2-dioxaborolan-2-yl)phenyl)methylsulfonamido)benzofuran-3-carboxamide To bis(pinacolato)diboron (103 mg, 0.404 mmol), [bis(diphenylphosphino)ferrocene]dichloropalladium(III) complex (33.0 mg, 0.040 mmol) and potassium acetate (39.7 mg, 0.404 mmol) under a nitrogen atmosphere was added 5-cyclopropyl-2-(4-fluorophenyl)-6-(N-(4-iodo-3-methylphenyl)methylsulfonamido)-N-methylbenzofuran-3-carboxamide (50 mg, 0.081 mmol) and 1,4-dioxane (2 mL) and stirred for 12 h at 80° C. The product and de-iodo product were formed in 80:20 ratio. The mixture was diluted with water and extracted with ethyl acetate (20 mL). Ethyl acetate solution was dried over anhydrous Na$_2$SO$_4$ and evaporated under reduced pressure. The crude was purified by RP-HPLC (ACN/Water/0.1% formic acid) to provide the title compound in 5% yield. $^1$H NMR (400 MHz, DMSO-d$_6$) δ ppm: 8.44-8.56 (m, 1H), 7.90-8.05 (m, 3H), 7.60 (d, J=8.0 Hz, 1H), 7.41 (t, J=8.9 Hz, 2H), 7.12-7.25 (m, 3H), 6.77 (s, OH), 2.84 (d, J=4.5 Hz, 3H), 2.42 (s, 3H), 1.28 (s, 12H), 0.98 (br. s., 1H), 0.79 (br. s., 2H), 0.51 (br. s., 1H). LCMS (m/z, ES⁺)=619 (M+H+).

Example 23

(2-Chloro-4-(N-(5-cyclopropyl-2-(4-fluorophenyl)-3-(methylcarbamoyl)benzofuran-6-yl)methylsulfonamido)phenethyl)boronic acid

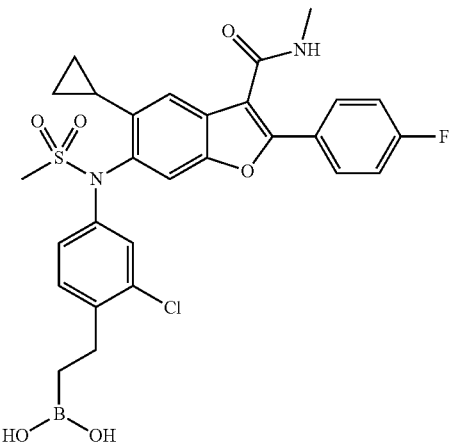 [SMILES: CNC(=O)c1c(-c2ccc(F)cc2)oc2cc(N(c3ccc(CCB(O)O)c(Cl)c3)S(C)(=O)=O)c(C3CC3)cc12]

Step 1: 6-(N-(3-Chloro-4-(2-(4,4,5,5-tetramethyl-1,3,2-dioxaborolan-2-yl)ethyl)phenyl)methylsulfonamido)-5-cyclopropyl-2-(4-fluorophenyl)-N-methylbenzofuran-3-carboxamide A suspension of 6-(N-(3-chloro-4-vinylphenyl)methylsulfonamido)-5-cyclopropyl-2-(4-fluorophenyl)-N-methylbenzofuran-3-carboxamide (200 mg, 0.371 mmol) in THF (2 mL) was added to a stirred solution of bis(1,5-cyclooctadiene)diiridium(I) dichloride (6.2 mg, 0.0091 mmol) and diphenylphosphinobutane (7.9 mg, 0.019 mmol) in THF (2 mL) under nitrogen. After 10 min, pinacolborane (1M in THF) (1.1 mL, 1.11 mmol) was added and the mixture was stirred at room temperature for 3 days. The solvent was evaporated and the residue was subjected to silica gel chromatography with dichloromethane:methanol to give 158 mg of a mixture containing 60% of 6-(N-(3-Chloro-4-(2-(4,4,5,5-tetramethyl-1,3,2-dioxaborolan-2-yl)ethyl)phenyl)methylsulfonamido)-5-cyclopropyl-2-(4-fluorophenyl)-N-methylbenzofuran-3-carboxamide. This material was taken to the next step without further purification. LCMS (m/z, ES⁺)=667 (M+H+).

Step 2: (2-Chloro-4-(N-(5-cyclopropyl-2-(4-fluorophenyl)-3-(methylcarbamoyl)benzofuran-6-yl)methylsulfonamido)phenethyl)boronic acid Sodium periodate (722 mg, 3.37 mmol) and 1N aqueous HCl (2.70 mL, 2.70 mmol) were added to a cold (0° C.) solution of 6-(N-(3-chloro-4-(2-(4,4,5,5-tetramethyl-1,3,2-dioxaborolan-2-yl)ethyl)phenyl)methylsulfonamido)-5-cyclopropyl-2-(4-fluorophenyl)-N-methylbenzofuran-3-carboxamide (150 mg, 0.225 mmol) in THF (3 mL). The mixture was stirred at 0° C. for 10 min and then warmed to room temperature and stirred for 1 hour. The reaction mixture was diluted with ethyl acetate. The organic layer was separated, washed with 5% aqueous sodium thiosulfate and brine and dried over sodium sulfate. The solvent was evaporated and the residue was subjected to reverse phase HPLC (C18, acetonitrile:water with 0.1% formic acid) to give 33 mg (25%) of the title compound as a white powder. ¹H NMR (400 MHz, DMSO-d₆) δ ppm 8.41-8.51 (m, 1H) 8.14 (s, 1H) 7.92-8.02 (m, 2H) 7.59 (s, 2H) 7.46-7.51 (m, 1H) 7.35-7.44 (m, 3H) 7.29-7.35 (m, 1H) 7.17 (s, 1H) 3.37 (s, 3H) 2.79-2.87 (m, 3H) 2.62-2.74 (m, 2H) 2.11-2.24 (m, 1H) 0.93-1.09 (m, 1H) 0.75-0.93 (m, 4H) 0.46 (m, 1H). LCMS (m/z, ES⁺)=585 (M+H+).

Example 24

5-Cyclopropyl-6-(N-(7-fluoro-1-hydroxy-1,3-dihydrobenzo[c][1,2]oxaborol-5-yl)methylsulfonamido)-2-(4-fluorophenyl)-N-methylbenzofuran-3-carboxamide

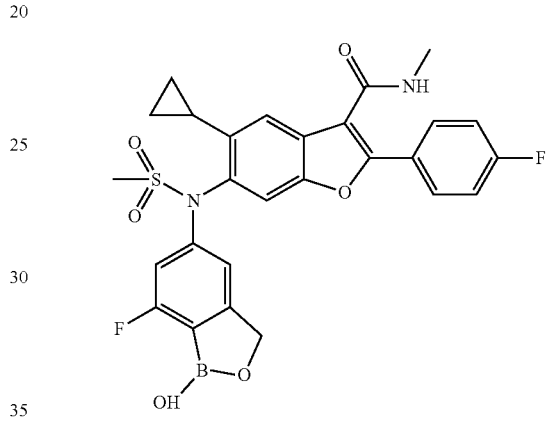

Step 1: Methyl 5-(N-(5-cyclopropyl-2-(4-fluorophenyl)-3-(methylcarbamoyl)benzofuran-6-yl)methylsulfonamido)-3-fluoro-2-nitrobenzoate A mixture of 5-cyclopropyl-2-(4-fluorophenyl)-N-methyl-6-(methylsulfonamido)benzofuran-3-carboxamide (1.850 g, 4.60 mmol), methyl 3,5-difluoro-2-nitrobenzoate (1.996 g, 9.19 mmol) and Na₂CO₃ (1.462 g, 13.79 mmol) in hexamethylphosphoramide (25 mL) was stirred overnight at room temperature. The mixture was diluted with EtOAc and filtered through a pad of Celite®. The filtrate was washed with brine, dried over Na₂SO₄, concentrated and purified by silica gel chromatography (0-35% EtOAc in hexanes) to give methyl 5-(N-(5-cyclopropyl-2-(4-fluorophenyl)-3-(methylcarbamoyl)benzofuran-6-yl)methylsulfonamido)-3-fluoro-2-nitrobenzoate (1.61 g, 58% yield) as yellow solid. ¹H NMR (400 MHz, CHLOROFORM-d) δ ppm 0.62 (br. s., 1H), 0.79-0.95 (m, 2H), 0.96-1.11 (m, 1H), 1.84-1.97 (m, 1H), 3.01 (d, J=5.0 Hz, 3H), 3.31-3.36 (m, 3H), 3.87 (s, 3H), 5.82 (d, J=4.6 Hz, 1H), 7.22 (t, J=8.6 Hz, 2H), 7.37-7.44 (m, 1H), 7.50-7.54 (m, 2H), 7.56 (s, 1H), 7.83-7.92 (m, 2H). LCMS (m/z, ES⁺)= 600.2 (M+H+).

Step 2: Methyl 2-amino-5-(N-(5-cyclopropyl-2-(4-fluorophenyl)-3-(methylcarbamoyl)benzofuran-6-yl)methylsulfonamido)-3-fluorobenzoate A suspension of methyl 5-(N-(5-cyclopropyl-2-(4-fluorophenyl)-3-(methylcarbamoyl)benzofuran-6-yl)methylsulfonamido)-3-fluoro-2-nitrobenzoate (810 mg, 1.351 mmol)

and Pd/C (10% wt, 144 mg, 0.135 mmol) was stirred under hydrogen (1 atm) in THF (10.0 mL) and MeOH (5.0 mL) overnight. The mixture was filtered through 45 um disc and washed with EtOAc. The filtrate was concentrated and purified by silica gel chromatography (0-50% EtOAc in hexanes) to give methyl 2-amino-5-(N-(5-cyclopropyl-2-(4-fluorophenyl)-3-(methylcarbamoyl)benzofuran-6-yl)methylsulfonamido)-3-fluorobenzoate (601 mg, 78% yield) as white solid. $^1$H NMR (400 MHz, CHLOROFORM-d) δ ppm 0.81-1.11 (m, 3H), 2.14-2.26 (m, 1H), 2.91-3.03 (m, 3H), 3.19 (s, 3H), 3.86 (s, 3H), 5.80 (d, J=4.5 Hz, 1H), 5.88 (br. s., 2H), 7.15-7.25 (m, 2H), 7.40 (dd, J=12.1, 2.5 Hz, 1H), 7.44 (s, 1H), 7.70 (s, 1H), 7.80 (dd, J=2.4, 1.5 Hz, 1H), 7.84-7.94 (m, 2H). LCMS (m/z, ES+)=570.3 (M+H+).

Step 3: Methyl 2-bromo-5-(N-(5-cyclopropyl-2-(4-fluorophenyl)-3-(methylcarbamoyl)benzofuran-6-yl)methylsulfonamido)-3-fluorobenzoate A solution of methyl 2-amino-5-(N-(5-cyclopropyl-2-(4-fluorophenyl)-3-(methylcarbamoyl)benzofuran-6-yl)methylsulfonamido)-3-fluorobenzoate (601 mg, 1.055 mmol) in acetonitrile (6 mL) and conc. HBr (6 mL, 48% aq) was cooled in an ice-water bath and then treated with a solution of sodium nitrite (95 mg, 1.372 mmol) in water (1 mL). After 15 min, copper(I) bromide (182 mg, 1.266 mmol) was added to the mixture. The mixture was then heated to 50° C. After 30 min, the solution was cooled to room temperature and diluted with EtOAc. Sodium bisulfate (15 mL, 5% aq) and saturated aqueous $NaHCO_3$ solution (20 mL) were added to the solution. The organic phase was separated and washed by brine (40 mL), dried over $Na_2SO_4$, concentrated and then purified by silica gel chromatography(0-35% EtOAc in hexanes) to give methyl 2-bromo-5-(N-(5-cyclopropyl-2-(4-fluorophenyl)-3-(methylcarbamoyl)benzofuran-6-yl)methylsulfonamido)-3-fluorobenzoate (430 mg, 64% yield) as white solid. $^1$H NMR (400 MHz, CHLOROFORM-d) δ ppm 0.55 (br. s., 1H), 0.75-0.93 (m, 2H), 0.97 (d, J=6.6 Hz, 1H), 1.88-2.04 (m, 1H), 3.01 (d, J=4.9 Hz, 3H), 3.28 (s, 3H), 3.91 (s, 3H), 5.72-5.85 (m, 1H), 7.21 (t, J=8.6 Hz, 2H), 7.33 (dd, J=10.0, 2.8 Hz, 1H), 7.49 (dd, J=2.8, 1.3 Hz, 1H), 7.52 (s, 1H), 7.58 (s, 1H), 7.85-7.92 (m, 2H). LCMS (m/z, ES+)=633, 635 (M+H+).

Step 4: 6-(N-(4-Bromo-3-fluoro-5-(hydroxymethyl)phenyl)methylsulfonamido)-5-cyclopropyl-2-(4-fluorophenyl)-N-methylbenzofuran-3-carboxamide A solution of LiBH$_4$ (1.018 mL, 2M) in THF was added dropwise to a solution of methyl 2-bromo-5-(N-(5-cyclopropyl-2-(4-fluorophenyl)-3-(methylcarbamoyl)benzofuran-6-yl)methylsulfonamido)-3-fluorobenzoate (430 mg, 0.679 mmol) in MeOH (0.5 mL) and THF (5.0 mL) at 0° C. After 0.5 h, citric acid (4.0 mL, 5% wt) was added to the mixture. The organic solvent was then removed under reduced pressure. The residue was diluted with DCM (10 mL) and washed with saturated aqueous $NaHCO_3$, brine, dried over $Na_2SO_4$, filtered and concentrated to give 6-(N-(4-bromo-3-fluoro-5-(hydroxymethyl)phenyl)methylsulfonamido)-5-cyclopropyl-2-(4-fluorophenyl)-N-methylbenzofuran-3-carboxamide (400 mg, 97% yield) as white solid. The crude was used for next step without more purification. $^1$H NMR (400 MHz, CHLOROFORM-d) δ ppm 0.57 (br. s., 1H), 0.71-0.88 (m, 2H), 0.93-1.06 (m, 1H), 1.96-2.02 (m, 1H), 2.63 (t, J=6.1 Hz, 1H), 2.96 (d, J=4.8 Hz, 3H), 3.25 (s, 3H), 4.67 (d, J=5.6 Hz, 2H), 5.96 (d, J=4.8 Hz, 1H), 7.08-7.21 (m, 3H), 7.31 (s, 1H), 7.42 (s, 1H), 7.56 (s, 1H), 7.82 (dd, J=8.7, 5.3 Hz, 2H). LCMS (m/z, ES+)=605, 607 (M+H+).

Step 5: 6-(N-(4-Bromo-3-fluoro-5-((methoxymethoxy)methyl)phenyl)methylsulfonamido)-5-cyclopropyl-2-(4-fluorophenyl)-N-methylbenzofuran-3-carboxamide A mixture of 6-(N-(4-bromo-3-fluoro-5-(hydroxymethyl)phenyl)methylsulfonamido)-5-cyclopropyl-2-(4-fluorophenyl)-N-methylbenzofuran-3-carboxamide (350 mg, 0.578 mmol), DIPEA (0.303 mL, 1.734 mmol) and MOM-Cl (0.110 mL, 1.445 mmol) in THF (3.0 mL) was stirred at 50° C. in a sealed tube. After 23 hours, the solution was concentrated and purified by silica gel chromatography (0-40% EtOAc in hexanes) to give 6-(N-(4-bromo-3-fluoro-5-((methoxymethoxy)methyl)phenyl)methylsulfonamido)-5-cyclopropyl-2-(4-fluorophenyl)-N-methylbenzofuran-3-carboxamide (303 mg, 70% yield). $^1$H NMR (400 MHz, CHLOROFORM-d) δ ppm 0.59 (br. s., 1H), 0.74-0.94 (m, 2H), 0.94-1.10 (m, 1H), 1.99-2.12 (m, 1H), 3.00 (d, J=4.9 Hz, 3H), 3.27 (s, 3H), 3.37 (s, 3H), 4.61 (s, 2H), 4.71 (s, 2H), 5.85 (d, J=4.6 Hz, 1H), 7.13 (dd, J=10.0, 2.7 Hz, 1H), 7.17-7.25 (m, 2H), 7.33 (d, J=1.5 Hz, 1H), 7.48 (s, 1H), 7.58 (s, 1H), 7.83-7.92 (m, 2H). LCMS (m/z, ES+)=649, 651 (M+H+).

Step 6: 5-Cyclopropyl-6-(N-(3-fluoro-5-((methoxymethoxy)methyl)-4-(4,4,5,5-tetramethyl-1,3,2-dioxaborolan-2-yl)phenyl)methylsulfonamido)-2-(4-fluorophenyl)-N-methylbenzofuran-3-carboxamide A mixture of 6-(N-(4-bromo-3-fluoro-5-((methoxymethoxy)methyl)phenyl)methylsulfonamido)-5-cyclopropyl-2-(4-fluorophenyl)-N-methylbenzofuran-3-carboxamide (300 mg, 0.462 mmol), bis(pinacolato)diboron (293 mg, 1.155 mmol), potassium acetate (181 mg, 1.848 mmol) and $PdCl_2$(dppf)-$CH_2Cl_2$ adduct (37.7 mg, 0.046 mmol) in 1,4-dioxane (4.0 mL) was stirred under $N_2$ at 90° C. in a sealed tube overnight. The mixture was cooled to room temperature, diluted with EtOAc, filtered through a pad of silica gel and Celite® and then concentrated to dryness to give the crude product (306 mg) (68% of the title compound, 26% of deborylation by-product) which was used for the next step without further purification. LCMS (m/z, ES+)=697 (M+H+).

Step 7: 5-Cyclopropyl-6-(N-(7-fluoro-1-hydroxy-1,3-dihydrobenzo[c][1,2]oxaborol-5-yl)methylsulfonamido)-2-(4-fluorophenyl)-N-methylbenzofuran-3-carboxamide Aqueous hydrochloric acid (4 mL, 1 N) was added to a solution of 5-cyclopropyl-6-(N-(3-fluoro-5-((methoxymethoxy)methyl)-4-(4,4,5,5-tetramethyl-1,3,2-dioxaborolan-2-yl)phenyl)methylsulfonamido)-2-(4-fluorophenyl)-N-methylbenzofuran-3-carboxamide (306 mg) in THF (4.0 mL) and MeOH (0.8 mL). The mixture was heated to 70° C. under $N_2$ overnight. The mixture was cooled to room temperature and the organic solvent was removed under reduced pressure. The crude was diluted with EtOAc, washed with brine, dried over $Na_2SO_4$, filtered and concentrated to dryness. MeOH (6 mL) was then added to the crude and stirred for 15 min. A white solid was formed which was filtered to give 170 mg crude product (90% purity). 50 mg crude product was purified by silica gel chromatography (0-100% EtOAc in DCM, then 0-10% MeOH in DCM) to give 5-cyclopropyl-6-(N-(7-fluoro-1-hydroxy-1,3-dihydrobenzo[c][1,2]oxaborol-5-yl)methylsulfonamido)-2-(4-fluorophenyl)-N-methylbenzofuran-3-carboxamide (17 mg, 6.24% yield). Another 120 mg crude product was washed with MeOH and dried to give 5-cyclopropyl-6-(N-(7-fluoro-1-hydroxy-1,3-dihydrobenzo[c][1,2]oxaborol-5-yl)methylsulfonamido)-2-(4-fluorophenyl)-N-methylbenzofuran-3-carboxamide (106 mg, 36.6% yield). $^1$H NMR (400 MHz, DMSO-d6) δ ppm 0.50 (br. s., 1H), 0.81 (br. s., 2H), 0.97 (br. s., 1H), 2.06 (br. s., 1H), 2.84 (d, J=4.3 Hz, 3H), 3.48 (s, 3H), 4.95 (s, 2H), 7.02 (d, J=9.9 Hz, 1H), 7.20 (d, J=7.9 Hz, 2H), 7.41 (t, J=8.8 Hz, 2H), 7.97 (dd, J=8.5, 5.6 Hz, 2H), 8.04 (s, 1H), 8.49 (d, J=4.5 Hz, 1H), 9.28 (s, 1H). LCMS (m/z, ES+)= 553 (M+H+).

Example 25

6-(N-(3-Chloro-4-(2-hydroxy-1,2-oxaborolan-4-yl) phenyl)methylsulfonamido)-5-cyclopropyl-2-(4-fluorophenyl)-N-methylbenzofuran-3-carboxamide

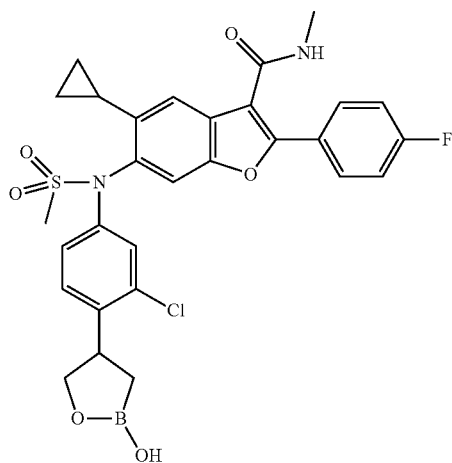 [SMILES: CNC(=O)c1c(-c2ccc(F)cc2)oc2cc(N(c3ccc(C4COB(O)C4)c(Cl)c3)S(C)(=O)=O)c(C3CC3)cc12]

Step 1: 6-(N-(3-Chloro-4-(3-hydroxyprop-1-en-2-yl) phenyl)methylsulfonamido)-5-cyclopropyl-2-(4-fluorophenyl)-N-methylbenzofuran-3-carboxamide A mixture of 6-(N-(4-bromo-3-chlorophenyl)methylsulfonamido)-5-cyclopropyl-2-(4-fluorophenyl)-N-methylbenzofuran-3-carboxamide (327 mg, 0.552 mmol), allyl alcohol (0.475 mL, 6.9 mmol), palladium(II) acetate (29 mg, 0.132 mmol), 1,3-bis(diphenylphosphino)propane (108 mg, 0.26 mmol) and triethylamine (0.7 mL, 4.9 mmol) in DMSO (2 mL) and 1-butyl-3-methylimidazolium tetrafluoroborate (2 mL) was heated at 135° C. in a sealed tube for 59 hours. The reaction mixture was diluted with ethyl acetate and filtered through Celite. The filtrate was washed with water and brine, dried over sodium sulfate and concentrated. Chromatography on silica gel (hexane:ethyl acetate) gave 75 mg (24%) of 6-(N-(3-chloro-4-(3-hydroxyprop-1-en-2-yl)phenyl)methylsulfonamido)-5-cyclopropyl-2-(4-fluorophenyl)-N-methyl-benzofuran-3-carboxamide. $^1$H NMR (400 MHz, chloroform-d) δ ppm 7.84-7.97 (m, 2H) 7.60 (s, 1H) 7.48 (s, 1H) 7.37-7.41 (m, 1H) 7.29-7.32 (m, 1H) 7.28 (s, 1H) 7.16-7.24 (m, 3H) 5.77-5.97 (m, 1H) 5.51-5.63 (m, 1H) 5.17 (s, 1H) 4.34-4.46 (m, 2H) 3.28 (s, 3H) 3.00 (d, J=4.88 Hz, 3H) 2.1 (m, 1H) 0.99-1.10 (m, 1H) 0.77-0.93 (m, 2H) 0.48-0.73 (m, 1H).). LCMS (m/z, ES+)=569 (M+H+).

Step 2: 6-(N-(3-Chloro-4-(3-(methoxymethoxy) prop-1-en-2-yl)phenyl)methylsulfonamido)-5-cyclopropyl-2-(4-fluorophenyl)-N-methylbenzofuran-3-carboxamide Methyl chloromethyl ether (0.024 mL, 0.321 mmol) was added to a mixture of 6-(N-(3-chloro-4-(3-hydroxyprop-1-en-2-yl)phenyl)methylsulfonamido)-5-cyclopropyl-2-(4-fluorophenyl)-N-methylbenzofuran-3-carboxamide (83 mg, 0.146 mmol) and DIEA (0.076 mL, 0.438 mmol) in dichloromethane (2 mL). The mixture was stirred at room temperature for 1.5 hours. The reaction mixture was diluted with dichloromethane and washed with water and brine, dried over sodium sulfate and concentrated to give 6-(N-(3-chloro-4-(3-(methoxymethoxy)prop-1-en-2-yl)phenyl)methylsulfonamido)-5-cyclopropyl-2-(4-fluorophenyl)-N-methylbenzofuran-3-carboxamide as a white foam (76 mg, 85%). $^1$H NMR (400 MHz, chloroform-d) δ ppm 7.89 (dd, J=8.78, 5.27 Hz, 2H) 7.60 (s, 1H) 7.48 (s, 1H) 7.38 (d, J=2.15 Hz, 1H) 7.26-7.31 (m, 1H) 7.16-7.24 (m, 2H) 5.77-5.94 (m, 1H) 5.56 (s, 1H) 5.31 (s, 1H) 5.22 (s, 1H) 4.65 (s, 2H) 4.34 (s, 2H) 3.33 (s, 3H) 3.27 (s, 3H) 3.00 (d, J=4.88 Hz, 3H) 1.87-2.29 (m, 1H) 0.14-1.47 (m, 4H). LCMS (m/z, ES+)=613 (M+H+).

Step 3: 6-(N-(3-Chloro-4-(2-hydroxy-1,2-oxaborolan-4-yl)phenyl)methylsulfonamido)-5-cyclopropyl-2-(4-fluorophenyl)-N-methylbenzofuran-3-carboxamide Bis(1,5-cyclooctadiene)diiridium(I) dichloride (2.054 mg, 3.06 μmol) and diphenylphosphinobutane (2.61 mg, 6.12 μmol) were dissolved in THF (1 mL) under nitrogen. A solution of 6-(N-(3-chloro-4-(3-(methoxymethoxy)prop-1-en-2-yl)phenyl)methylsulfonamido)-5-cyclopropyl-2-(4-fluorophenyl)-N-methylbenzofuran-3-carboxamide (75 mg, 0.122 mmol) in THF (1 mL) was added. After stirring for 10 min, pinacolborane (1M in THF) (0.367 mL, 0.367 mmol) was added and the mixture was stirred at room temperature for 18 hours. The solvent was evaporated and the residue was subjected to silica gel chromatography with hexane:EtOAc to give a mixture containing 47% of the title compound. To this material was added THF (1 mL) and 1N aqueous HCl (1 mL, 1.00 mmol). After heating at 70° C. for 18 hours, the solvent was evaporated and the residue was purified by reverse phase HPLC (C18, acetonitrile:water with 0.1% formic acid) to give the title compound (7.8 mg, 10.2%) as a white solid. $^1$H NMR (400 MHz, DMSO-d$_6$) δ ppm 8.71 (s, 1H) 8.41-8.50 (m, 1H) 8.11 (s, 1H) 7.90-8.01 (m, 2H) 7.32-7.52 (m, 5H) 7.17 (s, 1H) 4.12-4.27 (m, 1H) 3.62-3.83 (m, 2H) 3.39 (s, 3H) 2.82 (d, J=4.69 Hz, 3H) 2.09-2.22 (m, 1H) 1.17-1.32 (m, 1H) 0.92-1.06 (m, 2H) 0.72-0.90 (m, 2H) 0.46 (m, 1H). LCMS (m/z, ES+)=597 (M+H+).

Example 26

(3-(N-(5-Cyclopropyl-2-(4-fluorophenyl)-3-(methylcarbamoyl)benzofuran-6-yl)methylsulfonamido)phenethyl)boronic acid

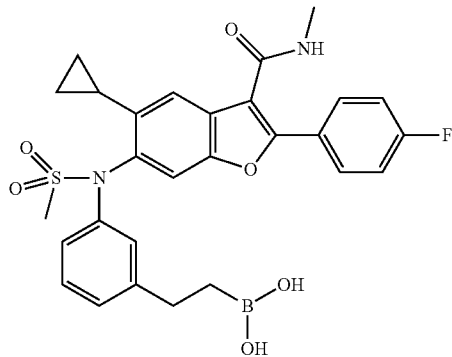 [SMILES: CNC(=O)c1c(-c2ccc(F)cc2)oc2cc(N(c3cccc(CCB(O)O)c3)S(C)(=O)=O)c(C3CC3)cc12]

Step 1: Ethyl 6-((3-bromophenyl)amino)-5-cyclopropyl-2-(4-fluorophenyl)benzofuran-3-carboxylate A mixture of ethyl 6-amino-5-cyclopropyl-2-(4-fluorophenyl)benzofuran-3-carboxylate (1.00 g, 2.95 mmol), (3-bromophenyl)boronic acid (1.184 g, 5.89 mmol), copper (II) acetate (0.803 g, 4.42 mmol), triethylamine (1.232 mL, 8.84 mmol) and 4 A molecular sieves (2 g) was stirred at room temperature for 24 hours. The reaction mixture was diluted with EtOAc and filtered through Celite. The solvent was evaporated and the residue was purified by chromatography on silica gel (hexane:EtOAc) to give ethyl 6-((3-bromophenyl)amino)-5-cyclopropyl-2-(4-fluorophenyl)benzofuran-3-carboxylate (740 mg, 51%). LCMS (m/z, ES+)=494, 496 (M+H, M+2).

Step 2: Ethyl 6-(N-(3-bromophenyl)methylsulfonamido)-5-cyclopropyl-2-(4-fluorophenyl)benzofuran-3-carboxylate A solution of lithium bis(trimethylsilyl)amide (1M in THF) (1.93 mL, 1.93 mmol) was added dropwise to a solution of ethyl 6-((3-bromophenyl)amino)-5-cyclopropyl-2-(4-fluorophenyl)benzofuran-3-carboxylate (734 mg, 1.48 mmol) in THF (10 mL) at −78° C. The mixture was stirred for 45 minutes and then a solution of methanesulfonyl chloride (0.463 mL, 5.94 mmol) in THF (1.5 mL) was added at −78° C. After complete addition the reaction mixture was allowed to warm to room temperature overnight. Water and EtOAc were added. The organic layer was washed with water and brine, dried over sodium sulfate and concentrated. The residue was purified by silica gel chromatography (hexane:EtOAc) to give ethyl 6-(N-(3-bromophenyl)methylsulfonamido)-5-cyclopropyl-2-(4-fluorophenyl)benzofuran-3-carboxylate (318 mg, 37%) as a yellow solid. $^1$H NMR (400 MHz, DMSO-d$_6$) δ ppm 8.20 (s, 1H) 8.03-8.13 (m, 2H) 7.62-7.66 (m, 1H) 7.59 (s, 1H) 7.43 (s, 4H) 7.30-7.39 (m, 1H) 4.26-4.41 (m, 2H) 3.42 (s, 3H) 2.12-2.26 (m, 1H) 1.28-1.37 (m, 3H) 0.71-1.14 (m, 4H) 0.41 (m, 1H). %). LCMS (m/z, ES+)=572, 574 (M+H, M+2).

Step 3: 6-(N-(3-Bromophenyl)methylsulfonamido)-5-cyclopropyl-2-(4-fluorophenyl)benzofuran-3-carboxylic acid Lithium hydroxide monohydrate (68.5 mg, 1.630 mmol) was added to a suspension of ethyl 6-(N-(3-bromophenyl)methylsulfonamido)-5-cyclopropyl-2-(4-fluorophenyl)benzofuran-3-carboxylate (311 mg, 0.543 mmol) in THF:MeOH:water/3:1:1 (10 mL). The mixture was stirred at room temperature overnight. The mixture was acidified with 2N aqueous HCl and the volatile solvents were evaporated. The residue was partitioned between EtOAc and water. The organic layers were washed with brine, dried over sodium sulfate and concentrated to give 6-(N-(3-bromophenyl)methylsulfonamido)-5-cyclopropyl-2-(4-fluorophenyl)benzofuran-3-carboxylic acid (309 mg, quantitative) as a yellow solid. $^1$H NMR (400 MHz, CHLOROFORM-d) δ ppm 8.01-8.13 (m, 2H) 7.77 (s, 1H) 7.66 (s, 1H) 7.54 (t, J=1.95 Hz, 1H) 7.39 (dd, J=8.21, 1.37 Hz, 1H) 7.30-7.36 (m, 1H) 7.17-7.26 (m, 3H) 3.27 (s, 3H) 2.11 (s, 1H) 0.74-1.18 (m, 3H) 0.48-0.74 (m, 1H). LCMS (m/z, ES+)=544, 546 (M+H, M+2).

Step 4: 6-(N-(3-Bromophenyl)methylsulfonamido)-5-cyclopropyl-2-(4-fluorophenyl)-N-methylbenzofuran-3-carboxamide HATU (237 mg, 0.624 mmol) was added to a solution of 6-(N-(3-bromophenyl)methylsulfonamido)-5-cyclopropyl-2-(4-fluorophenyl)benzofuran-3-carboxylic acid (283 mg, 0.520 mmol), methylamine hydrochloride (70.2 mg, 1.040 mmol) and DIEA (0.318 mL, 1.819 mmol) in DMF (2 mL) at room temperature. The mixture was stirred for one hour. The reaction mixture was diluted with EtOAc. The organic layer was washed with water and brine, dried over sodium sulfate and concentrated. The residue was purified by silica gel chromatography (hexane:ethyl acetate) to give 6-(N-(3-bromophenyl)methylsulfonamido)-5-cyclopropyl-2-(4-fluorophenyl)-N-methylbenzofuran-3-carboxamide (230 mg, 79%) as a light yellow solid. $^1$H NMR (400 MHz, DMSO-d$_6$) δ ppm 8.47 (s, 1H) 8.12 (s, 1H) 7.96 (dd, J=8.98, 5.47 Hz, 2H) 7.60 (t, J=2.05 Hz, 1H) 7.27-7.54 (m, 5H) 7.18 (s, 1H) 3.41 (s, 3H) 2.82 (d, J=4.69 Hz, 3H) 2.07-2.22 (m, 1H) 0.65-1.09 (m, 3H) 0.41 (m, 1H). LCMS (m/z, ES+)=557, 559 (M+H, M+2).

Step 5: 5-Cyclopropyl-2-(4-fluorophenyl)-N-methyl-6-(N-(3-vinylphenyl)methylsulfonamido)benzofuran-3-carboxamide A mixture of 6-(N-(3-bromophenyl)methylsulfonamido)-5-cyclopropyl-2-(4-fluorophenyl)-N-methylbenzofuran-3-carboxamide (221 mg, 0.396 mmol), 4,4,5,5-tetramethyl-2-vinyl-1,3,2-dioxaborolane (0.134 mL, 0.793 mmol), [1,1'-bis(diphenylphosphino)ferrocene]-dichloropalladium(II), complex with dichloromethane (32.4 mg, 0.040 mmol) and sodium carbonate (126 mg, 1.189 mmol) in dioxane:water/4:1 (5 mL) was heated in a microwave reactor at 130° C. for 30 minutes. The reaction mixture was diluted with EtOAc and filtered through Celite. The solvent was evaporated and the residue was purified by silica gel chromatography (hexane:EtOAc) to give 5-cyclopropyl-2-(4-fluorophenyl)-N-methyl-6-(N-(3-vinylphenyl)methylsulfonamido)benzofuran-3-carboxamide (171 mg, 85% purity) as a sticky off-white foam. LCMS (m/z, ES+)=505 (M+H+). This material was taken to the next step without further purification.

Step 6: 5-Cyclopropyl-2-(4-fluorophenyl)-N-methyl-6-(N-(3-(2-(4,4,5,5-tetramethyl-1,3,2-dioxaborolan-2-yl)ethyl)phenyl)methylsulfonamido)benzofuran-3-carboxamide Bis(1,5-cyclooctadiene)diiridium(I) dichloride (5.29 mg, 7.88 μmol) and diphenylphosphinobutane (6.72 mg, 0.016 mmol) were dissolved in THF (2 mL) under nitrogen. A suspension of 5-cyclopropyl-2-(4-fluorophenyl)-N-methyl-6-(N-(3-vinylphenyl)methylsulfonamido)benzofuran-3-carboxamide (159 mg, 0.315 mmol) in THF (2 mL) was added. After stirring for 10 min, pinacolborane (1M in THF) (0.95 mL, 0.945 mmol) was added and the mixture was stirred at room temperature for 2 hours. The solvent was evaporated and the residue was subjected to silica gel chromatography (dichloromethan:methanol) to give 5-cyclopropyl-2-(4-fluorophenyl)-N-methyl-6-(N-(3-(2-(4,4,5,5-tetramethyl-1,3,2-dioxaborolan-2-yl)ethyl)phenyl)methylsulfonamido)benzofuran-3-carboxamide (75 mg, 38%, 82% purity. This material was taken to next step without further purification. LCMS (m/z, ES$^+$)=633 (M+H+).

Step 7: (3-(N-(5-Cyclopropyl-2-(4-fluorophenyl)-3-(methylcarbamoyl)benzofuran-6-yl)methylsulfonamido)phenethyl)boronic acid Sodium periodate (380 mg, 1.78 mmol) and 1N aqueous HCl (1.5 mL, 1.5 mmol) were added to a cold (0° C.) solution of 5-cyclopropyl-2-(4-fluorophenyl)-N-methyl-6-(N-(3-(2-(4,4,5,5-tetramethyl-1,3,2-dioxaborolan-2-yl)ethyl)phenyl)methylsulfonamido)benzofuran-3-carboxamide (75 mg, 0.119 mmol) in THF (3 mL). The mixture was stirred at 0° C. for 10 min then warmed to room temperature. After one hour, the reaction mixture was diluted with EtOAc and the organic layer was separated and washed with 5% aqueous sodium thiosulfate and brine and dried over sodium sulfate. The solvent was evaporated and the residue was subjected to reverse phase HPLC (C18, acetonitrile:water with 0.1% formic acid) to give the title compound (22 mg, 34%) as a white powder. $^1$H NMR (400 MHz, DMSO-d$_6$) d ppm 8.42-8.53 (m, 1H) 8.06-8.13 (m, 1H) 7.92-8.02 (m, 2H) 7.55 (s, 2H) 7.34-7.46 (m, 3H) 7.24-7.30 (m, 2H) 7.14-7.18 (m, 1H) 7.04-7.11 (m, 1H) 2.83 (d, J=4.68 Hz, 3H) 2.58-2.67 (m, 2H) 2.48-2.55 (m, 3H) 2.15-2.31 (m, 1H) 0.94-1.11 (m, 1H) 0.75-0.94 (m, 4H) 0.47 (m, 1H). LCMS (m/z, ES$^+$)=551 (M+H+).

Example 27

6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide

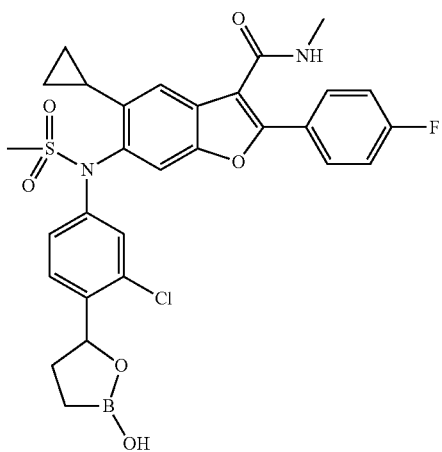 [SMILES: CNC(=O)c1c(-c2ccc(F)cc2)oc2cc(N(c3ccc(C4CCB(O)O4)c(Cl)c3)S(C)(=O)=O)c(C3CC3)cc12]

Step 1: 6-(N-(3-Chloro-4-vinylphenyl)methylsulfonamido)-5-cyclopropyl-2-(4-fluorophenyl)-N-methylbenzofuran-3-carboxamide A mixture of 6-(N-(4-bromo-3-chlorophenyl)methylsulfonamido)-5-cyclopropyl-2-(4-fluorophenyl)-N-methylbenzofuran-3-carboxamide (1.00 g, 1.69 mmol), PdCl$_2$(dppf)-CH$_2$Cl$_2$ adduct (138 mg, 0.169 mmol), sodium carbonate (537 mg, 5.07 mmol) and vinylboronic acid pinacol ester (0.573 mL, 3.38 mmol) in a 9:1 mixture of 1,4-dioxane and water (20 mL) was degassed and heated at 80° for 16 h. The mixture was cooled to rt, then poured into water and extracted with EtOAc (3×). The combined organic layers were washed with brine (1×), dried over sodium sulfate and concentrated under reduced pressure. The light brown oily residue was purified by flash chromatography (silica gel, gradient of 0 to 50% EtOAc in hexanes) to afford the title compound (821 mg, 90%) as a white solid. $^1$H NMR (400 MHz, DMSO-d$_6$) δ ppm 8.46 (q, 1H), 8.08-8.14 (m, 1H), 7.92-8.02 (m, 2H), 7.70-7.76 (m, 1H), 7.34-7.47 (m, 4H), 7.17-7.24 (m, 1H), 6.96 (dd, 1H), 5.87 (d, 1H), 5.44 (d, 1H), 3.39-3.47 (m, 3H), 2.83 (d, 3H), 2.04-2.16 (m, 1H), 0.73-1.03 (m, 3H), 0.36-0.55 (m, 1H). LCMS (m/z, ES$^+$)=539 (M+H+).

Step 2: 6-(N-(3-Chloro-4-formylphenyl)methylsulfonamido)-5-cyclopropyl-2-(4-fluorophenyl)-N-methylbenzofuran-3-carboxamide A suspension of 6-(N-(3-chloro-4-vinylphenyl)methylsulfonamido)-5-cyclopropyl-2-(4-fluorophenyl)-N-methylbenzofuran-3-carboxamide (890 mg, 1.65 mmol) in 1:1 THF/water (36 mL) was treated with a solution of osmium tetroxide (2.5% in t-butanol, 0.415 mL, 0.033 mmol) and stirred for a few minutes. The resulting solution was treated with sodium periodate (883 mg, 4.13 mmol) and the reaction mixture was stirred for 16 h at rt. The reaction mixture was diluted with EtOAc and washed with 1:1 water/brine (1×), then brine (1×). The organic layer was dried over sodium sulfate and concentrated under reduced pressure. The residue was dissolved in dichloromethane, filtered and the filtrate was purified by flash chromatography (silica gel, gradient of 0 to 50% EtOAc in hexanes) to afford the title compound (0.45 g, 50%) as a white solid. $^1$H NMR (400 MHz, DMSO-d$_6$) δ ppm 10.23 (s, 1H), 8.45-8.53 (m, 1H), 8.04 (s, 1H), 7.94-8.01 (m, 2H), 7.86 (d, 1H), 7.35-7.46 (m, 3H), 7.31 (dd, 1H), 7.24-7.29 (m, 1H), 3.57 (s, 3H), 2.84 (d, 3H), 1.89-1.98 (m, 1H), 0.68-1.02 (m, 3H), 0.42-0.58 (m, 1H). LCMS (m/z, ES$^+$)=541 (M+H+).

Step 3: 6-(N-(3-Chloro-4-(1-hydroxyallyl)phenyl)methylsulfonamido)-5-cyclopropyl-2-(4-fluorophenyl)-N-methylbenzofuran-3-carboxamide A solution of 6-(N-(3-chloro-4-formylphenyl)methylsulfonamido)-5-cyclopropyl-2-(4-fluorophenyl)-N-methylbenzofuran-3-carboxamide (0.25 g, 0.46 mmol) in THF (10 mL) was cooled to 0° and treated with vinylmagnesium bromide (1 M in THF, 1.02 mL). The reaction mixture was allowed to warm to rt as the bath melted. After 5 h, the reaction mixture was poured into saturated ammonium chloride and extracted with EtOAc (2×). The combined organic layers were dried over sodium sulfate and concentrated under reduced pressure. Purification by flash chromatography (silica gel, gradient of 0 to 60% EtOAc in hexanes) afforded the title compound (188 mg, 72%) as a white foam. $^1$H NMR (400 MHz, DMSO-d$_6$) δ ppm 8.45 (q, 1H), 8.11 (s, 1H), 7.93-8.01 (m, 2H), 7.36-7.56 (m, 5H), 7.18 (s, 1H), 5.90 (ddd, 1H), 5.71 (d, 1H), 5.35 (t, 1H), 5.22 (dt, 1H), 5.04-5.11 (m, 1H), 3.40 (s, 3H), 2.83 (d, 3H), 2.09-2.19 (m, 1H), 0.76-1.07 (m, 3H), 0.39-0.54 (m, 1H). LCMS (m/z, ES$^+$)=569 (M+H+).

Step 4: 6-(N-(3-Chloro-4-(1-(methoxymethoxy)allyl)phenyl)methylsulfonamido)-5-cyclopropyl-2-(4-fluorophenyl)-N-methylbenzofuran-3-carboxamide To a solution of 6-(N-(3-chloro-4-(1-hydroxyallyl)phenyl)methylsulfonamido)-5-cyclopropyl-2-(4-fluorophenyl)-N-methylbenzofuran-3-carboxamide (210 mg, 0.37 mmol) in THF (7 mL) was added DIEA (0.084 mL, 0.48 mmol) and chloromethyl methyl ether (0.16 mL, 2.12 mmol). The reaction mixture was heated at 50° overnight. Another portion of DIEA (0.32 mL, 1.85 mmol) was added and heating was continued for another 5 h. The reaction mixture was cooled to rt, diluted with water and extracted with EtOAc (2×). The combined organic layers were washed with brine (1×), dried over sodium sulfate and concentrated under reduced pressure. Purification by flash chromatography (silica gel, gradient of 0 to 60% EtOAc in hexanes) afforded the title compound (175 mg, 77%) as a colorless oil. $^1$H NMR (400 MHz, DMSO-$d_6$) δ ppm 8.45 (q, 1H), 8.10 (s, 1H), 7.93-8.00 (m, 2H), 7.36-7.53 (m, 5H), 7.19 (s, 1H), 5.88 (ddd, 1H), 5.38 (d, 1H), 5.18-5.30 (m, 2H), 4.66 (d, 1H), 4.53 (d, 1H), 3.38-3.46 (m, 3H), 3.23 (s, 3H), 2.83 (d, 3H), 2.08-2.17 (m, 1H), 0.92-1.06 (m, 1H), 0.75-0.91 (m, 2H), 0.39-0.51 (m, 1H). LCMS (m/z, ES$^+$)=613 (M+H+).

Step 5: 6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide A solution of 6-(N-(3-chloro-4-(1-(methoxymethoxy)allyl)phenyl)methylsulfonamido)-5-cyclopropyl-2-(4-fluorophenyl)-N-methylbenzofuran-3-carboxamide (125 mg, 0.20 mmol) in THF (10 mL) was treated with Rh(CO)Cl(PPh$_3$)$_2$ (14 mg, 0.02 mmol), purged with nitrogen and treated with a solution of pinacolborane (1 M in THF, 1.22 mL). After stirring overnight at rt, the reaction mixture was concentrated. The residue was dissolved in THF (10 mL) and treated with (Ir(COD)Cl)$_2$ (13.7 mg, 0.02 mmol) and DPPE (16.3 mg, 0.041 mmol). After stirring for 5 min, a solution of pinacolborane (1 M in THF, 1.22 mL) was added. The reaction mixture was stirred for 2 h and concentrated under reduced pressure. Separately, the above procedure was repeated, using the same sequence of steps, on 6-(N-(3-chloro-4-(1-(methoxymethoxy)allyl)phenyl)methylsulfonamido)-5-cyclopropyl-2-(4-fluorophenyl)-N-methylbenzofuran-3-carboxamide (49 mg, 0.08 mmol), using proportional quantities of identical reagents. Both of these residues were subjected to purification by flash chromatography (silica gel, gradient of 0 to 100% EtOAc in hexanes) to afford a pale yellow oil which was carried forward without characterization. The oil was dissolved in THF (5 mL) and 1N HCl (5 mL) and heated at 70° for 16 h, at which time methanol (1 mL) was added and the heating continued for 1 h. The reaction mixture was cooled to rt, diluted with water and extracted with EtOAc (2×). The combined organic layers were washed with brine (1×), dried over sodium sulfate and concentrated under reduced pressure. Purification by flash chromatography (silica gel, gradient of 0 to 100% ethyl acetate in dichloromethane, then 0 to 3.5% methanol in dichloromethane) afforded the title compound (32 mg, 19% over 2 steps) as an off-white foam. $^1$H NMR (400 MHz, DMSO-$d_6$) δ ppm 8.79 (s, 1H), 8.45 (q, 1H), 8.12 (s, 1H), 7.91-8.01 (m, 2H), 7.34-7.54 (m, 5H), 7.18 (s, 1H), 5.32 (t, 1H), 3.38-3.44 (m, 3H), 2.83 (d, 3H), 2.36-2.46 (m, 1H), 2.09-2.21 (m, 1H), 1.49-1.63 (m, 1H), 0.76-1.09 (m, 5H), 0.35-0.55 (m, 1H). LCMS (m/z, ES$^+$)=597 (M+H+).

Example 28

6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide, enantiomer 1

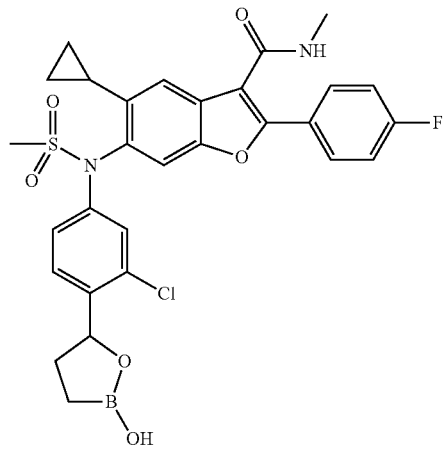 [SMILES: CNC(=O)c1c(-c2ccc(F)cc2)oc2cc(N(c3ccc(C4CCB(O)O4)c(Cl)c3)S(C)(=O)=O)c(C3CC3)cc12]

Step 1: 6-(N-(3-Chloro-4-(1-hydroxyallyl)phenyl)methylsulfonamido)-5-cyclopropyl-2-(4-fluorophenyl)-N-methylbenzofuran-3-carboxamide, enantiomers 1 and 2

A solution of 6-(N-(3-chloro-4-formylphenyl)methylsulfonamido)-5-cyclopropyl-2-(4-fluorophenyl)-N-methylbenzofuran-3-carboxamide (1.17 g, 2.16 mmol) in THF (20 mL) was cooled to 0° and treated with vinylmagnesium bromide (1 M in THF, 4.76 mL). The reaction mixture was allowed to warm to rt as the bath melted. An additional portion of vinylmagnesium bromide (0.43 mL,) was added after a few h. Stirring was continued and the reaction mixture was poured into saturated ammonium chloride and extracted with EtOAc (2×). The combined organic layers were dried over sodium sulfate and concentrated under reduced pressure. Purification by flash chromatography (silica gel, gradient of 0 to 60% EtOAc in hexanes) afforded the title compound (0.87 g, 71%) as a white foam. Enantiomers were separated by supercritical fluid chromatography (Chiral Tech ADH, 30% methanol, 140 bar, 40° C., 90 mL/min). Both enantiomers were white foams. The earlier eluting enantiomer 1 weighed 380 mg and the later eluting enantiomer 2 weighed 370 mg. Enantiomer #1 $^1$H NMR (400 MHz, DMSO-$d_6$) δ ppm 8.44 (q, 1H), 8.11 (s, 1H), 7.93-8.01 (m, 2H), 7.35-7.55 (m, 5H), 7.18 (s, 1H), 5.90 (ddd, 1H), 5.70 (d, 1H), 5.35 (t, 1H), 5.22 (dt, 1H), 5.08 (dt, 1H), 3.40 (s, 3H), 2.83 (d, 3H), 2.10-2.20 (m, 1H), 0.77-1.06 (m, 3H), 0.40-0.53 (m, 1H). LCMS (m/z, ES$^+$)=569 (M+H+). Enantiomer #2 $^1$H NMR (400 MHz, DMSO-$d_6$) δ ppm 8.44 (q, 1H), 8.11 (s, 1H), 7.93-8.01 (m, 2H), 7.36-7.56 (m, 5H), 7.18 (s, 1H), 5.90 (ddd, 1H), 5.70 (d, 1H), 5.35 (t, 1H), 5.22 (dt, 1H), 5.08 (dt, 1H), 3.40 (s, 3H), 2.83 (d, 3H), 2.09-2.20 (m, 1H), 0.76-1.06 (m, 3H), 0.40-0.54 (m, 1H). LCMS (m/z, ES$^+$)=569 (M+H+).

Step 2: 6-(N-(3-Chloro-4-(1-(methoxymethoxy)allyl)phenyl)methylsulfonamido)-5-cyclopropyl-2-(4-fluorophenyl)-N-methylbenzofuran-3-carboxamide, enantiomer 1

To a solution of 6-(N-(3-chloro-4-(1-hydroxyallyl)phenyl)methylsulfonamido)-5-cyclopropyl-2-(4-fluorophenyl)-N-methylbenzofuran-3-carboxamide, enantiomer 1 (350 mg, 0.62 mmol) in THF (10 mL) was added DIEA (0.32 mL, 1.85 mmol) and chloromethyl methyl ether (0.12 mL, 1.54 mmol). The reaction mixture was heated at 50° overnight. Additional portions of DIEA (0.32 mL, 1.85 mmol) and chloromethyl methyl ether (0.12 mL, 1.54 mmol) were added and heating was continued for another 24 h. The reaction mixture was cooled to rt, diluted with water and extracted with EtOAc (2×). The combined organic layers were washed with brine (1×), dried over sodium sulfate and concentrated under reduced pressure. Purification by flash chromatography (silica gel, gradient of 0 to 50% EtOAc in hexanes) afforded the title compound (350 mg, 93%) as a colorless semisolid. $^1$H NMR (400 MHz, DMSO-$d_6$) δ ppm 8.46 (q, 1H), 8.10 (s, 1H), 7.91-7.99 (m, 2H), 7.35-7.52 (m, 5H), 7.18 (s, 1H), 5.87 (ddd, 1H), 5.36 (d, 1H), 5.17-5.29 (m, 2H), 4.65 (d, 1H), 4.52 (d, 1H), 3.42 (s, 3H), 3.22 (s, 3H), 2.82 (d, 3H), 2.05-2.17 (m, 1H), 0.92-1.04 (m, 1H), 0.73-0.89 (m, 2H), 0.37-0.50 (m, 1H). LCMS (m/z, ES$^+$)=613 (M+H+).

Step 5: 6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide, enantiomer 1

A solution of 6-(N-(3-chloro-4-(1-(methoxymethoxy)allyl)phenyl)methylsulfonamido)-5-cyclopropyl-2-(4-fluorophenyl)-N-methylbenzofuran-3-carboxamide, enantiomer 1 (52 mg, 0.085 mmol) in THF (5 mL) was treated with (Ir(COD)Cl)$_2$ (5.7 mg, 8.5 μmol) and DPPE (6.8 mg, 0.017 mmol). After stirring for 25 min, a solution of pinacolborane (1 M in THF, 0.25 mL) was added. The reaction mixture was stirred for 0.5 h and concentrated under reduced pressure. Separately, the above procedure was repeated, using proportional quantities of reagents, on 6-(N-(3-chloro-4-(1-(methoxymethoxy)allyl)phenyl)methylsulfonamido)-5-cyclopropyl-2-(4-fluorophenyl)-N-methylbenzofuran-3-carboxamide, enantiomer 1 (296 mg, 0.48 mmol). The two residues were subjected to purification by flash chromatography (silica gel, gradient of 0 to 100% EtOAc in hexanes) to afford a colorless oil which was carried forward without characterization. The oil was dissolved in THF (10 mL), 1N HCl (10 mL) and MeOH (1 mL) and heated at 70° for 16 h. The reaction mixture was cooled to rt, diluted with water and extracted with EtOAc (2×). The combined organic layers were washed with brine (1×), dried over sodium sulfate and concentrated under reduced pressure. Purification by flash chromatography (silica gel, gradient of 0 to 100% ethyl acetate in dichloromethane, then 0 to 3.5% methanol in dichloromethane) followed by lyophilization afforded the title compound (85 mg, 25% over 2 steps) as a fluffy white solid. $^1$H NMR (400 MHz, DMSO-$d_6$) δ ppm 8.79 (s, 1H), 8.40-8.49 (m, 1H), 8.12 (s, 1H), 7.92-8.03 (m, 2H), 7.34-7.56 (m, 5H), 7.19 (s, 1H), 5.29-5.37 (m, 1H), 3.38-3.46 (m, 3H), 2.84 (d, 3H), 2.37-2.47 (m, 1H), 2.10-2.22 (m, 1H), 1.50-1.73 (m, 1H), 0.75-1.08 (m, 5H), 0.37-0.56 (m, 1H). LCMS (m/z, ES$^+$)=597 (M+H+).

Example 29

6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide, enantiomer 2

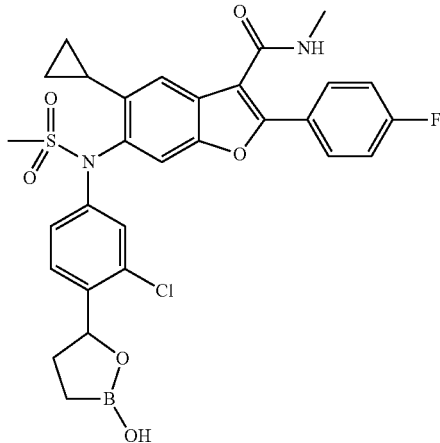 [SMILES: CNC(=O)c1c(-c2ccc(F)cc2)oc2cc(N(c3ccc(C4CCB(O)O4)c(Cl)c3)S(C)(=O)=O)c(C3CC3)cc12]

Step 1: 6-(N-(3-Chloro-4-(1-(methoxymethoxy)allyl)phenyl)methylsulfonamido)-5-cyclopropyl-2-(4-fluorophenyl)-N-methylbenzofuran-3-carboxamide, enantiomer 2

To a solution of 6-(N-(3-chloro-4-(1-hydroxyallyl)phenyl)methylsulfonamido)-5-cyclopropyl-2-(4-fluorophenyl)-N-methylbenzofuran-3-carboxamide, enantiomer 2 (340 mg, 0.58 mmol) in THF (7 mL) was added DIEA (0.42 mL, 2.39 mmol) and chloromethyl methyl ether (0.14 mL, 1.79 mmol). The reaction mixture was heated at 50° overnight. Additional portions of DIEA (0.42 mL, 2.39 mmol) and chloromethyl methyl ether (0.14 mL, 1.79 mmol) were added and heating was continued for another 24 h. The reaction mixture was cooled to rt, diluted with water and extracted with EtOAc (2×). The combined organic layers were washed with brine (1×), dried over sodium sulfate and concentrated under reduced pressure. Purification by flash chromatography (silica gel, gradient of 0 to 50% EtOAc in hexanes) afforded the title compound (342 mg, 93%) as a colorless semisolid. $^1$H NMR (400 MHz, DMSO-$d_6$) δ ppm 8.45-8.51 (m, 1H), 8.12 (s, 1H), 7.94-8.02 (m, 2H), 7.37-7.54 (m, 5H), 7.20 (s, 1H), 5.89 (ddd, 1H), 5.38 (d, 1H), 5.18-5.32 (m, 2H), 4.67 (d, 1H), 4.54 (d, 1H), 3.44 (s, 3H), 3.24 (s, 3H), 2.84 (d, 3H), 2.08-2.19 (m, 1H), 0.77-1.06 (m, 3H), 0.41-0.51 (m, 1H). LCMS (m/z, ES$^+$)=613 (M+H+).

Step 2: 6-(N-(3-Chloro-4-(2-hydroxy-1,2-oxaborolan-5-yl)phenyl)methylsulfonamido)-5-cyclopropyl-2-(4-fluorophenyl)-N-methylbenzofuran-3-carboxamide, enantiomer 2

A solution of 6-(N-(3-chloro-4-(1-(methoxymethoxy)allyl)phenyl)methylsulfonamido)-5-cyclopropyl-2-(4-fluorophenyl)-N-methylbenzofuran-3-carboxamide, enantiomer 2 (340 mg, 0.56 mmol) in THF (15 mL) was treated with (Ir(COD)Cl)$_2$ (37 mg, 0.055 mmol) and DPPE (44 mg, 0.11 mmol). After stirring for 30 min, a solution of pinacolborane (1 M in THF, 1.66 mL) was added. The reaction mixture was stirred for 0.5 h and concentrated under reduced pressure. The residue was subjected to purification by flash chromatography (silica gel, gradient of 0 to 100% EtOAc in hexanes) to afford a colorless oil which was carried forward without characterization. The oil was dissolved in THF (10 mL), 1N HCl (10 mL) and MeOH (1 mL) and heated at 70° for 16 h. The reaction mixture was cooled to rt, diluted with water and extracted with EtOAc (2×). The combined organic layers were washed with brine (1×), dried over sodium sulfate and concentrated under reduced pressure. Purification by flash chromatography (silica gel, gradient of 0 to 100% ethyl acetate in dichloromethane, then 0 to 3.5% methanol in dichloromethane) followed by lyophilization afforded the title compound (124 mg, 38% over 2 steps) as a fluffy white solid. $^1$H NMR (400 MHz, DMSO-d$_6$) δ ppm 8.79 (s, 1H), 8.42-8.49 (m, 1H), 8.12 (s, 1H), 7.93-8.02 (m, 2H), 7.35-7.55 (m, 5H), 7.19 (s, 1H), 5.33 (t, 1H), 3.39-3.45 (m, 3H), 2.84 (d, 3H), 2.37-2.47 (m, 1H), 2.12-2.22 (m, 1H), 1.49-1.64 (m, 1H), 0.77-1.07 (m, 5H), 0.41-0.52 (m, 1H). LCMS (m/z, ES$^+$)=597 (M+H+).

Example 30

5-Cyclopropyl-2-(4-fluorophenyl)-6-(N-(1-hydroxy-3,4-dihydro-1H-benzo[c][1,2]oxaborinin-6-yl)methylsulfonamido)-N-methylbenzofuran-3-carboxamide

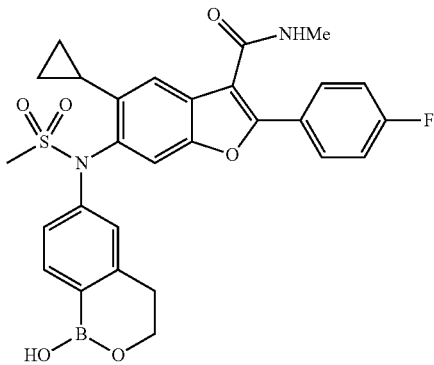 [SMILES: CNC(=O)c1c(-c2ccc(F)cc2)oc2cc(N(c3ccc4c(c3)CCOB4O)S(C)(=O)=O)c(C3CC3)cc12]

Step 1: Dimethyl 2-(5-(N-(5-cyclopropyl-2-(4-fluorophenyl)-3-(methylcarbamoyl)benzofuran-6-yl)methylsulfonamido)-2-nitrophenyl)malonate To a stirred suspension of Cs$_2$CO$_3$ (17.5 g, 53.8 mmol) in DMF (20 ml) under a nitrogen atmosphere was added dimethyl malonate (2.57 mL, 22.4 mmol) at room temperature. This was followed by the addition of a sonicated solution of 6-(N-(3-chloro-4-nitrophenyl)methylsulfonamido)-5-cyclopropyl-2-(4-fluorophenyl)-N-methylbenzofuran-3-carboxamide (10.0 g, 17.9 mmol) in DMF (50 mL) at room temperature by dropwise addition. The reaction mixture was stirred at room temperature for 24 h. The reaction mixture was diluted with water and extracted with EtOAc (3×40 mL). The organic layer was washed with water (3×50 mL), dried over sodium sulfate and evaporated to dryness. The crude product triturated with ether and the solid collected by filtration to afford the title compound in 68% yield. $^1$H NMR (400 MHz, DMSO-d6) δ ppm 8.51 (d, J=4.7 Hz, 1H), 8.19 (d, J=9.2 Hz, 1H), 8.04 (s, 1H), 7.90-8.00 (m, 2H), 7.36-7.51 (m, 3H), 7.26-7.31 (m, 1H), 7.14-7.20 (m, 1H), 5.45-5.56 (m, 1H), 3.52-3.64 (m, 9H), 2.84 (d, J=4.5 Hz, 3H), 1.88-2.03 (m, 1H), 0.82-1.00 (m, 2H), 0.69 (d, J=3.1 Hz, 1H), 0.29-0.50 (m, 1H). LCMS (m/z, ES$^+$)=654 (M+H+).

Step 2: 2-(5-(N-(5-Cyclopropyl-2-(4-fluorophenyl)-3-(methylcarbamoyl)benzofuran-6-yl)methylsulfonamido)-2-nitrophenyl)acetic acid To a stirred solution of dimethyl 2-(5-(N-(5-cyclopropyl-2-(4-fluorophenyl)-3-(methylcarbamoyl)benzofuran-6-yl)methylsulfonamido)-2-nitrophenyl)malonate (10.0 g, 15.3 mmol) in 1:1:1 THF/MeOH/water, was added 3N aqueous NaOH (20 mL). The resulting mixture was heated at 55° C. for 15 h. The reaction mixture was cooled to room temperature and treated with 5N aqueous HCl to pH 5. The aqueous layer was extracted with ethyl acetate (3×30 mL). The organic layer was washed with water, dried over sodium sulfate and evaporated to dryness. The residue was triturated with methanol and ether and the solid collected by filtration to give the title compound in 75% yield. $^1$H NMR (400 MHz, DMSO-d6) δ ppm 12.52 (br. s., 1H) 8.49 (q, J=4.23 Hz, 1H) 8.09-8.15 (m, 1H) 8.02 (s, 1H) 7.96 (d, J=3.32 Hz, 4H) 7.31-7.44 (m, 4H) 7.25 (s, 1H) 3.98 (s, 2H) 3.56 (s, 3H) 2.84 (d, J=4.69 Hz, 3H) 1.94-2.03 (m, 1H) 0.85 (d, J=3.13 Hz, 3H) 0.48 (br. s., 1H). LCMS (m/z, ES$^+$)=583 (M+H+).

Step 3: Methyl 2-(5-(N-(5-cyclopropyl-2-(4-fluorophenyl)-3-(methylcarbamoyl)benzofuran-6-yl)methylsulfonamido)-2-nitrophenyl)acetate To a stirred solution of 2-(5-(N-(5-cyclopropyl-2-(4-fluorophenyl)-3-(methylcarbamoyl)benzofuran-6-yl)methylsulfonamido)-2-nitrophenyl)acetic acid (2.00 g, 3.44 mmol) in 10 mL of 1:1 DMF/MeOH was added 2 M TMS-diazomethane in hexane (0.786 g, 6.88 mmol) at 0° C. and reaction mixture stirred for 2 h. The reaction was diluted with water and extracted into EtOAc. The ethyl acetate solution was washed with water, dried over sodium sulfate and evaporated to dryness to give the title compound in 70% yield. $^1$H NMR (400 MHz, CHLOROFORM-d) δ ppm 8.04 (d, J=9.19 Hz, 1H) 7.88 (br. s., 0H) 7.80 (t, J=6.06 Hz, 2H) 7.46 (s, 1H) 7.44 (br. s., 1H) 7.28 (dd, J=9.18, 1.95 Hz, 1H) 7.08-7.18 (m, 3H) 6.13 (br. s., 1H) 3.88 (s, 2H) 3.62 (s, 3H) 3.29 (s, 3H) 2.93 (d, J=2.93 Hz, 3H) 2.88 (s, 2H) 2.79 (d, J=1.76 Hz, 7H) 1.82-1.93 (m, 1H) 0.67-0.98 (m, 3H) 0.49 (br. s., 1H). LCMS (m/z, ES$^+$)=596 (M+H+).

Step 4: Methyl 2-(2-amino-5-(N-(5-cyclopropyl-2-(4-fluorophenyl)-3-(methylcarbamoyl)benzofuran-6-yl)methylsulfonamido)phenyl)acetate A solution of methyl 2-(5-(N-(5-cyclopropyl-2-(4-fluorophenyl)-3-(methyl-carbamoyl)benzofuran-6-yl)methylsulfonamido)-2-nitrophenyl)acetate (1.00 g, 1.68 mmol) in THF (10 mL) was subjected to atmospheric hydrogenation in the presence of 20% palladium on charcoal. After 10 hours the reaction vessel was purged with nitrogen, catalyst removed by filtration through Celite, and the filtrate concentrated to dryness at reduced pressure. The crude material was subjected to flash chromatography (silica gel, hexane/EtOAc) to give the title compound in 65% yield. $^1$H NMR (400 MHz, CHLOROFORM-d) δ ppm 7.84-7.92 (m, 2H) 7.68 (s, 1H) 7.39 (s, 1H) 7.23-7.30 (m, 3H) 7.18 (t, J=8.60 Hz, 2H) 6.66 (d, J=8.40 Hz, 1H) 5.84 (d, J=4.49 Hz, 1H) 4.11-4.19 (m, 2H)

3.68 (s, 3H) 3.52 (s, 2H) 3.14-3.20 (m, 3H) 2.94-3.02 (m, 3H) 2.21-2.30 (m, 1H) 0.96 (br. s., 2H). LCMS (m/z, ES$^+$)=566 (M+H+).

Step 5: 6-(N-(4-Amino-3-(2-hydroxyethyl)phenyl) methylsulfonamido)-5-cyclopropyl-2-(4-fluorophenyl)-N-methylbenzofuran-3-carboxamide To a solution of methyl 2-(2-amino-5-(N-(5-cyclopropyl-2-(4-fluorophenyl)-3-(methylcarbamoyl)benzofuran-6-yl) methylsulfonamido)phenyl)acetate (500 mg, 0.884 mmol) in THF (6 mL) at 0° C. was added 3.5M lithium aluminum hydride/THF (0.20 mL, 0.71 mmol). After stirring for 45 minutes at 0° C. aqueous work-up followed by flash chromatography (silica gel, hexane/EtOAc) afforded the title compound in 65% yield. $^1$H NMR (400 MHz, CHLOROFORM-d) δ ppm 7.89 (dd, J=7.82, 5.47 Hz, 1H) 7.70 (s, 0H) 7.40 (s, 1H) 7.15-7.25 (m, 2H) 6.61-6.73 (m, 1H) 5.78 (br. s., 0H) 3.89 (t, J=5.96 Hz, 1H) 3.18 (s, 2H) 3.10-3.24 (m, 3H) 3.00 (d, J=4.89 Hz, 1H) 2.76 (t, J=5.86 Hz, 1H) 2.29 (br. s., 0H) 0.99 (br. s., 2H). LCMS (m/z, ES$^+$)=538 (M+H+).

Step 6: 6-(N-(4-Bromo-3-(2-hydroxyethyl)phenyl) methylsulfonamido)-5-cyclopropyl-2-(4-fluorophenyl)-N-methylbenzofuran-3-carboxamide To a solution of 6-(N-(4-amino-3-(2-hydroxyethyl)phenyl)methylsulfonamido)-5-cyclopropyl-2-(4-fluorophenyl)-N-methylbenzofuran-3-carboxamide (250 mg, 0.465 mmol) in MeCN (1 mL) maintained at 0° C. was added sodium nitrite (80 mg, 1.16 mmol) dissolved in water (0.50 mL). followed by 48% aqueous HBr (0.25 mL). The resulting mixture was treated with copper(I) bromide (133 mg, 0.930 mmol) in 48% aqueous HBr (0.30 mL). After stirring at 60° C. for 1 hour the reaction mixture was cooled to RT, diluted with water and extracted with EtOAc. The organic solution was washed with water, dried over sodium sulfate, and concentrated to dryness at reduced pressure. The crude product was purified by flash chromatography (silica gel, hexane/EtOAc) to afford the title compound in 65% yield. $^1$H NMR (400 MHz, DMSO-d$_6$) δ ppm 8.36-8.51 (m, 1H) 8.05 (s, 1H) 7.92 (dd, J=8.89, 5.37 Hz, 2H) 7.49-7.62 (m, 1H) 7.31-7.49 (m, 3H) 7.09-7.26 (m, 2H) 4.69 (t, J=5.28 Hz, 1H) 3.46-3.60 (m, 2H) 3.30-3.40 (m, 3H) 2.72-2.87 (m, 5H) 2.04-2.22 (m, 1H) 0.70-1.06 (m, 3H) 0.41 (br. s., 1H).). LCMS (m/z, ES$^+$)=601, 603 (M+H+).

Step 7: 5-Cyclopropyl-2-(4-fluorophenyl)-6-(N-(1-hydroxy-3,4-dihydro-1H-benzo[c][1,2]oxaborinin-6-yl)methylsulfonamido)-N-methylbenzofuran-3-carboxamide To a deoxygenated solution of 6-(N-(4-bromo-3-(2-hydroxyethyl)phenyl)methyl-sulfonamido)-5-cyclopropyl-2-(4-fluorophenyl)-N-methylbenzofuran-3-carboxamide (100 mg, 0.166 mmol) in 1,4-dioxane (4 mL) and water (1.0 mL) was added K$_2$CO$_3$ (92 mg, 0.665 mmol) followed by 4,4,4',4',5,5,5',5'-octamethyl-2,2'-bi(1,3,2-dioxaborolane) (84 mg, 0.33 mmol) and PdCl$_2$(dppf) (12.16 mg, 0.017 mmol) under nitrogen purging. Then the reaction mixture was heated to 70° C. for 2 h. The mixture was cooled to RT and filtered to remove solids. The filtrate was diluted with water and extracted with EtOAc. The EtOAc solution was washed with water (1×), dried over sodium sulfate, and concentrated to dryness at reduced pressure. The crude product was purified by RP-HPLC (C18, MeCN/water/0.1% formic acid) to afford the title compound in 65% yield. $^1$H NMR (400 MHz, DMSO-d6) δ ppm 7.89 (dd, J=8.60, 5.28 Hz, 2H) 7.67-7.71 (m, 1H) 7.57-7.62 (m, 1H) 7.45-7.49 (m, 1H) 7.13-7.25 (m, 4H) 5.79 (d, J=3.91 Hz, 1H) 4.31 (s, 1H) 4.19 (t, J=5.96 Hz, 2H) 3.29 (s, 3H) 3.01 (d, J=4.89 Hz, 3H) 2.89 (t, J=5.86 Hz, 2H) 2.02-2.13 (m, 1H) 1.02 (br. s., 1H) 0.83 (br. s., 2H) 0.61 (br. s., 1H). LCMS (m/z, ES$^+$)=549 (M+H+).

Example 31

6-(N-(7-chloro-1-hydroxy-1,3-dihydrobenzo[c][1,2] oxaborol-5-yl)methylsulfonamido)-5-cyclopropyl-2-(4-fluorophenyl)-N-methylbenzofuran-3-carboxamide

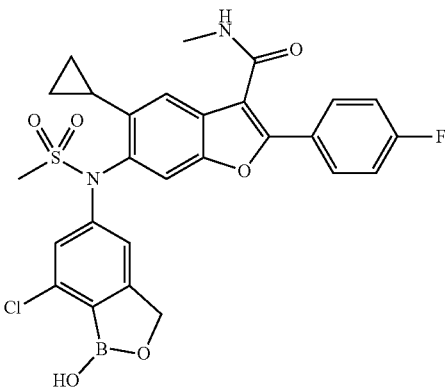 [SMILES: CNC(=O)c1c(-c2ccc(F)cc2)oc2cc(N(c3cc(Cl)c4c(c3)COB4O)S(C)(=O)=O)c(C3CC3)cc12]

Step 1: methyl 5-(N-(5-cyclopropyl-2-(4-fluorophenyl)-3-(methylcarbamoyl)benzofuran-6-yl)methylsulfonamido)-2-nitrobenzoate A mixture of 55.0 g (123 mmol) of 5-cyclopropyl-2-(4-fluorophenyl)-N-methyl-6-(methylsulfonamido)benzofuran-3-carboxamide, 36.7 g (184 mmol) of methyl 5-fluoro-2-nitrobenzoate, and 39.1 g (369 mmol) of sodium carbonate in 400 mL of DMF was heated to 70° C. with vigorous stirring. After 72 hours LCMS indicated nearly complete reaction. The mixture was cooled to RT, diluted with 300 mL of EtOAc, and filtered through a bed of celite to remove solids. The filter cake was washed with EtOAc until the filtrate ran colorless which gave a total filtrate volume of 1.2 L. The filtrate was transferred to a separatory funnel, partitioned with 1.4 L of 5% aqueous NaCl, and the phases separated. The aqueous solution was extracted with two additional 300 mL portions of EtOAc. The combined EtOAc solutions were washed with 95% aqueous NaCl (2×), saturated aqueous NaCl (1×), dried over sodium sulfate and concentrated to approximately 200 mL by rotary evaporation. At this point a solid began to crystallize. The suspension was diluted with 200 mL of DCM and the suspension stirred overnight. The suspension was then cooled in an ice water bath for 2 hours and the solid collected by vacuum filtration. The filter cake was washed twice with cold 1:1 EtOAc/DCM, suction air dried for 30 minutes and then dried in vacuo overnight to afford 59.6 g (83%) of methyl 5-(N-(5-cyclopropyl-2-(4-fluorophenyl)-3-(methylcarbamoyl)benzofuran-6-yl)methylsulfonamido)-2-nitrobenzoate as a light yellow solid. $^1$H NMR (400 MHz, DMSO-d$_6$) δ ppm 8.52 (q, J=4.42 Hz, 1H) 8.13 (d, J=9.07 Hz, 1H) 8.08 (s, 1H) 7.93-8.01 (m, 2H) 7.57 (d, J=2.63 Hz, 1H) 7.53 (dd, J=9.07, 2.73 Hz, 1H) 7.38-7.46 (m, 2H) 7.29 (s, 1H) 3.83 (s, 3H) 3.60 (s, 3H) 2.85 (d, J=4.59 Hz, 3H) 1.87-2.04 (m, 1H) 0.87 (m, 2H) 0.73 (m, 1H) 0.46 (m, 1H). LCMS (ESI): 582 (M+H+).

Step 2: methyl 2-amino-5-(N-(5-cyclopropyl-2-(4-fluorophenyl)-3-(methylcarbamoyl)benzofuran-6-yl)methylsulfonamido)benzoate A stirred suspension of 59.5 g (102 mmol) of methyl 5-(N-(5-cyclopropyl-2-(4-fluorophenyl)-3-(methylcarbamoyl)benzofuran-6-yl)methylsulfonamido)-2-nitrobenzoate and 6.0 g of 10% Pd(C) in 1.2 L of 2:1 THF/EtOH was saturated with hydrogen by bubbling hydrogen gas through for 10 minutes and then subjected to balloon hydrogenation at RT. After 6 hours LCMS indicated complete reaction. After 24 hours the mixture was purged with nitrogen, catalyst removed by filtration through celite, and the filtrate concentrated to dryness at reduced pressure to give a light yellow solid. This material was recrystallized from hot EtOAc to afford 42.2 g of methyl 2-amino-5-(N-(5-cyclopropyl-2-(4-fluorophenyl)-3-(methylcarbamoyl)benzofuran-6-yl)methylsulfonamido)benzoate as a white solid. The filtrate was concentrated to dryness at reduced pressure to give an additional 13.0 g of methyl 2-amino-5-(N-(5-cyclopropyl-2-(4-fluorophenyl)-3-(methylcarbamoyl)benzofuran-6-yl)methylsulfonamido)benzoate as a light yellow foam determined to be 95% pure by LCMS. The two batches were combined for a total yield of 55.2 g (98%) of methyl 2-amino-5-(N-(5-cyclopropyl-2-(4-fluorophenyl)-3-(methylcarbamoyl)benzofuran-6-yl)methylsulfonamido)benzoate. $^1$H NMR (400 MHz, DMSO-$d_6$) δ ppm 8.46 (q, J=4.42 Hz, 1H) 8.16 (s, 1H) 7.91-8.00 (m, 3H) 7.61 (dd, J=8.98, 2.73 Hz, 1H) 7.41 (t, J=8.88 Hz, 2H) 7.15 (s, 1H) 6.76-6.86 (m, 3H) 3.79 (s, 3H) 3.28 (s, 3H) 2.83 (d, J=4.68 Hz, 3H) 2.25-2.38 (m, 1H) 0.82-1.10 (m, 3H) 0.42 (m, 1H). LCMS (ESI): 552 (M+H+).

Step 3: methyl 2-amino-3-chloro-5-(N-(5-cyclopropyl-2-(4-fluorophenyl)-3-(methylcarbamoyl)benzofuran-6-yl)methylsulfonamido)benzoate A suspension of 55.0 g (100 mmol) of methyl 2-amino-5-(N-(5-cyclopropyl-2-(4-fluorophenyl)-3-(methylcarbamoyl)benzofuran-6-yl)methylsulfonamido)benzoate in 320 mL of DMF was heated to 60° C. The resulting yellow solution was treated with 14.0 g (105 mmol) of NCS in one portion. The solution quickly darkened. After 5 minutes LCMS indicated complete conversion to the desired chloro compound. The solution was cooled to RT and diluted with 1 L of EtOAc. The resulting solution was washed with 5% aqueous NaCl (1×1 L), 5% aqueous sodium bisulfite (2×200 mL), saturated aqueous sodium bicarbonate (3×200 mL), and saturated aqueous brine (1×200 mL). The solution was dried over sodium sulfate and concentrated to dryness at reduced pressure to give 58.0 g (99%) of methyl 2-amino-3-chloro-5-(N-(5-cyclopropyl-2-(4-fluorophenyl)-3-(methylcarbamoyl)benzofuran-6-yl)methylsulfonamido)benzoate as a brown solid. This material was taken forward to the next step without purification. $^1$H NMR (400 MHz, DMSO-$d_6$) δ ppm 8.46 (q, J=4.42 Hz, 1H) 8.25 (s, 1H) 7.94-8.04 (m, 3H) 7.90 (d, J=2.63 Hz, 1H) 7.34-7.46 (m, 2H) 7.18 (s, 1H) 6.93 (br. s., 2H) 3.83 (s, 3H) 3.33 (s, 3H) 2.84 (d, J=4.59 Hz, 3H) 2.26-2.36 (m, 1H) 0.84-1.11 (m, 3H) 0.40 (br. s., 1H). LCMS (ESI): 586 (M+H+).

Step 4: methyl 2-bromo-3-chloro-5-(N-(5-cyclopropyl-2-(4-fluorophenyl)-3-(methylcarbamoyl)benzofuran-6-yl)methylsulfonamido)benzoate To a 1 L 3-necked flask equipped with a magnetic stirrer was added 58.0 g (99.0 mmol) of methyl 2-amino-3-chloro-5-(N-(5-cyclopropyl-2-(4-fluorophenyl)-3-(methylcarbamoyl)benzofuran-6-yl)methylsulfonamido)benzoate followed by 500 mL of MeCN and then 500 mL of 48% aqueous HBr. The dark brown solution was cooled to 0° C. in an ice water/brine bath and treated with a solution of 8.20 g (119 mmol) of sodium nitrite in 50 mL of water over a 5 minute period. After 30 minutes LCMS indicated complete consumption of the starting material. The solution was treated with 18.5 g (129 mmol) of CuBr over 2 minutes and then warmed to 50° C. After 30 minutes at 50° C. LCMS indicated complete reaction. The solution was cooled to RT and partitioned between 1 L of EtOAc and 1.5 L of water. The phases were separated and the aqueous solution extracted with EtOAc (2×200 mL). The combined EtOAc solutions were washed with 5% aqueous NaCl (1×1 L), 5% aqueous sodium bisulfite (2×300 mL), saturated aqueous sodium bicarbonate (2×300 mL), saturated aqueous brine (1×300 mL), and dried over sodium sulfate. The drying agent was removed by filtration through a pad of silica gel and the filtrate concentrated to dryness at reduced pressure to give 64.3 g of crude methyl 2-bromo-3-chloro-5-(N-(5-cyclopropyl-2-(4-fluorophenyl)-3-(methylcarbamoyl)benzofuran-6-yl)methylsulfonamido)benzoate as a reddish-brown foam. The crude product was carried forward without further purification. $^1$H NMR (400 MHz, DMSO-$d_6$) δ ppm 8.50 (q, J=4.29 Hz, 1H) 8.16 (s, 1H) 7.92-8.03 (m, 2H) 7.79 (d, J=2.73 Hz, 1H) 7.65 (d, J=2.73 Hz, 1H) 7.41 (t, J=8.93 Hz, 2H) 7.24 (s, 1H) 3.81-3.89 (m, 3H) 3.45-3.53 (m, 3H) 2.85 (d, J=4.59 Hz, 3H) 2.04-2.16 (m, 1H) 0.71-1.07 (m, 3H) 0.40 (br. s., 1H). LCMS (ESI): 649 (M+H+).

Step 5: 6-(N-(4-bromo-3-chloro-5-(hydroxymethyl)phenyl)methylsulfonamido)-5-cyclopropyl-2-(4-fluorophenyl)-N-methylbenzofuran-3-carboxamide A solution of 54.3 g (84.0 mmol) of crude methyl 2-bromo-3-chloro-5-(N-(5-cyclopropyl-2-(4-fluorophenyl)-3-(methylcarbamoyl)benzofuran-6-yl)methylsulfonamido)benzoate in 351 mL of anhydrous THF and 39 mL of anhydrous MeOH was cooled in an ice water/brine bath to −5° C. (internal temperature). To the stirred solution was added 125 mL (251 mmol) of 2M LiBH$_4$/THF via addition funnel at a rate so as to maintain the temperature below 5° C. The addition required 35 minutes. The brine bath was then replaced by an ice water bath and stirring of the solution continued. After another 1.5 hours LCMS indicated complete reaction. The solution was quenched by addition of 200 mL of saturated aqueous sodium bicarbonate followed by 400 mL of water and 600 mL of EtOAc. The mixture was stirred vigorously for 30 minutes and then transferred to a separatory funnel. After the phases separated, solid remained in the aqueous phase so an additional 200 mL of water was added and the mixture shaken, and the phases again separated. The aqueous solution was extracted with EtOAc (2×200 mL). The combined EtOAc solutions were washed with 5% aqueous NaCl (1×), saturated brine (1×), dried over sodium sulfate and concentrated to dryness at reduced pressure to afford 54.5 g of 6-(N-(4-bromo-3-chloro-5-(hydroxymethyl)phenyl)methylsulfonamido)-5-cyclopropyl-2-(4-fluorophenyl)-N-methylbenzofuran-3-carboxamide as an orange-brown foam. The crude material was carried forward to the next step without purification. $^1$H NMR (400 MHz, DMSO-$d_6$) δ ppm 8.45-8.54 (m, 1H) 8.12 (s, 1H) 7.98 (dd, J=8.93, 5.41 Hz, 2H) 7.59 (d, J=2.73 Hz, 1H) 7.54 (d, J=2.63 Hz, 1H) 7.41 (t, J=8.88 Hz, 2H) 7.22 (s, 1H) 5.64 (t, J=5.56 Hz, 1H) 4.48 (d, J=5.56 Hz, 2H) 3.45 (s, 3H) 2.84 (d, J=4.59 Hz, 3H) 2.06-2.17 (m, 1H) 0.75-1.06 (m, 3H) 0.47 (br. s., 1H). LCMS (ESI): 623 (M+H+).

Step 6: 6-(N-(4-bromo-3-chloro-5-((methoxymethoxy)methyl)phenyl)methylsulfonamido)-5-cyclopropyl-2-(4-fluorophenyl)-N-methylbenzofuran-3-carboxamide A solution of 50.0 g (80.0 mmol) of crude 6-(N-(4-bromo-3-chloro-5-(hydroxymethyl)phenyl)methylsulfonamido)-5-cyclopropyl-2-(4-fluorophenyl)-N-methylbenzofuran-3-carboxamide in 500 mL of THF was treated with 42.1 mL (241 mmol) of DIEA followed by 15.3 mL (201 mmol) of MOM-Cl and the resulting solution was heated to 50° C. with stirring. After 18 hours LCMS indicated complete reaction. The solution was cooled to RT and diluted with 600 mL of EtOAc followed by 600 mL of water. After stirring vigorously for 10 minutes the mixture was transferred to a separatory funnel and the phases separated. The aqueous phase was extracted with one additional 200 mL portion of EtOAc. The combined EtOAc solutions were washed with an aqueous solution of 5% citric acid and 5% NaCl (3×300 mL), saturated aqueous sodium bicarbonate (2×300 mL), saturated brine (1×300 mL), and dried over sodium sulfate. The drying agent was removed by filtration and the filtrate concentrated to dryness at reduced pressure to give an orange-brown foam. This material was dissolved in 250 mL of EtOAc and the solution heated to reflux with stirring. To the solution was added 375 mL of hexane over a 5 minute period maintaining reflux temperature. The solution was then allowed to cool to RT with stirring during which time a light tan solid crystallized. After 2 hours the solution was cooled in an ice water bath and stirred for an additional 2 hours. The solid was collected by filtration in a medium fritted funnel. The filter cake was washed with 250 mL of cold 3:2 hexane/EtOAc, dried by suction filtration for 30 minutes, and then dried in vacuo to give 36.4 g of 6-(N-(4-bromo-3-chloro-5-((methoxymethoxy)methyl)phenyl)methylsulfonamido)-5-cyclopropyl-2-(4-fluorophenyl)-N-methylbenzofuran-3-carboxamide as a light tan solid. $^1$H NMR (400 MHz, DMSO-$d_6$) δ ppm 8.49 (q, J=4.30 Hz, 1H) 8.14 (s, 1H) 7.93-8.00 (m, 2H) 7.62 (d, J=2.74 Hz, 1H) 7.52 (d, J=2.74 Hz, 1H) 7.40 (t, J=8.94 Hz, 2H) 7.21 (s, 1H) 4.68 (s, 2H) 4.57 (s, 2H) 3.44 (s, 3H) 3.24 (s, 3H) 2.83 (d, J=4.59 Hz, 3H) 2.06-2.19 (m, 1H) 0.74-1.05 (m, 3H) 0.44 (br. s., 1H).

Step 7: 6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide A mixture of 46.4 g (69.7 mmol) of 6-(N-(4-bromo-3-chloro-5-((methoxymethoxy)methyl)phenyl)methylsulfonamido)-5-cyclopropyl-2-(4-fluorophenyl)-N-methylbenzofuran-3-carboxamide, 44.2 g of bis(pinacolato)diboron (174 mmol), 27.4 g (279 mmol) of potassium acetate, and 2.10 g (3.48 mmol) of Pd(dppb)Cl$_2$ in 350 mL of 1,4-dioxane was sparged with nitrogen for 15 minutes and then heated to 108° C. under nitrogen. After 22 hours LCMS showed complete conversion of starting material to an 84:16 mixture of desired product/protio by-product (replacement of bromine by hydrogen). The mixture was cooled to RT, combined with the crude reaction mixture from a 1 g scale pilot reaction, and diluted with 500 mL of EtOAc. The mixture was filtered through a pad of silica gel to remove solids and the filtrate was concentrated at reduced pressure to give 93.1 g of 6-(N-(3-chloro-5-((methoxymethoxy)methyl)-4-(4,4,5,5-tetramethyl-1,3,2-dioxaborolan-2-yl)phenyl)methylsulfonamido)-5-cyclopropyl-2-(4-fluorophenyl)-N-methylbenzofuran-3-carboxamide as a light tan solid. LCMS (ESI): 713 (M+H+). This material was dissolved in 524 mL of 5:1 THF/MeOH and the solution treated with 440 mL of 1N aqueous HCl. A tan solid rapidly precipitated. The mixture was heated to 70° C. The solid slowly dissolved affording a yellow solution. After 18 hours LCMS indicated complete reaction. The solution was cooled to approximately 40° C. and poured into a rapidly stirred mixture of 1 L of water and 1 L of MTBE. To the mixture was added 440 mL of 1N aqueous NaOH. The pH was then adjusted to around 12-13 by addition of 3N aqueous NaOH. The mixture was transferred to a separatory funnel and the phases separated. Analysis of the two phases by TLC and LCMS indicated nearly complete separation of the desired product from the protio by-product. The aqueous phase was washed with MTBE (3×250 mL) and then treated with concentrated HCl to a pH of approximately 2. The resulting cloudy solution was extracted with EtOAc (4×500 mL). The combined EtOAc extracts were washed with 5% aqueous brine (1×), saturated aqueous brine (1×), and dried over sodium sulfate. The drying agent was removed by filtration through a pad of celite to give a light yellow filtrate. The filtrate was concentrated to dryness at reduced pressure to give 39.0 g of a tan foam. This material was dissolved in 400 mL of MeCN. The resulting solution was stirred with slow addition of 800 mL of 0.1N aqueous HCl via addition funnel over a 40 minute period. Early in the addition the solution was seeded with a small amount of previously prepared, crystalline 6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide which induced vigorous crystallization. The suspension was stirred overnight at RT. The solid was collected by vacuum filtration rinsing with 2:1 MeCN water. The material was suction air dried for 1 hour and then dried to constant weight in vacuo to afford 28.8 g (71%) of 6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide as an off-white powder. $^1$H NMR (400 MHz, DMSO-$d_6$) δ ppm 9.18 (s, 1H) 8.50 (q, J=4.42 Hz, 1H) 8.09 (s, 1H) 7.93-8.02 (m, 2H) 7.37-7.46 (m, 3H) 7.28 (d, J=1.56 Hz, 1H) 7.22 (s, 1H) 4.97 (s, 2H) 3.48 (s, 3H) 2.85 (d, J=4.59 Hz, 3H) 2.02-2.14 (m, 1H) 0.92-1.04 (m, 1H) 0.82 (br. s., 2H) 0.49 (br. s., 1H). LCMS (ESI): 569 (M+H+).

Example 32

Biological Activity

Replicon Luciferase Cell Based Assay
Method
150 µL of a 1 mM stock solution in DMSO of each test compound was transferred into in the first column of a 96 well, V-bottom microplate, to give 200 times the top concentration of the required dilution series. Aliquots of 50 µL were added to each well of the remaining rows containing 100 µL of DMSO giving a 1:3 dilution series over ten points. Columns 11 and 12 contained DMSO only for the positive and negative control, respectively. 10 µL of each well were transferred into 90 µL of DMEM medium (Invitrogen #41965-039) supplemented with 5% v/v foetal calf serum, 1% v/v non-essential amino acids solution, 100 units/ml penicillin, 100 µg/ml streptomycin and 2 mM L-glutamine to give 20 times the top concentration of the required dilution series.

Suspensions were prepared from cultures of Huh-7 cells stably transfected with sub-genomic HCV NS3-NS5B replicons of either genotype 1b (the ET subline described by Pietschmann, T., Lohmann, V., Kaul, A., Krieger, N., Rinck, G., Rutter, G., Strand, D. & Bartenschlager, R., *Journal of Virology*, 2002, 76, 4008-4021), genotype 1a (subline 1.19 constructed in-house from H77 SG-Neo containing adaptive mutations P1496L and S2204I as described by Blight, K. J., McKeating, J. A., Marcotrigiano, J., and Rice, C. M. Journal of Virology, 2003, 77, 3180-3190), genotype 1b C316N (constructed in-house by site directed mutagenesis of the NS5B gene of the ET subline), or genotype 1a C316Y (constructed in-house by site directed mutagenesis of the NS5B gene of H77 SG-Neo containing adaptive mutations P1496L and S2204I as described by Blight, K. J., McKeating, J. A., Marcotrigiano, J., and Rice, C. M. Journal of Virology, 2003, 77, 3180-3190) linked to a firefly luciferase reporter gene. Monolayers nearing confluency were stripped from growth flasks with versene-trypsin solution and the cells re-suspended in assay medium comprising DMEM. 95 μL of suspension containing either 15,000 cells (genotype 1b luciferase replicon) or 20,000 cells (genotype 1a luciferase replicon) were added to all wells of a 96 well plate (Perkin Elmer, #6005686), except medium controls in column 12 of the assay plate. The cell suspension was dosed with 5 μL of compound solution and the plate was incubated for 48 hours at 37° C. in a 5% $CO_2$ atmosphere.

For toxicity the cells in one plate were treated with Cell Titer Glo (Promega, #G7573). A solution of Cell Titer Glo was prepared according to the manufacturer's instructions, and 100 μL added to each well. The plate was then read for luminescence on an Envision. For potency a solution of Steady Glo (Promega, #E2550) was prepared according to the manufacturer's instructions and 100 μL added to each well. After a twenty minute incubation the plate was then read for luminescence on an Envision.

Data Analysis

Toxicity: The luminescence values from duplicate wells were averaged and expressed as a percentage of the mean absorbance of compound free control wells to determine comparative cell viability. Compound cytotoxicity was expressed either as the lowest concentration at which a significant reduction in viability was observed or a 50% toxic concentration ($CCID_{50}$) was determined by plotting percentage cytotoxicity against compound concentration using ActivityBase (IDBS Software) with curve fitting done through the XC50 module.

Potency: The luminescence values from all compound-free wells containing cells were averaged to obtain a positive control value. The mean luminescence value from the compound-free wells that had received no cells was used to provide the negative (background) control value. The readings from the wells at each compound concentration were taken and after the subtraction of the mean background from all values, were expressed as a percentage of the positive control signal. The quantifiable and specific reduction of luciferase signal in the presence of a drug is a direct measure of replicon inhibition. BioAssay Enterprise (CamebridgeSoft) with the XC50 module for curve fitting was used to plot the curve of percentage inhibition against compound concentration and derive the 50% inhibitory concentration ($EC_{50}$) for the compound. $EC_{50}$ is the effective concentration, that is, the concentration of compound where 50% maximal effect is observed. The $EC_{50}$ values of two identical plates were averaged. The results are presented in Table 1 as $EC_{50}$ for genotypes (GT) 1a, 1b, 1b 316N and 1a 316Y.

TABLE 1

| Example No. | GT 1a | GT1b | 1b 316N | 1a 316Y |
|---|---|---|---|---|
| 1 | *** | *** | *** | *** |
| 2 | *** | *** | *** | *** |
| 3 | *** | *** | *** | * |
| 4 | *** | *** | ** | + |
| 5 | *** | *** | *** | ** |
| 6 | *** | *** | ** | + |
| 7 | *** | *** | *** | ** |
| 8 | + | + | + | ND |
| 9 | *** | *** | *** | ** |
| 10 | *** | *** | *** | ** |
| 11 | ND | ND | ND | ND |
| 12 | *** | *** | *** | ** |
| 13 | + | + | + | ND |
| 14 | *** | *** | *** | ** |
| 15 | *** | *** | *** | ** |
| 16 | *** | *** | ** | ** |
| 18 | ND | *** | ** | ** |
| 19 | *** | *** | *** | *** |
| 20 | *** | *** | *** | ** |
| 21 | *** | *** | *** | *** |
| 22 | *** | *** | *** | * |
| 23 | *** | *** | ** | ** |
| 24 | *** | *** | *** | ** |
| 25 | *** | *** | ** | ** |
| 26 | *** | *** | ** | * |
| 27 | *** | *** | ** | ** |
| 28 | *** | *** | ** | ** |
| 29 | *** | *** | ** | ** |
| 30 | *** | *** | *** | ND |

+ >1000

* 200-1000 nM

** 11-200 nM

*** 1-10 nM

ND not determined

Example 33

Pharmacokinetics

In vivo pharmacokinetic studies were conducted in mouse, rat, dog, or cynomolgus monkey to determine clearance, oral exposure and bioavailability (% F). Solution doses of the compounds were administered intravenously through catheters or orally by gavage. Blood samples were collected at the following time points (n=2 or 3/route/species): 0.083 (IV only), 0.167 (IV only), 0.25, 0.5, 1, 2, 4, 6, 8, 12, and 24 h. Non-compartmental pharmacokinetic parameters were determined using Phoenix Winnonlin 6.1 (Pharsight, Mountain View, Calif.). Bioavailability of the oral formulation of each compound were calculated as the ratio of the oral dose normalized $AUC_{inf}$ to the intravenous dose normalized $AUC_{inf}$. Results are expressed in Table 2.

TABLE 2
| | Cl (ml/min/kg) | Vss (L/kg) | T 1/2 (H) | DNAUC (ng · h/ml/mg/kg) | % F |
|---|---|---|---|---|---|
Ex. 1
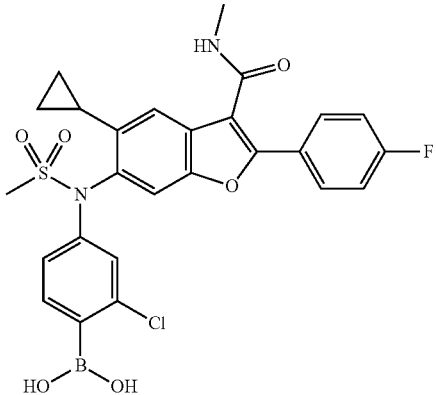 [SMILES: CNC(=O)c1c(-c2ccc(F)cc2)oc2cc(N(c3ccc(B(O)O)c(Cl)c3)S(C)(=O)=O)c(C3CC3)cc12]
| Mouse | 0.9 | 0.4 | 5.5 | 6688 | 37 |
| Rat | 7.5 | 1.3 | 2.9 | 567 | 23 |
| Dog | 2.3 | 1.6 | 8.7 | 6438 | 83 |
| Monkey | 2.2 | 0.5 | 3.7 | 2953 | 51 |
A
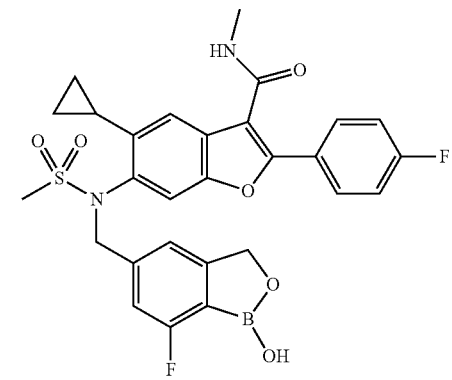 [SMILES: CNC(=O)c1c(-c2ccc(F)cc2)oc2cc(N(Cc3cc(F)c4c(c3)COB4O)S(C)(=O)=O)c(C3CC3)cc12]
| Mouse (avg) | 0.9 | 0.3 | 4.3 | 9344 | 51 |
| Rat | 14.5 | 1.0 | 1.7 | 541 | 47 |
| Dog | 12.4 | 3.5 | 5.1 | 1074 | 71 |
| Monkey | 70.1 | 6.3 | 2.1 | 33 | 13 |
B
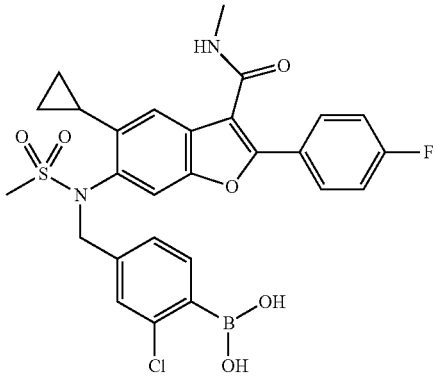 [SMILES: CNC(=O)c1c(-c2ccc(F)cc2)oc2cc(N(Cc3ccc(B(O)O)c(Cl)c3)S(C)(=O)=O)c(C3CC3)cc12]
TABLE 2-continued
| | Cl (ml/min/kg) | Vss (L/kg) | T 1/2 (H) | DNAUC (ng · h/ml/mg/kg) | % F |
|---|---|---|---|---|---|
| Rat | 33.1 | 2.5 | 1.1 | 122 | 23 |
C
| Rat | 15.6 | 1.1 | 1.8 | 434 | 40 |
D
| Mouse (avg) | 1.4 | 0.6 | 5 | 4108 | 37 |
| Rat | 18.6 | 0.8 | 2.2 | 403 | 45 |
| Dog | 10.8 | 3.6 | 4.5 | 1147 | 70 |
| Monkey (plasma) | 48.4 | 1.8 | 1.1 | 101 | 28 |
Ex. 15
| Mouse | 0.7 | 0.4 | 8.4 | 14603 | 39 |
| Rat | 6.9 | 0.9 | 2.8 | 1089 | 43 |
| Dog | 1.2 | 0.6 | 6.9 | 11480 | 82 |
| Monkey | 5.7 | 1.2 | 3.7 | ND | ND |
A = Example 42 of PCT/US2011/024824 (WO2012/067663)
B = Example 39 of PCT/US2011/024822 (WO2011/103063)
C = Example 14 of PCT/US2011/024822 (WO2011/103063)
D = Example 9 of PCT/US2011/024822 (WO2011/103063)
ND = not determined

Example 34

Human Hepatocytes

Hepatocyte incubations were conducted using cryopreserved hepatocytes purchased from CellzDirect (Durham, N.C.). Cryopreserved hepatocytes were removed from liquid nitrogen and thawed according to XenoTech's guidelines listed in "XenoTech Protocol for Thawing Cryopreserved Hepatocytes" using Hepatocyte Isolation Kit K2000 (Dec. 13, 2004). Hepatocytes were diluted to 1 million cells in 1 mL of Williams E media containing 25 mM HEPES buffer and 2 mM Glutamax.

Hepatocyte incubations were carried out in 96-well plates on an Eppendorf shaker at 350 rpm at 37 C. Reaction mixtures consisted of $0.25 \times 10^6$ cells and 0.5 mM test compound (to maintain a 0.05% final DMSO concentration) in a final volume of 0.5 mL. An initial time-point ($t_0$) was collected and subsequent aliquots were collected at 15, 30, 60, 90, and 120 min. Reactions were terminated by transferring 50 mL of the incubation mixture into a 96-well plate containing 100 mL of an organic mixture [acetonitrile and methanol (80:20)] at 4° C. Precipitated protein was removed by centrifugation and the resultant supernatant was transferred to a new 96-well polypropylene plate for LC/MS/MS analysis. Drug-free matrix control and 2 QC standards (phenacetin and propranolol) were included in each experiment and treated in the same manner as test compound.

Metabolic stability expressed as the percentage of parent compound remaining was calculated from the peak area ratio of compound remaining after incubation ($t_x$) compared to the time zero ($t_0$) incubation.

$$\% \text{ Compound remaining} = \frac{\text{Peak area at time post incubation } (t_x)}{\text{Peak area at time zero } (t_0)} \times 100$$

The half-life ($t_{1/2}$) was calculated using the following equation:

$$t_{1/2} = \frac{-\ln(2)}{K}$$

Where K is the slope of the ln % remaining vs. time regression. Half-life values were only reported when at least 15% loss of parent compound was observed.

Intrinsic clearance determined from microsome hepatocyte incubations ($CI'_{int}$, mL/min/kg body weight) was calculated from the half-life values using the following equations (Obach, Obach, R S J. Pharmacol. Expt Ther., 283:46-58, 1997):

$$CI'_{int} \text{ hepatocytes} = \frac{0.693}{t1/2 \text{ (min)}} \times \frac{\text{(mL incubation)}}{\text{\# cells}} \times C \times B$$

Where B=g liver/kg body wt (Davies and Morris, 1993), C=# cells/g liver (Iwatsubo, Pharmacol. Ther., 73:147-171, 1997)

B=$1.2 \times 10^8$ cells/g for mouse, rat, cynomolgus monkey and human and $2.4 \times 10^8$ cells/g for dog C=87.5 gm liver/kg body wt for mouse, 40 gm liver/kg body wt for rat, 32 gm liver/kg body wt for dog, 20 gm liver/kg body wt for cynomolgus monkey, 26 gm liver/kg body wt for human.

If a half life value was determined to be greater than three times the last time point (i.e. $t_{1/2}$>360 min in hepatocytes), no $CI'_{int}$ value was reported.

Results: T ½ (min) for Example 1 was >360; A>360; B=45; C (not determined); D=61.6; Example 15>360.

The invention claimed is:
1. A compound having the formula:

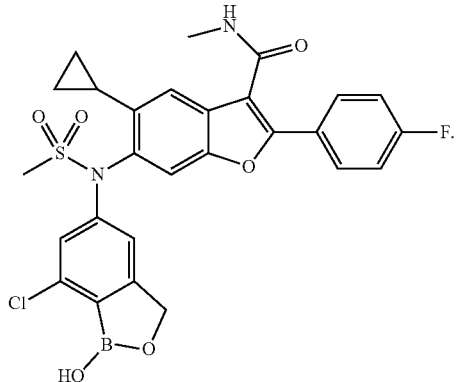 [SMILES: CNC(=O)c1c(-c2ccc(F)cc2)oc2cc(N(c3cc(Cl)c4c(c3)COB4O)S(C)(=O)=O)c(C3CC3)cc12]

2. A compound having the formula:

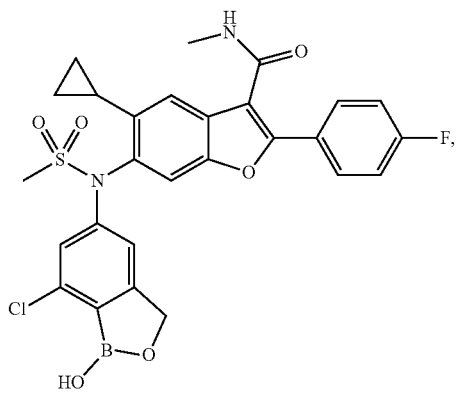 [SMILES: CNC(=O)c1c(-c2ccc(F)cc2)oc2cc(N(c3cc(Cl)c4c(c3)COB4O)S(C)(=O)=O)c(C3CC3)cc12]

or a pharmaceutically acceptable salt thereof.

3. A pharmaceutically acceptable salt of a compound having the formula:

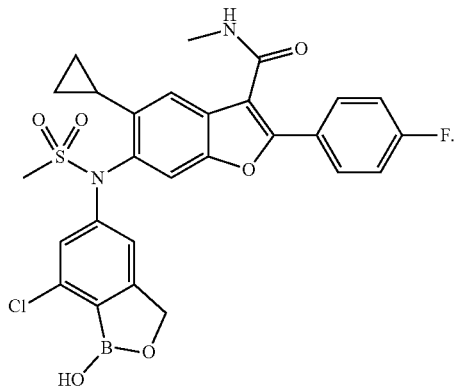 [SMILES: CNC(=O)c1c(-c2ccc(F)cc2)oc2cc(N(c3cc(Cl)c4c(c3)COB4O)S(C)(=O)=O)c(C3CC3)cc12]

* * * * *